United States Patent
Johansson et al.

(10) Patent No.: US 8,729,235 B2
(45) Date of Patent: *May 20, 2014

(54) SPIDER SILK PROTEINS AND METHODS FOR PRODUCING SPIDER SILK PROTEINS

(71) Applicant: Spiber Technologies AB, Uppsala (SE)

(72) Inventors: Jan Johansson, Stockholm (SE); Göran Hjäm, Uppsala (SE); Margareta Stark, Hagersten (SE); Anna Rising, Uppsala (SE); Stefan Grip, Uppsala (SE); Wilhelm Engström, Saltsjo-Boo (SE); My Hedhammar, Stockholm (SE)

(73) Assignee: Spiber Technologies AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,244

(22) Filed: Nov. 21, 2013

(65) Prior Publication Data

US 2014/0079674 A1 Mar. 20, 2014

Related U.S. Application Data

(63) Continuation of application No. 13/598,119, filed on Aug. 29, 2012, now Pat. No. 8,618,255, which is a continuation of application No. 13/441,118, filed on Apr. 6, 2012, now Pat. No. 8,278,416, which is a continuation of application No. 12/087,289, filed as application No. PCT/SE2006/001505 on Dec. 28, 2006, now Pat. No. 8,173,772.

(30) Foreign Application Priority Data

Dec. 30, 2005 (SE) .................................... 0502932-7

(51) Int. Cl.
| | |
|---|---|
| C07K 1/00 | (2006.01) |
| C07K 14/00 | (2006.01) |
| C12N 11/08 | (2006.01) |
| C12M 1/00 | (2006.01) |
| C12P 1/00 | (2006.01) |
| A61F 13/00 | (2006.01) |
| A61K 9/70 | (2006.01) |
| A61L 15/16 | (2006.01) |

(52) U.S. Cl.
USPC ........ 530/350; 530/412; 435/180; 435/283.1; 435/41; 514/944; 514/945; 514/953; 424/422; 424/443; 424/447

(58) Field of Classification Search
None
See application file for complete search history.

(56) References Cited

U.S. PATENT DOCUMENTS

| | | | |
|---|---|---|---|
| 5,733,771 A | 3/1998 | Lewis et al. | |
| 5,994,099 A | 11/1999 | Lewis et al. | |
| 6,268,169 B1 | 7/2001 | Fahnestock | |
| 2004/0210956 A1 | 10/2004 | Roth et al. | |
| 2005/0158821 A1 | 7/2005 | Mello et al. | |

FOREIGN PATENT DOCUMENTS

| | | |
|---|---|---|
| DE | 101 13 781 A1 | 12/2001 |
| EP | 0 452 925 A2 | 10/1991 |
| WO | WO 94/29450 A2 | 12/1994 |
| WO | WO 97/08315 A1 | 3/1997 |
| WO | WO 01/53333 A1 | 7/2001 |
| WO | WO 01/90389 A2 | 11/2001 |
| WO | WO 03/020916 A2 | 3/2003 |
| WO | WO 03/057720 A2 | 7/2003 |
| WO | WO 03/057727 A1 | 7/2003 |
| WO | WO 03/060099 A2 | 7/2003 |
| WO | WO 2004/016651 A2 | 2/2004 |
| WO | WO 2004/044172 A2 | 5/2004 |
| WO | WO 2004/073644 A2 | 9/2004 |
| WO | 1 609 801 A1 | 12/2005 |
| WO | WO 2006/008163 A2 | 1/2006 |
| WO | WO 2006/083514 A2 | 8/2006 |
| WO | WO 2007/025719 A1 | 3/2007 |
| WO | WO 2007/128378 A1 | 11/2007 |

OTHER PUBLICATIONS

Arcidiacono S. et al., Appl Microbiol Biotechnol (1998), 49, p. 31-38.
Beckwitt R. and Arcidiacono S., J. Biol Chem (1994), 269, p. 6661-6663.
Beckwitt R. et al., Insect Biochemistry and Molecular Biology (1998), 28, p. 121-130.
EPO International Search Report for Appl. No. PCT/SE2006/001505 dated Oct. 31, 2007.
Fahnestock, S. R. and Bedzyk, L. A., Appl Microbiol Biotechnol (1997), 47, p. 33-39.
Fahnestock, S. R. and Irwin, S. L., Appl Microbiol Biotechnol (1997), 47, p. 23-32.

(Continued)

*Primary Examiner* — Suzanne M Noakes
*Assistant Examiner* — Jae W Lee
(74) *Attorney, Agent, or Firm* — Birch, Stewart, Kolasch, & Birch, LLP

(57) ABSTRACT

The invention provides an isolated major ampullate spidroin protein, which consists of from 150 to 420 amino acid residues and is defined by the formula REP-CT. REP is a repetitive, N-terminally derived protein fragment having from 80 to 300 amino acid residues. CT is a C-terminally derived protein fragment having from 70 to 120 amino acid residues. The invention further provides an isolated fusion protein consisting of a first protein fragment, which is a major ampullate spidroin protein, and a second protein fragment comprising a fusion partner and a cleavage agent recognition site. The first protein fragment is coupled via said cleavage agent recognition site to the fusion partner. The invention also provides a method of producing a major ampullate spidroin protein and polymers thereof.

20 Claims, 8 Drawing Sheets

(56) References Cited

OTHER PUBLICATIONS

Fahnestock, S. R. et al., Reviews in Molecular Biotechnology (2000), 74, p. 105-119.
Gatesy, J. et al., Science (2001), 291, p. 2603-2605.
Huemmerich, D. et al., Biochemistry (2004), 43, p. 13604-13612.
Huemmerich, D. et al., Curr Biology (2004), 14, p. 2070-2074.
Huemmerich, D. et al., Curr Biology (2004), 14, p. 2070-2074. Supplemental data.
Lavallie, E. R. et al., Biotechnology (1993), 11, p. 187-193.
Lawrence, B. A. et al., Biomacromolecules (2004), 5, p. 689-695.
Lazaris, A. et al., Science (2002), 295, p. 472-476. Suppl. Data.
Lazaris, A. et. al., Science (2002), 295, p. 472-476.
Lewis, R. V. et al., Protein Expression and Purification (1996), 7, p. 400-406.
Motriuk-Smith, D. et al., Biomacromolecules (2005), 6, p. 3152-3159.
Pouchkina-Stantcheva, N. N. and McQueen-Mason, S. J., Comp Biochem and Physiology, Part B (2004), 138, p. 371-376.
Prince, J. T. et al., Biochemistry (1995), 34, p. 10879-10885.
Rising A. et al., Biomacromolecules (2006), 7, p. 3120-3124.
Scheibel, T., Microbial Cell Factories (2004), 3:14, p. 1-10.
Scheller, J. et al., Nature Biotech (2001), 19, p. 573-577.
Sezutsu et al, "Dynamic Rearrangement Within the Antheraea pernyi Silk Fibroin Gene is Associated with Four Types of Repetitive Units," J Mol Evol (2000), vol. 51, pp. 329-338.
Sorensen, et al, "Soluble expression of recombinant proteins in the cytoplasm of *Escherichia coli*," Microbial Cell Factories, Jan. 2005, vol. 4, No. 1, pp. 1-8.
Sponner, A. et al., Biochem and Biophys Res Communications (2005), 338, p. 897-902.
Stark, M. et al., Biomacromolecules (2007), 8, p. 1695-1701.
Tai, P-L. et al., Int Journal of Biol Macromolecules (2004), 34, 295-301.
Thompson, Julie D. et al., Nucleic Acids Research (1994), vol. 22, No. 22, pp. 4673-4680.
Van Beek, J. D. et al., PNAS (2002), 99, 10266-10271.
Wong Po Foo, C. And Kaplan, D. L., Advanced Drug Delivery Reviews (2002), 54, 1131-1143.
Xu, Ming et al., Proc. Natl. Acad. Sci. USA, vol. 87, pp. 7120-7124, Sep. 1990.

SEQUENCE LISTING

<160> NUMBER OF SEQ ID NOS: 72

<210> SEQ ID NO 1
<211> LENGTH: 3766
<212> TYPE: DNA
<213> ORGANISM: Euprosthenops australis

<400> SEQUENCE: 1

```
gtcaaggtgc tggaggtaat gccgctgcag cagccgcagc agcagcagca gcagcagctg      60
gacagggcgg tcaaggtgga tatggtggac taggtcaagg aggatatgga cagggtgcag     120
gaagttctgc agccgccgcc gccgcagcag cagcagcagc tgcagcagct ggacgaggtc     180
aaggaggata tggtcaaggt tctggaggta atgccgctgc agcagccgca gcagctgcag     240
cagcagcatc tggacaagga ggtcaaggag gacaaggtgg acaaggtcaa ggtggatatg     300
gacaaggtgc aggaagttct gcagccgccg ccgccgcagc agcagcagcc gccgcagcag     360
ctggacaagg tcaaggacga tatggtcaag gtgctggagg taatgccgct gcagcagccg     420
cagcagctgc agcagcagca gctggacaag gaggtcaagg aggacaaggt ggactaggtc     480
aaggaggata tggacaaggt gcaggaagtt ctgcagccgc cgccgcagca tcagcagccg     540
ccgcagcagc tggacgaggt caaggaggat atggtcaagg tgctggaggt aatgccgctg     600
cagcagccgc agcagctgcc gccgccgcag cagctggaca gggtggtcaa ggtggatatg     660
gtggactagg tcaaggagga tatggacaag gtgcaggaag ttctgcagcc gctgccgccg     720
cagcagcagc agccgccgcc gcaggtggac aaggtggaca aggtcaagga agatatggac     780
aaggtgcagg aagttctgca gccgctgccg ccgcagcagc agcagccgcc gcagcagctg     840
gacaaggtca aggaggatat ggtcaaggtg ctggaggtaa tgccgctgca gcagccgcag     900
cagctgcagc agcagcagct ggacaaggag gtcaaggagg acaaggtgga ctaggtcaag     960
gaggatatgg acaaggtgca ggaagttctg ccgccgccgc cgcagcagca gcagccgccg    1020
cagcagctgg acgaggtcaa ggaggatatg gtcaaggtgc tggaggtaat gccgctgcag    1080
cagccgcagc agctgccgaa gccgcagcag ctggacaggg tggtcaaggt ggatatggtg    1140
gactaggtca aggaggatat ggacaaggtg caggaagttc tgcagccgcc gccgcagcag    1200
```

```
cagcagccgc cgcagcagct ggacgaggtc aaggaggata tggtcaaggt gctggaggta    1260
atgccgctgc agcagccgca gcagctgccg ccgccgcagc agctggacag ggtggtcaag    1320
gtggatatgg tggactaggt caaggaggat atggacaagg tgcaggaagt tctgcagccg    1380
ctgccgccgc agcagcagca gccgccgccg caggtggaca aggtggacaa ggtcaaggaa    1440
gatatggaca aggtgcagga agttctgcag ccgctgccgc cgcagcagca gcagcagccg    1500
cagcagctga cgaggtcaa ggaggatatg gtcaaggttc tggaggtaat gccgctgcag    1560
cagccgcagc agctgcagca gcagcatctg gacaaggaag tcaaggagga caaggtggac    1620
aaggtcaagg tggatatgga caaggtgcag gaagttctgc agccgccgcc gccgccgcag    1680
cagcagccgc cgcagcatct ggacgaggtc aaggaggata tggtcaaggt gctggaggta    1740
atgccgctgc tgcagccgca gcagctgccg ccgccgcagc agctggacag ggcggtcaag    1800
gtggatatgg tggactaggt caaggaggat atggacaagg tgcaggaagt tctgcagccg    1860
ctgccgccgc cgcagcagcc gccgcagcag gtggacaagg tggacaaggt caaggaggat    1920
atggacaagg tgcaggaagt tctgcagccg ccgccgcagc agcagcagca gcagccgcag    1980
cagctggacg aggtcaagga ggatatggtc aaggttctgg aggtaatgcc gctgcagcag    2040
ccgcagcagc tgcagcagca gcatctggac aaggaggtca aggaggacaa ggtggacaag    2100
gtcaaggtgg rtatggacaa ggtgcaggaa gttctgcagc cgccgccgcc gcagcagcag    2160
cagccgccgc agcagctgga caaggtcaag gaggatatgg tcaaggtgct ggaggtaatg    2220
ccgctgcagc agccgcagca gctgcagcag cagcagctgg acaaggaggt caaggaggac    2280
aaggtggact aggtcaagga ggatatggac aaggtgcagg aagttctgca gccgccgccg    2340
cagcmgcmgc agcagccgcc gcagcagctg gacgaggtca aggaggatat ggtcaaggtg    2400
ttggaggtaa tgccgctgca gcagccgcag cagctgcagc agcagcagct ggacaaggag    2460
gtcaaggagg acaaggtgga ctaggtcaag gaggatatgg acaaggtgca ggtagttctg    2520
cagccgccgc cgccgccgca gcagcagccg ccgcagcagc tggacgaggt caaggaggat    2580
atggtcaagg ttctggaggt aatgccgctg cagcagccgc agcagctgca gcagcagcat    2640
ctggacaagg aagtcaagga ggacaaggtg gacaaggtca aggtggatat ggacaaggtg    2700
caggaagttc tgcagccgcc gccgccgcag cagcagcagc cgccgcagca tctggacgag    2760
gtcaaggagg atatggtcaa ggtgctggag gtaatgccgc tgctgcagcc gcagcagctg    2820
ccgccgccgc agcagctgga cagggcggtc aaggtggata tggtggacta ggtcaaggag    2880
gatatggaca aggtgcagga agttctgcag ccgctgccgc cgcagcagca gccgccgcag    2940
caggtggaca aggtggacaa ggtcaaggag gatatggaca aggttcagga ggttctgcag    3000
ccgccgccgc cgccgcagca gcagcagcag ctgcagcagc tggacgaggt caaggaggat    3060
atggtcaagg ttctggaggt aatgctgctg ccgcagccgc tgccgccgcc gccgccgctg    3120
cagcagccgc acaggtaggt caaggtggat atggtagaca aagccaaggt gctggttccg    3180
ctgctgctgc tgctgctgct gctgccgctg ctgctgctgc aggatctgga caaggtggat    3240
acggtggaca aggtcaagga ggttatggtc agagtagtgc ttctgcttca gctgctgcgt    3300
cagctgctag tactgtagct aattcggtga gtcgcctctc atcgccttcc gcagtatctc    3360
gagtttcttc agcagtttct agcttggttt caaatggtca agtgaatatg gcagcgttac    3420
ctaatatcat ttccaacatt tcttcttctg tcagtgcatc tgctcctggt gcttctggat    3480
gtgaggtcat agtgcaagct ctactcgaag tcatcactgc tcttgttcaa atcgttagtt    3540
cttctagtgt tggatatatt aatccatctg ctgtgaacca aattactaat gttgttgcta    3600
```

-continued

```
atgccatggc tcaagtaatg ggctgaggtt tttaatagta aaaggtgtga tattcctcaa    3660
tgttttgaaa attattaatc gaattttttac cttgtgtgct atcagatata aattgaagta   3720
taataaataa atatttgcat tttcaaaaaa aaaaaaaaaa aaaaaa                   3766
```

<210> SEQ ID NO 2
<211> LENGTH: 1207
<212> TYPE: PRT
<213> ORGANISM: Euprosthenops australis

<400> SEQUENCE: 2

```
Gln Gly Ala Gly Gly Asn Ala Ala Ala Ala Ala Ala Ala Ala Ala
1               5                   10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
            35                  40                  45

Ala Ala Ala Ala Ala Ala Ala Ala Gly Arg Gly Gln Gly Gly Tyr Gly
        50                  55                  60

Gln Gly Ser Gly Gly Asn Ala Ala Ala Ala Ala Ala Ala Ala Ala
65                  70                  75                  80

Ala Ala Ser Gly Gln Gly Gly Gln Gly Gly Gln Gly Gly Gln
            85                  90                  95

Gly Gly Tyr Gly Gln Gly Ala Gly Ser Ser Ala Ala Ala Ala Ala
            100                 105                 110

Ala Ala Ala Ala Ala Ala Ala Ala Gly Gln Gly Gln Gly Arg Tyr Gly
        115                 120                 125

Gln Gly Ala Gly Gly Asn Ala Ala Ala Ala Ala Ala Ala Ala Ala
130                 135                 140

Ala Ala Ala Gly Gln Gly Gly Gln Gly Gly Gln Gly Gly Leu Gly Gln
145                 150                 155                 160

Gly Gly Tyr Gly Gln Gly Ala Gly Ser Ser Ala Ala Ala Ala Ala
            165                 170                 175

Ser Ala Ala Ala Ala Ala Ala Gly Arg Gly Gln Gly Gly Tyr Gly Gln
        180                 185                 190

Gly Ala Gly Gly Asn Ala Ala Ala Ala Ala Ala Ala Ala Ala
            195                 200                 205

Ala Ala Ala Gly Gln Gly Gly Gln Gly Gly Tyr Gly Gly Leu Gly Gln
        210                 215                 220

Gly Gly Tyr Gly Gln Gly Ala Gly Ser Ser Ala Ala Ala Ala Ala
225                 230                 235                 240

Ala Ala Ala Ala Ala Ala Ala Gly Gly Gln Gly Gly Gln Gly Gln Gly
            245                 250                 255

Arg Tyr Gly Gln Gly Ala Gly Ser Ser Ala Ala Ala Ala Ala Ala
        260                 265                 270

Ala Ala Ala Ala Ala Ala Gly Gln Gly Gln Gly Gly Tyr Gly Gln
        275                 280                 285

Gly Ala Gly Gly Asn Ala Ala Ala Ala Ala Ala Ala Ala Ala
            290                 295                 300

Ala Ala Gly Gln Gly Gly Gln Gly Gly Gln Gly Gly Leu Gly Gln Gly
305                 310                 315                 320

Gly Tyr Gly Gln Gly Ala Gly Ser Ser Ala Ala Ala Ala Ala Ala
            325                 330                 335

Ala Ala Ala Ala Ala Ala Gly Arg Gly Gln Gly Gly Tyr Gly Gln Gly
        340                 345                 350
```

```
Ala Gly Gly Asn Ala Ala Ala Ala Ala Ala Ala Glu Ala Ala
        355                 360                 365

Ala Ala Gly Gln Gly Gly Gln Gly Gly Tyr Gly Gly Leu Gly Gln Gly
    370                 375                 380

Gly Tyr Gly Gln Gly Ala Gly Ser Ser Ala Ala Ala Ala Ala Ala
385                 390                 395                 400

Ala Ala Ala Ala Ala Gly Arg Gly Gln Gly Gly Tyr Gly Gln Gly
            405                 410                 415

Ala Gly Gly Asn Ala Ala Ala Ala Ala Ala Ala Ala Ala Ala
        420                 425                 430

Ala Ala Gly Gln Gly Gly Gln Gly Gly Tyr Gly Leu Gly Gln Gly
    435                 440                 445

Gly Tyr Gly Gln Gly Ala Gly Ser Ser Ala Ala Ala Ala Ala Ala
450                 455                 460

Ala Ala Ala Ala Ala Gly Gly Gln Gly Gly Gln Gly Gln Gly Arg
465                 470                 475                 480

Tyr Gly Gln Gly Ala Gly Ser Ser Ala Ala Ala Ala Ala Ala
                485                 490                 495

Ala Ala Ala Ala Ala Ala Gly Arg Gly Gln Gly Gly Tyr Gly Gln Gly
            500                 505                 510

Ser Gly Gly Asn Ala Ala Ala Ala Ala Ala Ala Ala Ala Ala
        515                 520                 525

Ser Gly Gln Gly Ser Gln Gly Gly Gln Gly Gly Gln Gly Gly Gly
    530                 535                 540

Tyr Gly Gln Gly Ala Gly Ser Ser Ala Ala Ala Ala Ala Ala Ala
545                 550                 555                 560

Ala Ala Ala Ala Ala Ser Gly Arg Gly Gln Gly Gly Tyr Gly Gln Gly
            565                 570                 575

Ala Gly Gly Asn Ala Ala Ala Ala Ala Ala Ala Ala Ala Ala
        580                 585                 590

Ala Ala Gly Gln Gly Gly Gln Gly Gly Tyr Gly Gly Leu Gly Gln Gly
    595                 600                 605

Gly Tyr Gly Gln Gly Ala Gly Ser Ser Ala Ala Ala Ala Ala Ala
610                 615                 620

Ala Ala Ala Ala Ala Gly Gly Gln Gly Gly Gln Gly Gln Gly Gly Tyr
625                 630                 635                 640

Gly Gln Gly Ala Gly Ser Ser Ala Ala Ala Ala Ala Ala Ala
                645                 650                 655

Ala Ala Ala Ala Ala Gly Arg Gly Gln Gly Gly Tyr Gly Gln Gly Ser
            660                 665                 670

Gly Gly Asn Ala Ala Ala Ala Ala Ala Ala Ala Ala Ala Ser
        675                 680                 685

Gly Gln Gly Gly Gln Gly Gly Gln Gly Gly Gln Gly Gly Gly Tyr
    690                 695                 700

Gly Gln Gly Ala Gly Ser Ser Ala Ala Ala Ala Ala Ala Ala
705                 710                 715                 720

Ala Ala Ala Ala Ala Gly Gln Gly Gln Gly Gly Tyr Gly Gln Gly Ala
            725                 730                 735

Gly Gly Asn Ala Ala Ala Ala Ala Ala Ala Ala Ala Ala Ala
        740                 745                 750

Gly Gln Gly Gly Gln Gly Gly Gln Gly Gly Leu Gly Gln Gly Gly Tyr
    755                 760                 765

Gly Gln Gly Ala Gly Ser Ser Ala Ala Ala Ala Ala Ala Ala Ala
770                 775                 780
```

Ala Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala
            805             810                 815

Gly Gln Gly Gly Gln Gly Gly Gln Gly Gly Leu Gly Gln Gly Gly Tyr
        820                 825                 830

Gly Gln Gly Ala Gly Ser Ser Ala Ala Ala Ala Ala Ala Ala Ala
        835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ser
865             870             875             880

Gly Gln Gly Ser Gln Gly Gly Gln Gly Gly Gln Gly Gly Tyr
            885             890             895

Gly Gln Gly Ala Gly Ser Ser Ala Ala Ala Ala Ala Ala Ala
            900             905             910

Ala Ala Ala Ala Ser Gly Arg Gly Gln Gly Gly Tyr Gly Gln Gly Ala
            915             920             925

Gly Gly Asn Ala Ala Ala Ala Ala Ala Ala Ala Ala Ala Ala
            930             935             940

Ala Gly Gln Gly Gly Gln Gly Gly Tyr Gly Gly Leu Gly Gln Gly Gly
945             950             955             960

Tyr Gly Gln Gly Ala Gly Ser Ser Ala Ala Ala Ala Ala Ala Ala
                965             970             975

Ala Ala Ala Ala Gly Gly Gln Gly Gly Gln Gly Gln Gly Gly Tyr Gly
            980             985             990

Gln Gly Ser Gly Gly Ser Ala Ala Ala Ala Ala Ala Ala Ala Ala
        995             1000                1005

Ala Ala Ala Ala Ala Gly Arg Gly Gln Gly Gly Tyr Gly Gln Gly
    1010            1015            1020

Ser Gly Gly Asn Ala Ala Ala Ala Ala Ala Ala Ala Ala Ala
    1025            1030            1035

Ala Ala Ala Ala Gly Gln Gly Gly Gln Gly Gly Tyr Gly Arg Gln
    1040            1045            1050

Ser Gln Gly Ala Gly Ser Ala Ala Ala Ala Ala Ala Ala Ala
    1055            1060            1065

Ala Ala Ala Ala Ala Gly Ser Gly Gln Gly Gly Tyr Gly Gly Gln
    1070            1075            1080

Gly Gln Gly Gly Tyr Gly Gln Ser Ser Ala Ser Ala Ser Ala Ala
    1085            1090            1095

Ala Ser Ala Ala Ser Thr Val Ala Asn Ser Val Ser Arg Leu Ser
    1100            1105            1110

Ser Pro Ser Ala Val Ser Arg Val Ser Ser Ala Val Ser Ser Leu
    1115            1120            1125

Val Ser Asn Gly Gln Val Asn Met Ala Ala Leu Pro Asn Ile Ile
    1130            1135            1140

Ser Asn Ile Ser Ser Ser Val Ser Ala Ser Ala Pro Gly Ala Ser
    1145            1150            1155

Gly Cys Glu Val Ile Val Gln Ala Leu Leu Glu Val Ile Thr Ala
    1160            1165            1170

Leu Val Gln Ile Val Ser Ser Ser Ser Val Gly Tyr Ile Asn Pro
    1175            1180            1185

Ser Ala Val Asn Gln Ile Thr Asn Val Val Ala Asn Ala Met Ala

-continued

```
                    1190                1195                1200

Gln Val  Met Gly
    1205

<210> SEQ ID NO 3
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
```

```
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
```

-continued

```
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 3

Gln Gly Ala Gly Gly Asn Ala Ala Ala Ala Ala Ala Ala Ala
 1               5                  10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
        35                  40                  45

Ala Ala Ala Ala Ala Ala Ala Gly Arg Gly Gln Gly Gly Tyr Gly
    50                  55                  60

Gln Gly Ser Gly Gly Asn Ala Ala Ala Ala Ala Ala Ala Ala
65                  70                  75                  80

Ala Ala Ser Gly Gln Gly Gly Gln Gly Gln Gly Gln Gly Gln
            85                  90                  95

Gly Gly Tyr Gly Gln Gly Ala Gly Ser Ser Ala Ala Ala Ala Ala
        100                 105                 110

Ala Ala Ala Ala Ala Ala Ala Gly Gln Gly Gln Gly Arg Tyr Gly
    115                 120                 125
```

```
Gln Gly Ala Gly Gly Asn Ala Ala Ala Ala Ala Ala Ala
        130                 135                 140
Ala Ala Ala Gly Gln Gly Gly Gln Gly Gly Gln Gly Leu Gly Gln
145                 150                 155                 160
Gly Gly Tyr Gly Gln Gly Ala Gly Ser Ser Ala Ala Ala Ala Ala
            165                 170                 175
Ser Ala Ala Ala Ala Ala Ala Gly Arg Gly Gln Gly Gly Tyr Gly Gln
        180                 185                 190
Gly Ala Gly Gly Asn Ala Ala Ala Ala Ala Ala Ala Ala
        195                 200                 205
Ala Ala Ala Gly Gln Gly Gly Gln Gly Gly Tyr Gly Gly Leu Gly Gln
        210                 215                 220
Gly Gly Tyr Gly Gln Gly Ala Gly Ser Ser Ala Ala Ala Ala Ala
225                 230                 235                 240
Ala Ala Ala Ala Ala Ala Ala Gly Gly Gln Gly Gly Gln Gly Gln Gly
                245                 250                 255
Arg Tyr Gly Gln Gly Ala Gly Ser Ser Ala Ala Ala Ala Ala Ala
            260                 265                 270
Ala Ala Ala Ala Ala Ala Ala Gly Gln Gly Gly Tyr Gly Gln
        275                 280                 285
Gly Ala Gly Gly Asn Ala Ala Ala Ala Ala Ala Ala Ala Ala
        290                 295                 300
Ala Ala Gly Gln Gly Gly Gln Gly Gly Gln Gly Gly Leu Gly Gln Gly
305                 310                 315                 320
Gly Tyr Gly Gln Gly Ala Gly Ser Ser Ala Ala Ala Ala Ala Ala
            325                 330                 335
Ala Ala Ala Ala Ala Ala Gly Arg Gly Gln Gly Gly Tyr Gly Gln Gly
                340                 345                 350
Ala Gly Gly Asn Ala Ala Ala Ala Ala Ala Ala Glu Ala Ala
        355                 360                 365
Ala Ala Gly Gln Gly Gly Gln Gly Gly Tyr Gly Gly Leu Gly Gln Gly
        370                 375                 380
Gly Tyr Gly Gln Gly Ala Gly Ser Ser Ala Ala Ala Ala Ala Ala
385                 390                 395                 400
Ala Ala Ala Ala Ala Ala Gly Arg Gly Gln Gly Gly Tyr Gly Gln Gly
                405                 410                 415
Ala Gly Gly Asn Ala Ala Ala Ala Ala Ala Ala Ala Ala Ala
        420                 425                 430
Ala Ala Gly Gln Gly Gly Gln Gly Gly Tyr Gly Gly Leu Gly Gln Gly
        435                 440                 445
Gly Tyr Gly Gln Gly Ala Gly Ser Ser Ala Ala Ala Ala Ala Ala
        450                 455                 460
Ala Ala Ala Ala Ala Ala Gly Gly Gln Gly Gly Gln Gly Gln Gly Arg
465                 470                 475                 480
Tyr Gly Gln Gly Ala Gly Ser Ser Ala Ala Ala Ala Ala Ala
            485                 490                 495
Ala Ala Ala Ala Ala Ala Gly Arg Gly Gln Gly Gly Tyr Gly Gln Gly
                500                 505                 510
Ser Gly Gly Asn Ala Ala Ala Ala Ala Ala Ala Ala Ala Ala
        515                 520                 525
Ser Gly Gln Gly Ser Gln Gly Gly Gln Gly Gln Gly Gln Gly Gly
        530                 535                 540
Tyr Gly Gln Gly Ala Gly Ser Ser Ala Ala Ala Ala Ala Ala Ala Ala
```

```
                   545                 550                 555                 560
Ala Ala Ala Ala Ala Ser Gly Arg Gly Gln Gly Gly Tyr Gly Gln Gly
                565                 570                 575
Ala Gly Gly Asn Ala Ala Ala Ala Ala Ala Ala Ala Ala Ala Ala Ala
                580                 585                 590
Ala Ala Gly Gln Gly Gly Gln Gly Gly Tyr Gly Gly Leu Gly Gln Gly
                595                 600                 605
Gly Tyr Gly Gln Gly Ala Gly Ser Ser Ala Ala Ala Ala Ala Ala Ala
            610                 615                 620
Ala Ala Ala Ala Ala Gly Gly Gln Gly Gly Gln Gly Gln Gly Gly Tyr
625                 630                 635                 640
Gly Gln Gly Ala Gly Ser Ser Ala Ala Ala Ala Ala Ala Ala Ala Ala
                645                 650                 655
Ala Ala Ala Ala Ala Gly Arg Gly Gln Gly Gly Tyr Gly Gln Gly Ser
                660                 665                 670
Gly Gly Asn Ala Ala Ala Ala Ala Ala Ala Ala Ala Ala Ala Ala Ser
            675                 680                 685
Gly Gln Gly Gly Gln Gly Gly Gln Gly Gly Gln Gly Gly Gly Gly Tyr
            690                 695                 700
Gly Gln Gly Ala Gly Ser Ser Ala Ala Ala Ala Ala Ala Ala Ala Ala
705                 710                 715                 720
Ala Ala Ala Ala Ala Gly Gln Gly Gln Gly Gly Tyr Gly Gln Gly Ala
                725                 730                 735
Gly Gly Asn Ala Ala Ala Ala Ala Ala Ala Ala Ala Ala Ala Ala Ala
                740                 745                 750
Gly Gln Gly Gly Gln Gly Gly Gln Gly Gly Leu Gly Gln Gly Gly Tyr
                755                 760                 765
Gly Gln Gly Ala Gly Ser Ser Ala Ala Ala Ala Ala Ala Ala Ala Ala
            770                 775                 780
Ala Ala Ala Ala Ala Gly Arg Gly Gln Gly Gly Tyr Gly Gln Gly Val
785                 790                 795                 800
Gly Gly Asn Ala Ala Ala Ala Ala Ala Ala Ala Ala Ala Ala Ala Ala
                805                 810                 815
Gly Gln Gly Gly Gln Gly Gly Gln Gly Gly Leu Gly Gln Gly Gly Tyr
                820                 825                 830
Gly Gln Gly Ala Gly Ser Ser Ala Ala Ala Ala Ala Ala Ala Ala Ala
            835                 840                 845
Ala Ala Ala Ala Ala Gly Arg Gly Gln Gly Gly Tyr Gly Gln Gly Ser
            850                 855                 860
Gly Gly Asn Ala Ala Ala Ala Ala Ala Ala Ala Ala Ala Ala Ala Ser
865                 870                 875                 880
Gly Gln Gly Ser Gln Gly Gly Gln Gly Gly Gln Gly Gly Gly Gly Tyr
                885                 890                 895
Gly Gln Gly Ala Gly Ser Ser Ala Ala Ala Ala Ala Ala Ala Ala Ala
            900                 905                 910
Ala Ala Ala Ala Ser Gly Arg Gly Gln Gly Gly Tyr Gly Gln Gly Ala
            915                 920                 925
Gly Gly Asn Ala Ala Ala Ala Ala Ala Ala Ala Ala Ala Ala Ala Ala
            930                 935                 940
Ala Gly Gln Gly Gly Gln Gly Gly Tyr Gly Gly Leu Gly Gln Gly Gly
945                 950                 955                 960
Tyr Gly Gln Gly Ala Gly Ser Ser Ala Ala Ala Ala Ala Ala Ala Ala
                965                 970                 975
```

-continued

```
Ala Ala Ala Ala Gly Gly Gln Gly Gly Gln Gly Gln Gly Gly Tyr Gly
            980                 985                 990

Gln Gly Ser Gly Gly Ser Ala Ala  Ala Ala Ala  Ala Ala Ala
        995                 1000                1005

Ala Ala  Ala Ala Ala Gly Arg  Gly Gln Gly Gly Tyr  Gly Gln Gly
    1010                1015                1020

Ser Gly  Gly Asn Ala Ala Ala  Ala Ala Ala Ala  Ala Ala Ala
    1025                1030                1035

Ala Ala  Ala Ala Gly Gln Gly  Gly Gln Gly Gly Tyr  Gly Arg Gln
    1040                1045                1050

Ser Gln  Gly Ala Gly Ser Ala  Ala Ala Ala Ala  Ala Ala Ala
    1055                1060                1065

Ala Ala  Ala Ala Ala Gly Ser  Gly Gln Gly Gly Tyr  Gly Gly Gln
    1070                1075                1080

Gly Gln  Gly Gly Tyr Gly Gln  Ser Ser Ala Ser Ala  Ser Ala Ala
    1085                1090                1095

Ala Ser  Ala Ala Ser Thr Val  Ala Asn Ser Val Ser
    1100                1105                1110

<210> SEQ ID NO 4
<211> LENGTH: 97
<212> TYPE: PRT
<213> ORGANISM: Euprosthenops australis

<400> SEQUENCE: 4

Arg Leu Ser Ser Pro Ser Ala Val Ser Arg Val Ser Ser Ala Val Ser
1               5                   10                  15

Ser Leu Val Ser Asn Gly Gln Val Asn Met Ala Ala Leu Pro Asn Ile
            20                  25                  30

Ile Ser Asn Ile Ser Ser Ser Val Ser Ala Ser Ala Pro Gly Ala Ser
        35                  40                  45

Gly Cys Glu Val Ile Val Gln Ala Leu Leu Glu Val Ile Thr Ala Leu
    50                  55                  60

Val Gln Ile Val Ser Ser Ser Val Gly Tyr Ile Asn Pro Ser Ala
65                  70                  75                  80

Val Asn Gln Ile Thr Asn Val Val Ala Asn Ala Met Ala Gln Val Met
                85                  90                  95

Gly

<210> SEQ ID NO 5
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 5

Gly Gln Gly Gly Gln Gly Gly Gln Gly Gly Leu Gly Gln Gly Gly Tyr
1               5                   10                  15
```

```
Gly Gln Gly Ala Gly Ser Ser
            20

<210> SEQ ID NO 6
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 6

Gly Gln Gly Gly Gln Gly Gln Gly Gly Tyr Gly Gln Gly Ala Gly Ser
1               5                   10                  15

Ser

<210> SEQ ID NO 7
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 7

Gly Arg Gly Gln Gly Gly Tyr Gly Gln Gly Ala Gly Gly Asn
1               5                   10

<210> SEQ ID NO 8
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu
```

-continued

```
<400> SEQUENCE: 8

Ser Arg Leu Ser Ser Pro Gln Ala Ser Ser Arg Val Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ala Ser Asn Pro Gly Leu
            35                  40                  45

Ser Gly Cys Asp Val Leu Val Gln Ala Leu Leu Glu Val Val Ser Ala
        50                  55                  60

Leu Val His Ile Leu Gly Ser Ser Ser Ile Gly Gln Val Asn Tyr Gly
65                  70                  75                  80

Ser Ala Gly Gln Ala Thr Gln Ile Val Gly Gln Ser Val Ala Gln Ala
                85                  90                  95

Leu Gly Glu Phe
            100

<210> SEQ ID NO 9
<211> LENGTH: 269
<212> TYPE: PRT
<213> ORGANISM: Artificial Sequence
<220> FEATURE:
<223> OTHER INFORMATION: Sequence derived from Euprosthenops australis
      MaSp1
<220> FEATURE:
<221> NAME/KEY: DOMAIN
<222> LOCATION: (1)..(171)
<223> OTHER INFORMATION: Repetitive fragment
<220> FEATURE:
<221> NAME/KEY: REPEAT
<222> LOCATION: (11)..(30)
<220> FEATURE:
<221> NAME/KEY: REPEAT
<222> LOCATION: (31)..(42)
<220> FEATURE:
<221> NAME/KEY: REPEAT
<222> LOCATION: (43)..(60)
<220> FEATURE:
<221> NAME/KEY: REPEAT
<222> LOCATION: (61)..(75)
<220> FEATURE:
<221> NAME/KEY: REPEAT
<222> LOCATION: (76)..(89)
<220> FEATURE:
<221> NAME/KEY: REPEAT
<222> LOCATION: (90)..(104)
<220> FEATURE:
<221> NAME/KEY: REPEAT
<222> LOCATION: (105)..(121)
<220> FEATURE:
<221> NAME/KEY: REPEAT
<222> LOCATION: (122)..(135)
<220> FEATURE:
<221> NAME/KEY: REPEAT
<222> LOCATION: (136)..(152)
<220> FEATURE:
<221> NAME/KEY: REPEAT
<222> LOCATION: (153)..(171)
<220> FEATURE:
<221> NAME/KEY: DOMAIN
<222> LOCATION: (172)..(269)
<223> OTHER INFORMATION: C-terminal fragment

<400> SEQUENCE: 9

Gly Ser Ala Met Gly Tyr Leu Trp Ile Gln Gly Gln Gly Tyr Gly
1               5                   10                  15

Gly Leu Gly Gln Gly Gly Tyr Gly Gln Gly Ala Gly Ser Ser Ala Ala
                20                  25                  30

Ala Ala Ala Ala Ala Ala Ala Ala Ala Ala Gly Gly Gln Gly Gly Gln
            35                  40                  45
```

Gly Gln Gly Gly Tyr Gly Gln Gly Ser Gly Gly Ser Ala Ala Ala Ala
            50                  55                  60

Ala Ala Ala Ala Ala Ala Ala Ala Ala Ala Gly Arg Gly Gln Gly
65                  70                  75                  80

Gly Tyr Gly Gln Gly Ser Gly Gly Asn Ala Ala Ala Ala Ala Ala
                85                  90                  95

Ala Ala Ala Ala Ala Ala Ala Gly Gln Gly Gly Gln Gly Gly Tyr
            100                 105                 110

Gly Arg Gln Ser Gln Gly Ala Gly Ser Ala Ala Ala Ala Ala Ala
            115                 120                 125

Ala Ala Ala Ala Ala Ala Gly Ser Gly Gln Gly Gly Tyr Gly Gly
            130                 135                 140

Gln Gly Gln Gly Gly Tyr Gly Gln Ser Ala Ser Ala Ser Ala Ala
145                 150                 155                 160

Ala Ser Ala Ala Ser Thr Val Ala Asn Ser Val Ser Arg Leu Ser Ser
                165                 170                 175

Pro Ser Ala Val Ser Arg Val Ser Ser Ala Val Ser Ser Leu Val Ser
                180                 185                 190

Asn Gly Gln Val Asn Met Ala Ala Leu Pro Asn Ile Ile Ser Asn Ile
            195                 200                 205

Ser Ser Ser Val Ser Ala Ser Ala Pro Gly Ala Ser Gly Cys Glu Val
210                 215                 220

Ile Val Gln Ala Leu Leu Glu Val Ile Thr Ala Leu Val Gln Ile Val
225                 230                 235                 240

Ser Ser Ser Ser Val Gly Tyr Ile Asn Pro Ser Ala Val Asn Gln Ile
                245                 250                 255

Thr Asn Val Val Ala Asn Ala Met Ala Gln Val Met Gly
            260                 265

<210> SEQ ID NO 10
<211> LENGTH: 126
<212> TYPE: PRT
<213> ORGANISM: Euprosthenops australis

<400> SEQUENCE: 10

Gly Ser Ala Met Gly Gln Gly Ser Gly Gly Asn Ala Ala Ala Ala Ala
1               5                   10                  15

Ala Ala Ala Ala Ala Ala Ala Ser Gly Gln Gly Gly Gln Gly Gly
            20                  25                  30

Gln Gly Gln Gly Gly Tyr Gly Gln Gly Ala Gly Ile Ser Ala Ala Ala
            35                  40                  45

Ala Ala Ala Ala Ala Ala Ala Gly Ala Ala Ala Gly Arg Gly Gln
            50                  55                  60

Gly Gly Tyr Gly Gln Gly Ala Gly Asn Ala Ala Ala Ala Ala
65                  70                  75                  80

Ala Ala Ala Ala Ala Ala Ala Gly Gln Gly Gln Gly Gln Gly Tyr
                85                  90                  95

Gly Gly Gln Gly Leu Gly Gly Tyr Gly Gln Gly Ala Gly Ser Ser Ala
            100                 105                 110

Ala Ala Ala Ala Ala Ala Ala Gly Arg Gly Gln Ser Val Tyr
            115                 120                 125

<210> SEQ ID NO 11
<211> LENGTH: 152
<212> TYPE: PRT
<213> ORGANISM: Artificial Sequence

```
<220> FEATURE:
<223> OTHER INFORMATION: Hybrid sequence derived from Euprosthenops
      australis and Euprosthenops sp MaSp1

<400> SEQUENCE: 11

Gly Ser Ala Met Gly Gly Ala Gly Gln Gly Gly Tyr Gly Gly Leu Gly
1               5                   10                  15

Gly Gln Gly Ala Gly Arg Gly Gly Gln Gly Ala Gly Ala Ala Ala Ala
            20                  25                  30

Ala Ala Gly Gly Ser Gly Gln Gly Gly Tyr Gly Gly Val Gly Ser Gly
        35                  40                  45

Ala Ser Ala Ala Ser Ala Ala Ser Arg Leu Ser Ser Pro Glu Ala
    50                  55                  60

Ser Ser Arg Val Ser Ser Ala Val Ser Asn Leu Val Ser Ser Gly Pro
65                  70                  75                  80

Thr Asn Ser Ala Ala Leu Ser Ser Thr Ile Ser Asn Val Val Ser Gln
                85                  90                  95

Ile Gly Ala Ser Asn Pro Gly Leu Ser Gly Cys Asp Val Leu Val Gln
            100                 105                 110

Ala Leu Leu Glu Val Val Ser Ala Leu Ile His Ile Leu Gly Ser Ser
        115                 120                 125

Ser Ile Gly Gln Val Asn Tyr Gly Ser Ala Gly Gln Ala Thr Gln Leu
    130                 135                 140

Val Gly Gln Ser Val Tyr Gln Ala
145                 150

<210> SEQ ID NO 12
<211> LENGTH: 257
<212> TYPE: PRT
<213> ORGANISM: Artificial Sequence
<220> FEATURE:
<223> OTHER INFORMATION: Hybrid sequence derived from Euprosthenops
      australis and Euprosthenops sp MaSp1

<400> SEQUENCE: 12

Gly Ser Ala Met Ala Ser Gly Gln Gly Gly Gln Gly Gly Gln Gly Gln
1               5                   10                  15

Gly Gly Tyr Gly Gln Gly Ala Gly Ile Ser Ala Ala Ala Ala Ala Ala
            20                  25                  30

Ala Ala Ala Ala Ala Gly Ala Ala Gly Arg Gly Gln Gly Gly Tyr
        35                  40                  45

Gly Gln Gly Ala Gly Gly Asn Ala Ala Ala Ala Ala Ala Ala
    50                  55                  60

Ala Ala Ala Ala Ala Gly Gln Gly Gly Gln Gly Gly Tyr Gly Gly Gln
65                  70                  75                  80

Gly Leu Gly Gly Tyr Gly Gln Gly Ala Gly Ser Ala Ala Ala Ala
                85                  90                  95

Ala Ala Ala Ala Gly Arg Gly Gln Ser Val Tyr Ala Ser Gly Gly Ala
            100                 105                 110

Gly Gln Gly Gly Tyr Gly Gly Leu Gly Gly Gln Gly Ala Gly Arg Gly
        115                 120                 125

Gly Gln Gly Ala Gly Ala Ala Ala Ala Ala Gly Gly Ser Gly Gln
    130                 135                 140

Gly Gly Tyr Gly Gly Val Gly Ser Gly Ala Ser Ala Ala Ser Ala Ala
145                 150                 155                 160

Ala Ser Arg Leu Ser Ser Pro Glu Ala Ser Ser Arg Val Ser Ser Ala
                165                 170                 175
```

```
Val Ser Asn Leu Val Ser Ser Gly Pro Thr Asn Ser Ala Ala Leu Ser
            180                 185                 190

Ser Thr Ile Ser Asn Val Val Ser Gln Ile Gly Ala Ser Asn Pro Gly
        195                 200                 205

Leu Ser Gly Cys Asp Val Leu Val Gln Ala Leu Leu Glu Val Val Ser
    210                 215                 220

Ala Leu Ile His Ile Leu Gly Ser Ser Ile Gly Gln Val Asn Tyr
225                 230                 235                 240

Gly Ser Ala Gly Gln Ala Thr Gln Leu Val Gly Gln Ser Val Tyr Gln
                245                 250                 255

Ala

<210> SEQ ID NO 13
<211> LENGTH: 276
<212> TYPE: PRT
<213> ORGANISM: Artificial Sequence
<220> FEATURE:
<223> OTHER INFORMATION: Hybrid sequence derived from Euprosthenops
      australis and Euprosthenops sp MaSp1
<220> FEATURE:
<221> NAME/KEY: REPEAT
<222> LOCATION: (1)..(11)
<220> FEATURE:
<221> NAME/KEY: DOMAIN
<222> LOCATION: (1)..(180)
<223> OTHER INFORMATION: Repetitive fragment
<220> FEATURE:
<221> NAME/KEY: REPEAT
<222> LOCATION: (12)..(25)
<220> FEATURE:
<221> NAME/KEY: REPEAT
<222> LOCATION: (26)..(45)
<220> FEATURE:
<221> NAME/KEY: REPEAT
<222> LOCATION: (46)..(60)
<220> FEATURE:
<221> NAME/KEY: REPEAT
<222> LOCATION: (61)..(74)
<220> FEATURE:
<221> NAME/KEY: REPEAT
<222> LOCATION: (75)..(88)
<220> FEATURE:
<221> NAME/KEY: REPEAT
<222> LOCATION: (89)..(111)
<220> FEATURE:
<221> NAME/KEY: REPEAT
<222> LOCATION: (112)..(119)
<220> FEATURE:
<221> NAME/KEY: REPEAT
<222> LOCATION: (120)..(149)
<220> FEATURE:
<221> NAME/KEY: REPEAT
<222> LOCATION: (150)..(158)
<220> FEATURE:
<221> NAME/KEY: REPEAT
<222> LOCATION: (159)..(172)
<220> FEATURE:
<221> NAME/KEY: REPEAT
<222> LOCATION: (173)..(180)
<220> FEATURE:
<221> NAME/KEY: DOMAIN
<222> LOCATION: (181)..(276)
<223> OTHER INFORMATION: C-terminal fragment

<400> SEQUENCE: 13

Gly Ser Ala Met Gly Gln Gly Ser Gly Gly Asn Ala Ala Ala Ala Ala
1               5                   10                  15

Ala Ala Ala Ala Ala Ala Ala Ala Ser Gly Gln Gly Gly Gln Gly Gly
            20                  25                  30

Gln Gly Gln Gly Gly Tyr Gly Gln Gly Ala Gly Ile Ser Ala Ala Ala
        35                  40                  45
```

```
Ala Ala Ala Ala Ala Ala Gly Ala Ala Gly Arg Gly Gln
    50              55                  60

Gly Gly Tyr Gly Gln Gly Ala Gly Asn Ala Ala Ala Ala Ala Ala
65              70                  75                  80

Ala Ala Ala Ala Ala Ala Ala Gly Gln Gly Gln Gly Tyr
            85                  90                  95

Gly Gly Gln Gly Leu Gly Gly Tyr Gly Gln Gly Ala Gly Ser Ser Ala
                100                 105                 110

Ala Ala Ala Ala Ala Ala Gly Arg Gly Gln Ser Val Tyr Ala Ser
            115                 120                 125

Gly Gly Ala Gly Gln Gly Gly Tyr Gly Gly Leu Gly Gly Gln Gly Ala
            130                 135                 140

Gly Arg Gly Gly Gln Gly Ala Gly Ala Ala Ala Ala Ala Gly Gly
145                 150                 155                 160

Ser Gly Gln Gly Gly Tyr Gly Gly Val Gly Ser Gly Ala Ser Ala Ala
                165                 170                 175

Ser Ala Ala Ala Ser Arg Leu Ser Ser Pro Glu Ala Ser Ser Arg Val
            180                 185                 190

Ser Ser Ala Val Ser Asn Leu Val Ser Ser Gly Pro Thr Asn Ser Ala
            195                 200                 205

Ala Leu Ser Ser Thr Ile Ser Asn Val Val Ser Gln Ile Gly Ala Ser
    210                 215                 220

Asn Pro Gly Leu Ser Gly Cys Asp Val Leu Val Gln Ala Leu Leu Glu
225                 230                 235                 240

Val Val Ser Ala Leu Ile His Ile Leu Gly Ser Ser Ile Gly Gln
            245                 250                 255

Val Asn Tyr Gly Ser Ala Gly Gln Ala Thr Gln Leu Val Gly Gln Ser
    260                 265                 270

Val Tyr Gln Ala
        275

<210> SEQ ID NO 14
<211> LENGTH: 269
<212> TYPE: PRT
<213> ORGANISM: Artificial Sequence
<220> FEATURE:
<223> OTHER INFORMATION: Sequence derived from Euprosthenops australis
      MaSp1
<220> FEATURE:
<221> NAME/KEY: DOMAIN
<222> LOCATION: (1)..(171)
<223> OTHER INFORMATION: Repetitive fragment
<220> FEATURE:
<221> NAME/KEY: REPEAT
<222> LOCATION: (11)..(30)
<220> FEATURE:
<221> NAME/KEY: REPEAT
<222> LOCATION: (31)..(42)
<220> FEATURE:
<221> NAME/KEY: MUTAGEN
<222> LOCATION: (36)..(37)
<220> FEATURE:
<221> NAME/KEY: REPEAT
<222> LOCATION: (43)..(60)
<220> FEATURE:
<221> NAME/KEY: REPEAT
<222> LOCATION: (61)..(75)
<220> FEATURE:
<221> NAME/KEY: REPEAT
<222> LOCATION: (76)..(89)
<220> FEATURE:
<221> NAME/KEY: REPEAT
<222> LOCATION: (90)..(104)
<220> FEATURE:
```

```
<221> NAME/KEY: REPEAT
<222> LOCATION: (105)..(121)
<220> FEATURE:
<221> NAME/KEY: REPEAT
<222> LOCATION: (122)..(135)
<220> FEATURE:
<221> NAME/KEY: REPEAT
<222> LOCATION: (136)..(152)
<220> FEATURE:
<221> NAME/KEY: REPEAT
<222> LOCATION: (153)..(171)
<220> FEATURE:
<221> NAME/KEY: DOMAIN
<222> LOCATION: (172)..(269)
<223> OTHER INFORMATION: C-terminal fragment
<220> FEATURE:
<221> NAME/KEY: DOMAIN
<222> LOCATION: (172)..(269)
<223> OTHER INFORMATION: C-terminal fragment

<400> SEQUENCE: 14
```

Gly Ser Ala Met Gly Tyr Leu Trp Ile Gln Gly Gln Gly Gly Tyr Gly
1               5                   10                  15

Gly Leu Gly Gln Gly Gly Tyr Gly Gln Gly Ala Gly Ser Ser Ala Ala
            20                  25                  30

Ala Ala Ala Cys Cys Ala Ala Ala Ala Gly Gly Gln Gly Gly Gln
        35                  40                  45

Gly Gln Gly Gly Tyr Gly Gln Gly Ser Gly Ser Ala Ala Ala Ala
    50                  55                  60

Ala Ala Ala Ala Ala Ala Ala Ala Ala Gly Arg Gly Gln Gly
65                  70                  75                  80

Gly Tyr Gly Gln Gly Ser Gly Gly Asn Ala Ala Ala Ala Ala
            85                  90                  95

Ala Ala Ala Ala Ala Ala Ala Gly Gln Gly Gln Gly Gly Tyr
            100                 105                 110

Gly Arg Gln Ser Gln Gly Ala Gly Ser Ala Ala Ala Ala Ala Ala
            115                 120                 125

Ala Ala Ala Ala Ala Ala Ala Gly Ser Gly Gln Gly Gly Tyr Gly Gly
            130                 135                 140

Gln Gly Gln Gly Gly Tyr Gly Gln Ser Ser Ala Ser Ala Ser Ala Ala
145                 150                 155                 160

Ala Ser Ala Ala Ser Thr Val Ala Asn Ser Val Ser Arg Leu Ser Ser
                165                 170                 175

Pro Ser Ala Val Ser Arg Val Ser Ser Ala Val Ser Ser Leu Val Ser
            180                 185                 190

Asn Gly Gln Val Asn Met Ala Ala Leu Pro Asn Ile Ile Ser Asn Ile
            195                 200                 205

Ser Ser Ser Val Ser Ala Ser Ala Pro Gly Ala Ser Gly Cys Glu Val
        210                 215                 220

Ile Val Gln Ala Leu Leu Glu Val Ile Thr Ala Leu Val Gln Ile Val
225                 230                 235                 240

Ser Ser Ser Ser Val Gly Tyr Ile Asn Pro Ser Ala Val Asn Gln Ile
                245                 250                 255

Thr Asn Val Val Ala Asn Ala Met Ala Gln Val Met Gly
            260                 265

```
<210> SEQ ID NO 15
<211> LENGTH: 269
<212> TYPE: PRT
<213> ORGANISM: Artificial Sequence
<220> FEATURE:
<223> OTHER INFORMATION: Sequence derived from Euprosthenops australis
```

```
              MaSp1
<220> FEATURE:
<221> NAME/KEY: DOMAIN
<222> LOCATION: (1)..(171)
<223> OTHER INFORMATION: Repetitive fragment
<220> FEATURE:
<221> NAME/KEY: REPEAT
<222> LOCATION: (11)..(30)
<220> FEATURE:
<221> NAME/KEY: REPEAT
<222> LOCATION: (31)..(42)
<220> FEATURE:
<221> NAME/KEY: REPEAT
<222> LOCATION: (43)..(60)
<220> FEATURE:
<221> NAME/KEY: REPEAT
<222> LOCATION: (61)..(75)
<220> FEATURE:
<221> NAME/KEY: REPEAT
<222> LOCATION: (76)..(89)
<220> FEATURE:
<221> NAME/KEY: REPEAT
<222> LOCATION: (90)..(104)
<220> FEATURE:
<221> NAME/KEY: REPEAT
<222> LOCATION: (105)..(121)
<220> FEATURE:
<221> NAME/KEY: REPEAT
<222> LOCATION: (122)..(135)
<220> FEATURE:
<221> NAME/KEY: MUTAGEN
<222> LOCATION: (128)..(129)
<220> FEATURE:
<221> NAME/KEY: REPEAT
<222> LOCATION: (136)..(152)
<220> FEATURE:
<221> NAME/KEY: REPEAT
<222> LOCATION: (153)..(171)
<220> FEATURE:
<221> NAME/KEY: DOMAIN
<222> LOCATION: (172)..(269)
<223> OTHER INFORMATION: C-terminal fragment

<400> SEQUENCE: 15

Gly Ser Ala Met Gly Tyr Leu Trp Ile Gln Gly Gln Gly Gly Tyr Gly
1               5                   10                  15

Gly Leu Gly Gln Gly Gly Tyr Gly Gln Gly Ala Gly Ser Ser Ala Ala
            20                  25                  30

Ala Ala Ala Ala Ala Ala Ala Ala Ala Gly Gly Gln Gly Gly Gln
        35                  40                  45

Gly Gln Gly Gly Tyr Gly Gln Gly Ser Gly Gly Ser Ala Ala Ala
    50                  55                  60

Ala Ala Ala Ala Ala Ala Ala Ala Gly Arg Gly Gln Gly
65                  70                  75                  80

Gly Tyr Gly Gln Gly Ser Gly Gly Asn Ala Ala Ala Ala Ala
            85                  90                  95

Ala Ala Ala Ala Ala Ala Ala Gly Gln Gly Gly Gln Gly Gly Tyr
            100                 105                 110

Gly Arg Gln Ser Gln Gly Ala Gly Ser Ala Ala Ala Ala Ala Cys
        115                 120                 125

Cys Ala Ala Ala Ala Ala Gly Ser Gly Gln Gly Gly Tyr Gly Gly
    130                 135                 140

Gln Gly Gln Gly Gly Tyr Gly Gln Ser Ser Ala Ser Ala Ser Ala Ala
145                 150                 155                 160

Ala Ser Ala Ala Ser Thr Val Ala Asn Ser Val Ser Arg Leu Ser Ser
                165                 170                 175

Pro Ser Ala Val Ser Arg Val Ser Ala Val Ser Ser Leu Val Ser
            180                 185                 190
```

```
Asn Gly Gln Val Asn Met Ala Ala Leu Pro Asn Ile Ile Ser Asn Ile
            195                 200                 205

Ser Ser Ser Val Ser Ala Ser Ala Pro Gly Ala Ser Gly Cys Glu Val
            210                 215                 220

Ile Val Gln Ala Leu Leu Glu Val Ile Thr Ala Leu Val Gln Ile Val
225                 230                 235                 240

Ser Ser Ser Ser Val Gly Tyr Ile Asn Pro Ser Ala Val Asn Gln Ile
            245                 250                 255

Thr Asn Val Val Ala Asn Ala Met Ala Gln Val Met Gly
            260                 265

<210> SEQ ID NO 16
<211> LENGTH: 269
<212> TYPE: PRT
<213> ORGANISM: Artificial Sequence
<220> FEATURE:
<223> OTHER INFORMATION: Sequence derived from Euprosthenops australis
      MaSp1
<220> FEATURE:
<221> NAME/KEY: DOMAIN
<222> LOCATION: (1)..(171)
<223> OTHER INFORMATION: Repetitive fragment
<220> FEATURE:
<221> NAME/KEY: REPEAT
<222> LOCATION: (11)..(30)
<220> FEATURE:
<221> NAME/KEY: REPEAT
<222> LOCATION: (31)..(42)
<220> FEATURE:
<221> NAME/KEY: REPEAT
<222> LOCATION: (43)..(60)
<220> FEATURE:
<221> NAME/KEY: REPEAT
<222> LOCATION: (61)..(75)
<220> FEATURE:
<221> NAME/KEY: REPEAT
<222> LOCATION: (76)..(89)
<220> FEATURE:
<221> NAME/KEY: REPEAT
<222> LOCATION: (90)..(104)
<220> FEATURE:
<221> NAME/KEY: REPEAT
<222> LOCATION: (105)..(121)
<220> FEATURE:
<221> NAME/KEY: REPEAT
<222> LOCATION: (122)..(135)
<220> FEATURE:
<221> NAME/KEY: REPEAT
<222> LOCATION: (136)..(152)
<220> FEATURE:
<221> NAME/KEY: REPEAT
<222> LOCATION: (153)..(171)
<220> FEATURE:
<221> NAME/KEY: DOMAIN
<222> LOCATION: (172)..(269)
<223> OTHER INFORMATION: C-terminal fragment
<220> FEATURE:
<221> NAME/KEY: MUTAGEN
<222> LOCATION: (222)..(222)

<400> SEQUENCE: 16

Gly Ser Ala Met Gly Tyr Leu Trp Ile Gln Gly Gln Gly Gly Tyr Gly
1               5                   10                  15

Gly Leu Gly Gln Gly Gly Tyr Gly Gln Gly Ala Gly Ser Ser Ala Ala
            20                  25                  30

Ala Ala Ala Ala Ala Ala Ala Ala Gly Gly Gln Gly Gly Gln
            35                  40                  45

Gly Gln Gly Gly Tyr Gly Gln Gly Ser Gly Gly Ser Ala Ala Ala Ala
    50                  55                  60
```

```
Ala Ala Ala Ala Ala Ala Ala Ala Gly Arg Gly Gln Gly
 65                  70                  75                  80

Gly Tyr Gly Gln Gly Ser Gly Asn Ala Ala Ala Ala Ala
                 85                  90                  95

Ala Ala Ala Ala Ala Ala Ala Gly Gln Gly Gly Gln Gly Tyr
                100                 105                 110

Gly Arg Gln Ser Gln Gly Ala Gly Ser Ala Ala Ala Ala Ala
            115                 120                 125

Ala Ala Ala Ala Ala Ala Gly Ser Gly Gln Gly Gly Tyr Gly Gly
            130                 135                 140

Gln Gly Gln Gly Gly Tyr Gly Gln Ser Ser Ala Ser Ala Ser Ala Ala
145                 150                 155                 160

Ala Ser Ala Ala Ser Thr Val Ala Asn Ser Val Ser Arg Leu Ser Ser
                165                 170                 175

Pro Ser Ala Val Ser Arg Val Ser Ser Ala Val Ser Ser Leu Val Ser
                180                 185                 190

Asn Gly Gln Val Asn Met Ala Ala Leu Pro Asn Ile Ile Ser Asn Ile
            195                 200                 205

Ser Ser Ser Val Ser Ala Ser Ala Pro Gly Ala Ser Gly Ser Glu Val
    210                 215                 220

Ile Val Gln Ala Leu Leu Glu Val Ile Thr Ala Leu Val Gln Ile Val
225                 230                 235                 240

Ser Ser Ser Ser Val Gly Tyr Ile Asn Pro Ser Ala Val Asn Gln Ile
                245                 250                 255

Thr Asn Val Val Ala Asn Ala Met Ala Gln Val Met Gly
            260                 265
```

<210> SEQ ID NO 17
<211> LENGTH: 384
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(384)
<223> OTHER INFORMATION: Up to 4 of the 48 residue length AG segments may be absent
<220> FEATURE:
<221> NAME/KEY: misc_feature
<222> LOCATION: (1)..(18)
<223> OTHER INFORMATION: Up to 10 residues may be absent
<220> FEATURE:
<221> NAME/KEY: misc_feature
<222> LOCATION: (1)..(18)
<223> OTHER INFORMATION: Up to 3 amino acid residues may be an amino acid other than Ala
<220> FEATURE:
<221> NAME/KEY: misc_feature
<222> LOCATION: (19)..(48)
<223> OTHER INFORMATION: Up to 18 residues may be absent
<220> FEATURE:
<221> NAME/KEY: misc_feature
<222> LOCATION: (19)..(48)
<223> OTHER INFORMATION: At least 4 to 12 of the residues are Gly
<220> FEATURE:
<221> NAME/KEY: misc_feature
<222> LOCATION: (49)..(66)
<223> OTHER INFORMATION: Up to 10 residues may be absent
<220> FEATURE:
<221> NAME/KEY: misc_feature
<222> LOCATION: (49)..(66)
<223> OTHER INFORMATION: Up to 3 amino acid residues may be an amino acid other than Ala
<220> FEATURE:
<221> NAME/KEY: misc_feature
<222> LOCATION: (67)..(96)

```
<223> OTHER INFORMATION: Up to 18 residues may be absent
<220> FEATURE:
<221> NAME/KEY: misc_feature
<222> LOCATION: (67)..(96)
<223> OTHER INFORMATION: At least 4 to 12 of the residues are Gly
<220> FEATURE:
<221> NAME/KEY: misc_feature
<222> LOCATION: (97)..(114)
<223> OTHER INFORMATION: Up to 10 residues may be absent
<220> FEATURE:
<221> NAME/KEY: misc_feature
<222> LOCATION: (97)..(114)
<223> OTHER INFORMATION: Up to 3 amino acid residues may be an amino
      acid other than Ala
<220> FEATURE:
<221> NAME/KEY: misc_feature
<222> LOCATION: (115)..(144)
<223> OTHER INFORMATION: Up to 18 residues may be absent
<220> FEATURE:
<221> NAME/KEY: misc_feature
<222> LOCATION: (115)..(144)
<223> OTHER INFORMATION: At least 4 to 12 of the residues are Gly
<220> FEATURE:
<221> NAME/KEY: misc_feature
<222> LOCATION: (145)..(162)
<223> OTHER INFORMATION: Up to 10 residues may be absent
<220> FEATURE:
<221> NAME/KEY: misc_feature
<222> LOCATION: (145)..(162)
<223> OTHER INFORMATION: Up to 3 amino acid residues may be an amino
      acid other than Ala
<220> FEATURE:
<221> NAME/KEY: misc_feature
<222> LOCATION: (163)..(192)
<223> OTHER INFORMATION: Up to 18 residues may be absent
<220> FEATURE:
<221> NAME/KEY: misc_feature
<222> LOCATION: (163)..(192)
<223> OTHER INFORMATION: At least 4 to 12 of the residues are Gly
<220> FEATURE:
<221> NAME/KEY: misc_feature
<222> LOCATION: (193)..(210)
<223> OTHER INFORMATION: Up to 10 residues may be absent
<220> FEATURE:
<221> NAME/KEY: misc_feature
<222> LOCATION: (193)..(210)
<223> OTHER INFORMATION: Up to 3 amino acid residues may be an amino
      acid other than Ala
<220> FEATURE:
<221> NAME/KEY: misc_feature
<222> LOCATION: (211)..(240)
<223> OTHER INFORMATION: Up to 18 residues may be absent
<220> FEATURE:
<221> NAME/KEY: misc_feature
<222> LOCATION: (211)..(240)
<223> OTHER INFORMATION: At least 4 to 12 of the residues are Gly
<220> FEATURE:
<221> NAME/KEY: misc_feature
<222> LOCATION: (241)..(258)
<223> OTHER INFORMATION: Up to 10 residues may be absent
<220> FEATURE:
<221> NAME/KEY: misc_feature
<222> LOCATION: (241)..(258)
<223> OTHER INFORMATION: Up to 3 amino acid residues may be an amino
      acid other than Ala
<220> FEATURE:
<221> NAME/KEY: misc_feature
<222> LOCATION: (259)..(288)
<223> OTHER INFORMATION: Up to 18 residues may be absent
<220> FEATURE:
<221> NAME/KEY: misc_feature
<222> LOCATION: (259)..(288)
<223> OTHER INFORMATION: At least 4 to 12 of the residues are Gly
<220> FEATURE:
<221> NAME/KEY: misc_feature
<222> LOCATION: (289)..(306)
<223> OTHER INFORMATION: Up to 10 residues may be absent
<220> FEATURE:
<221> NAME/KEY: misc_feature
<222> LOCATION: (289)..(306)
```

```
<223> OTHER INFORMATION: Up to 3 amino acid residues may be an amino
      acid other than Ala
<220> FEATURE:
<221> NAME/KEY: misc_feature
<222> LOCATION: (307)..(336)
<223> OTHER INFORMATION: Up to 18 residues may be absent
<220> FEATURE:
<221> NAME/KEY: misc_feature
<222> LOCATION: (307)..(336)
<223> OTHER INFORMATION: At least 4 to 12 of the residues are Gly
<220> FEATURE:
<221> NAME/KEY: misc_feature
<222> LOCATION: (337)..(354)
<223> OTHER INFORMATION: Up to 10 residues may be absent
<220> FEATURE:
<221> NAME/KEY: misc_feature
<222> LOCATION: (337)..(354)
<223> OTHER INFORMATION: Up to 3 amino acid residues may be an amino
      acid other than Ala
<220> FEATURE:
<221> NAME/KEY: misc_feature
<222> LOCATION: (355)..(384)
<223> OTHER INFORMATION: Up to 18 residues may be absent
<220> FEATURE:
<221> NAME/KEY: misc_feature
<222> LOCATION: (355)..(384)
<223> OTHER INFORMATION: At least 4 to 12 of the residues are Gly

<400> SEQUENCE: 17

Ala Ala Ala Ala Ala Ala Ala Ala Ala Ala Ala Ala Ala Ala Ala Ala
1               5                  10                  15

Ala Ala Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Ala Ala Ala Ala Ala Ala Ala Ala Ala Ala Ala Ala Ala Ala Ala Ala
 50                  55                  60

Ala Ala Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Ala Ala Ala Ala Ala Ala Ala Ala Ala Ala Ala Ala Ala Ala Ala Ala
            100                 105                 110

Ala Ala Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
   130                 135                 140

Ala Ala Ala Ala Ala Ala Ala Ala Ala Ala Ala Ala Ala Ala Ala Ala
145                 150                 155                 160

Ala Ala Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Ala Ala Ala Ala Ala Ala Ala Ala Ala Ala Ala Ala Ala Ala Ala Ala
        195                 200                 205

Ala Ala Gly Gly Gly Gly Gly Gly Gly Gly Gly Gly Gly Gly Gly Gly
    210                 215                 220

Gly Gly Gly Gly Gly Gly Gly Gly Gly Gly Gly Gly Gly Gly Gly Gly
225                 230                 235                 240

Ala Ala Ala Ala Ala Ala Ala Ala Ala Ala Ala Ala Ala Ala Ala Ala
                245                 250                 255

Ala Ala Gly Gly Gly Gly Gly Gly Gly Gly Gly Gly Gly Gly Gly Gly
            260                 265                 270
```

Gly Gly Gly Gly Gly Gly Gly Gly Gly Gly Gly Gly Gly Gly
        275                 280                 285

Ala Ala Ala Ala Ala Ala Ala Ala Ala Ala Ala Ala Ala Ala
290                 295                 300

Ala Ala Gly Gly Gly Gly Gly Gly Gly Gly Gly Gly Gly Gly Gly Gly
305                 310                 315                 320

Gly Gly Gly Gly Gly Gly Gly Gly Gly Gly Gly Gly Gly Gly
            325                 330                 335

Ala Ala Ala Ala Ala Ala Ala Ala Ala Ala Ala Ala Ala Ala
        340                 345                 350

Ala Ala Gly Gly Gly Gly Gly Gly Gly Gly Gly Gly Gly Gly
    355                 360                 365

Gly Gly Gly Gly Gly Gly Gly Gly Gly Gly Gly Gly Gly Gly
    370                 375                 380

<210> SEQ ID NO 18
<211> LENGTH: 402
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(384)
<223> OTHER INFORMATION: Up to 4 of the 48 residue length AG segments
      may be absent
<220> FEATURE:
<221> NAME/KEY: misc_feature
<222> LOCATION: (1)..(18)
<223> OTHER INFORMATION: Up to 10 residues may be absent
<220> FEATURE:
<221> NAME/KEY: misc_feature
<222> LOCATION: (1)..(18)
<223> OTHER INFORMATION: Up to 3 amino acid residues may be an amino
      acid other than Ala
<220> FEATURE:
<221> NAME/KEY: misc_feature
<222> LOCATION: (19)..(48)
<223> OTHER INFORMATION: Up to 18 residues may be absent
<220> FEATURE:
<221> NAME/KEY: misc_feature
<222> LOCATION: (19)..(48)
<223> OTHER INFORMATION: At least 4 to 12 of the residues are Gly
<220> FEATURE:
<221> NAME/KEY: misc_feature
<222> LOCATION: (49)..(66)
<223> OTHER INFORMATION: Up to 10 residues may be absent
<220> FEATURE:
<221> NAME/KEY: misc_feature
<222> LOCATION: (49)..(66)
<223> OTHER INFORMATION: Up to 3 amino acid residues may be an amino
      acid other than Ala
<220> FEATURE:
<221> NAME/KEY: misc_feature
<222> LOCATION: (67)..(96)
<223> OTHER INFORMATION: Up to 18 residues may be absent
<220> FEATURE:
<221> NAME/KEY: misc_feature
<222> LOCATION: (67)..(96)
<223> OTHER INFORMATION: At least 4 to 12 of the residues are Gly
<220> FEATURE:
<221> NAME/KEY: misc_feature
<222> LOCATION: (97)..(114)
<223> OTHER INFORMATION: Up to 10 residues may be absent
<220> FEATURE:
<221> NAME/KEY: misc_feature
<222> LOCATION: (97)..(114)
<223> OTHER INFORMATION: Up to 3 amino acid residues may be an amino
      acid other than Ala
<220> FEATURE:
<221> NAME/KEY: misc_feature
<222> LOCATION: (115)..(144)

-continued

```
<223> OTHER INFORMATION: Up to 18 residues may be absent
<220> FEATURE:
<221> NAME/KEY: misc_feature
<222> LOCATION: (115)..(144)
<223> OTHER INFORMATION: At least 4 to 12 of the residues are Gly
<220> FEATURE:
<221> NAME/KEY: misc_feature
<222> LOCATION: (145)..(162)
<223> OTHER INFORMATION: Up to 10 residues may be absent
<220> FEATURE:
<221> NAME/KEY: misc_feature
<222> LOCATION: (145)..(162)
<223> OTHER INFORMATION: Up to 3 amino acid residues may be an amino
      acid other than Ala
<220> FEATURE:
<221> NAME/KEY: misc_feature
<222> LOCATION: (163)..(192)
<223> OTHER INFORMATION: Up to 18 residues may be absent
<220> FEATURE:
<221> NAME/KEY: misc_feature
<222> LOCATION: (163)..(192)
<223> OTHER INFORMATION: At least 4 to 12 of the residues are Gly
<220> FEATURE:
<221> NAME/KEY: misc_feature
<222> LOCATION: (193)..(210)
<223> OTHER INFORMATION: Up to 10 residues may be absent
<220> FEATURE:
<221> NAME/KEY: misc_feature
<222> LOCATION: (193)..(210)
<223> OTHER INFORMATION: Up to 3 amino acid residues may be an amino
      acid other than Ala
<220> FEATURE:
<221> NAME/KEY: misc_feature
<222> LOCATION: (211)..(240)
<223> OTHER INFORMATION: Up to 18 residues may be absent
<220> FEATURE:
<221> NAME/KEY: misc_feature
<222> LOCATION: (211)..(240)
<223> OTHER INFORMATION: At least 4 to 12 of the residues are Gly
<220> FEATURE:
<221> NAME/KEY: misc_feature
<222> LOCATION: (241)..(258)
<223> OTHER INFORMATION: Up to 10 residues may be absent
<220> FEATURE:
<221> NAME/KEY: misc_feature
<222> LOCATION: (241)..(258)
<223> OTHER INFORMATION: Up to 3 amino acid residues may be an amino
      acid other than Ala
<220> FEATURE:
<221> NAME/KEY: misc_feature
<222> LOCATION: (259)..(288)
<223> OTHER INFORMATION: Up to 18 residues may be absent
<220> FEATURE:
<221> NAME/KEY: misc_feature
<222> LOCATION: (259)..(288)
<223> OTHER INFORMATION: At least 4 to 12 of the residues are Gly
<220> FEATURE:
<221> NAME/KEY: misc_feature
<222> LOCATION: (289)..(306)
<223> OTHER INFORMATION: Up to 10 residues may be absent
<220> FEATURE:
<221> NAME/KEY: misc_feature
<222> LOCATION: (289)..(306)
<223> OTHER INFORMATION: Up to 3 amino acid residues may be an amino
      acid other than Ala
<220> FEATURE:
<221> NAME/KEY: misc_feature
<222> LOCATION: (307)..(336)
<223> OTHER INFORMATION: Up to 18 residues may be absent
<220> FEATURE:
<221> NAME/KEY: misc_feature
<222> LOCATION: (307)..(336)
<223> OTHER INFORMATION: At least 4 to 12 of the residues are Gly
<220> FEATURE:
<221> NAME/KEY: misc_feature
<222> LOCATION: (337)..(354)
<223> OTHER INFORMATION: Up to 10 residues may be absent
<220> FEATURE:
<221> NAME/KEY: misc_feature
<222> LOCATION: (337)..(354)
```

```
<223> OTHER INFORMATION: Up to 3 amino acid residues may be an amino
      acid other than Ala
<220> FEATURE:
<221> NAME/KEY: misc_feature
<222> LOCATION: (355)..(384)
<223> OTHER INFORMATION: Up to 18 residues may be absent
<220> FEATURE:
<221> NAME/KEY: misc_feature
<222> LOCATION: (355)..(384)
<223> OTHER INFORMATION: At least 4 to 12 of the residues are Gly
<220> FEATURE:
<221> NAME/KEY: misc_feature
<222> LOCATION: (385)..(402)
<223> OTHER INFORMATION: Up to 10 residues may be absent
<220> FEATURE:
<221> NAME/KEY: misc_feature
<222> LOCATION: (385)..(402)
<223> OTHER INFORMATION: Up to 3 amino acid residues may be an amino
      acid other than Ala

<400> SEQUENCE: 18

Ala Ala Ala Ala Ala Ala Ala Ala Ala Ala Ala Ala Ala Ala Ala Ala
1               5                   10                  15

Ala Ala Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Ala Ala Ala Ala Ala Ala Ala Ala Ala Ala Ala Ala Ala Ala Ala Ala
    50                  55                  60

Ala Ala Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Ala Ala Ala Ala Ala Ala Ala Ala Ala Ala Ala Ala Ala Ala Ala Ala
            100                 105                 110

Ala Ala Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Ala Ala Ala Ala Ala Ala Ala Ala Ala Ala Ala Ala Ala Ala Ala Ala
145                 150                 155                 160

Ala Ala Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Ala Ala Ala Ala Ala Ala Ala Ala Ala Ala Ala Ala Ala Ala Ala Ala
        195                 200                 205

Ala Ala Gly Gly Gly Gly Gly Gly Gly Gly Gly Gly Gly Gly Gly Gly
    210                 215                 220

Gly Gly Gly Gly Gly Gly Gly Gly Gly Gly Gly Gly Gly Gly Gly Gly
225                 230                 235                 240

Ala Ala Ala Ala Ala Ala Ala Ala Ala Ala Ala Ala Ala Ala Ala Ala
                245                 250                 255

Ala Ala Gly Gly Gly Gly Gly Gly Gly Gly Gly Gly Gly Gly Gly Gly
            260                 265                 270

Gly Gly Gly Gly Gly Gly Gly Gly Gly Gly Gly Gly Gly Gly Gly Gly
        275                 280                 285

Ala Ala Ala Ala Ala Ala Ala Ala Ala Ala Ala Ala Ala Ala Ala Ala
    290                 295                 300

Ala Ala Gly Gly Gly Gly Gly Gly Gly Gly Gly Gly Gly Gly Gly Gly
```

```
                    305                 310                 315                 320
Gly Gly Gly Gly Gly Gly Gly Gly Gly Gly Gly Gly Gly Gly Gly
                325                 330                 335

Ala Ala Ala Ala Ala Ala Ala Ala Ala Ala Ala Ala Ala Ala Ala
            340                 345                 350

Ala Ala Gly Gly Gly Gly Gly Gly Gly Gly Gly Gly Gly Gly Gly
        355                 360                 365

Gly Gly Gly Gly Gly Gly Gly Gly Gly Gly Gly Gly Gly Gly Gly
    370                 375                 380

Ala Ala Ala Ala Ala Ala Ala Ala Ala Ala Ala Ala Ala Ala Ala
385                 390                 395                 400

Ala Ala

<210> SEQ ID NO 19
<211> LENGTH: 384
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(384)
<223> OTHER INFORMATION: Up to 4 of the 48 residue length AG segments
      may be absent
<220> FEATURE:
<221> NAME/KEY: misc_feature
<222> LOCATION: (1)..(30)
<223> OTHER INFORMATION: Up to 18 residues may be absent
<220> FEATURE:
<221> NAME/KEY: misc_feature
<222> LOCATION: (1)..(30)
<223> OTHER INFORMATION: At least 4 to 12 of the residues are Gly
<220> FEATURE:
<221> NAME/KEY: misc_feature
<222> LOCATION: (31)..(48)
<223> OTHER INFORMATION: Up to 10 residues may be absent
<220> FEATURE:
<221> NAME/KEY: misc_feature
<222> LOCATION: (31)..(48)
<223> OTHER INFORMATION: Up to 3 amino acid residues may be an amino
      acid other than Ala
<220> FEATURE:
<221> NAME/KEY: misc_feature
<222> LOCATION: (49)..(78)
<223> OTHER INFORMATION: Up to 18 residues may be absent
<220> FEATURE:
<221> NAME/KEY: misc_feature
<222> LOCATION: (49)..(78)
<223> OTHER INFORMATION: At least 4 to 12 of the residues are Gly
<220> FEATURE:
<221> NAME/KEY: misc_feature
<222> LOCATION: (79)..(96)
<223> OTHER INFORMATION: Up to 10 residues may be absent
<220> FEATURE:
<221> NAME/KEY: misc_feature
<222> LOCATION: (79)..(96)
<223> OTHER INFORMATION: Up to 3 amino acid residues may be an amino
      acid other than Ala
<220> FEATURE:
<221> NAME/KEY: misc_feature
<222> LOCATION: (97)..(126)
<223> OTHER INFORMATION: Up to 18 residues may be absent
<220> FEATURE:
<221> NAME/KEY: misc_feature
<222> LOCATION: (97)..(126)
<223> OTHER INFORMATION: At least 4 to 12 of the residues are Gly
<220> FEATURE:
<221> NAME/KEY: misc_feature
<222> LOCATION: (127)..(144)
<223> OTHER INFORMATION: Up to 10 residues may be absent
<220> FEATURE:
<221> NAME/KEY: misc_feature
<222> LOCATION: (127)..(144)
```

-continued

```
<223> OTHER INFORMATION: Up to 3 amino acid residues may be an amino
      acid other than Ala
<220> FEATURE:
<221> NAME/KEY: misc_feature
<222> LOCATION: (145)..(174)
<223> OTHER INFORMATION: Up to 18 residues may be absent
<220> FEATURE:
<221> NAME/KEY: misc_feature
<222> LOCATION: (145)..(174)
<223> OTHER INFORMATION: At least 4 to 12 of the residues are Gly
<220> FEATURE:
<221> NAME/KEY: misc_feature
<222> LOCATION: (175)..(192)
<223> OTHER INFORMATION: Up to 10 residues may be absent
<220> FEATURE:
<221> NAME/KEY: misc_feature
<222> LOCATION: (175)..(192)
<223> OTHER INFORMATION: Up to 3 amino acid residues may be an amino
      acid other than Ala
<220> FEATURE:
<221> NAME/KEY: misc_feature
<222> LOCATION: (193)..(222)
<223> OTHER INFORMATION: Up to 18 residues may be absent
<220> FEATURE:
<221> NAME/KEY: misc_feature
<222> LOCATION: (193)..(222)
<223> OTHER INFORMATION: At least 4 to 12 of the residues are Gly
<220> FEATURE:
<221> NAME/KEY: misc_feature
<222> LOCATION: (223)..(240)
<223> OTHER INFORMATION: Up to 10 residues may be absent
<220> FEATURE:
<221> NAME/KEY: misc_feature
<222> LOCATION: (223)..(240)
<223> OTHER INFORMATION: Up to 3 amino acid residues may be an amino
      acid other than Ala
<220> FEATURE:
<221> NAME/KEY: misc_feature
<222> LOCATION: (241)..(270)
<223> OTHER INFORMATION: Up to 18 residues may be absent
<220> FEATURE:
<221> NAME/KEY: misc_feature
<222> LOCATION: (241)..(270)
<223> OTHER INFORMATION: At least 4 to 12 of the residues are Gly
<220> FEATURE:
<221> NAME/KEY: misc_feature
<222> LOCATION: (271)..(288)
<223> OTHER INFORMATION: Up to 10 residues may be absent
<220> FEATURE:
<221> NAME/KEY: misc_feature
<222> LOCATION: (271)..(288)
<223> OTHER INFORMATION: Up to 3 amino acid residues may be an amino
      acid other than Ala
<220> FEATURE:
<221> NAME/KEY: misc_feature
<222> LOCATION: (289)..(318)
<223> OTHER INFORMATION: Up to 18 residues may be absent
<220> FEATURE:
<221> NAME/KEY: misc_feature
<222> LOCATION: (289)..(318)
<223> OTHER INFORMATION: At least 4 to 12 of the residues are Gly
<220> FEATURE:
<221> NAME/KEY: misc_feature
<222> LOCATION: (319)..(336)
<223> OTHER INFORMATION: Up to 10 residues may be absent
<220> FEATURE:
<221> NAME/KEY: misc_feature
<222> LOCATION: (319)..(336)
<223> OTHER INFORMATION: Up to 3 amino acid residues may be an amino
      acid other than Ala
<220> FEATURE:
<221> NAME/KEY: misc_feature
<222> LOCATION: (337)..(366)
<223> OTHER INFORMATION: Up to 18 residues may be absent
<220> FEATURE:
<221> NAME/KEY: misc_feature
<222> LOCATION: (337)..(366)
<223> OTHER INFORMATION: At least 4 to 12 of the residues are Gly
<220> FEATURE:
<221> NAME/KEY: misc_feature
```

<222> LOCATION: (367)..(384)
<223> OTHER INFORMATION: Up to 10 residues may be absent
<220> FEATURE:
<221> NAME/KEY: misc_feature
<222> LOCATION: (367)..(384)
<223> OTHER INFORMATION: Up to 3 amino acid residues may be an amino
      acid other than Ala

<400> SEQUENCE: 19

Gly Gly Gly Gly Gly Gly Gly Gly Gly Gly Gly Gly Gly Gly Gly
1               5                  10                  15

Gly Gly Gly Gly Gly Gly Gly Gly Gly Gly Gly Gly Gly Gly Ala Ala
            20                  25                  30

Ala Ala Ala Ala Ala Ala Ala Ala Ala Ala Ala Ala Ala Ala Ala
            35                  40                  45

Gly Gly Gly Gly Gly Gly Gly Gly Gly Gly Gly Gly Gly Gly Gly
50                  55                  60

Gly Gly Gly Gly Gly Gly Gly Gly Gly Gly Gly Gly Gly Gly Ala Ala
65                  70                  75                  80

Ala Ala Ala Ala Ala Ala Ala Ala Ala Ala Ala Ala Ala Ala Ala
            85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Ala Ala
            115                 120                 125

Ala Ala Ala Ala Ala Ala Ala Ala Ala Ala Ala Ala Ala Ala Ala
            130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Ala Ala
            165                 170                 175

Ala Ala Ala Ala Ala Ala Ala Ala Ala Ala Ala Ala Ala Ala Ala
            180                 185                 190

Gly Gly Gly Gly Gly Gly Gly Gly Gly Gly Gly Gly Gly Gly Gly
            195                 200                 205

Gly Gly Gly Gly Gly Gly Gly Gly Gly Gly Gly Gly Gly Ala Ala
            210                 215                 220

Ala Ala Ala Ala Ala Ala Ala Ala Ala Ala Ala Ala Ala Ala Ala
225                 230                 235                 240

Gly Gly Gly Gly Gly Gly Gly Gly Gly Gly Gly Gly Gly Gly Gly
            245                 250                 255

Gly Gly Gly Gly Gly Gly Gly Gly Gly Gly Gly Gly Gly Ala Ala
            260                 265                 270

Ala Ala Ala Ala Ala Ala Ala Ala Ala Ala Ala Ala Ala Ala Ala
            275                 280                 285

Gly Gly Gly Gly Gly Gly Gly Gly Gly Gly Gly Gly Gly Gly Gly
290                 295                 300

Gly Gly Gly Gly Gly Gly Gly Gly Gly Gly Gly Gly Gly Ala Ala
305                 310                 315                 320

Ala Ala Ala Ala Ala Ala Ala Ala Ala Ala Ala Ala Ala Ala Ala
            325                 330                 335

Gly Gly Gly Gly Gly Gly Gly Gly Gly Gly Gly Gly Gly Gly Gly
            340                 345                 350

Gly Gly Gly Gly Gly Gly Gly Gly Gly Gly Gly Gly Gly Ala Ala
            355                 360                 365

Ala Ala Ala Ala Ala Ala Ala Ala Ala Ala Ala Ala Ala Ala Ala

```
                    370                 375                 380

<210> SEQ ID NO 20
<211> LENGTH: 414
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(384)
<223> OTHER INFORMATION: Up to 4 of the 48 residue length AG segments
      may be absent
<220> FEATURE:
<221> NAME/KEY: misc_feature
<222> LOCATION: (1)..(30)
<223> OTHER INFORMATION: Up to 18 residues may be absent
<220> FEATURE:
<221> NAME/KEY: misc_feature
<222> LOCATION: (1)..(30)
<223> OTHER INFORMATION: At least 4 to 12 of the residues are Gly
<220> FEATURE:
<221> NAME/KEY: misc_feature
<222> LOCATION: (31)..(48)
<223> OTHER INFORMATION: Up to 10 residues may be absent
<220> FEATURE:
<221> NAME/KEY: misc_feature
<222> LOCATION: (31)..(48)
<223> OTHER INFORMATION: Up to 3 amino acid residues may be an amino
      acid other than Ala
<220> FEATURE:
<221> NAME/KEY: misc_feature
<222> LOCATION: (49)..(78)
<223> OTHER INFORMATION: Up to 18 residues may be absent
<220> FEATURE:
<221> NAME/KEY: misc_feature
<222> LOCATION: (49)..(78)
<223> OTHER INFORMATION: At least 4 to 12 of the residues are Gly
<220> FEATURE:
<221> NAME/KEY: misc_feature
<222> LOCATION: (79)..(96)
<223> OTHER INFORMATION: Up to 10 residues may be absent
<220> FEATURE:
<221> NAME/KEY: misc_feature
<222> LOCATION: (79)..(96)
<223> OTHER INFORMATION: Up to 3 amino acid residues may be an amino
      acid other than Ala
<220> FEATURE:
<221> NAME/KEY: misc_feature
<222> LOCATION: (97)..(126)
<223> OTHER INFORMATION: Up to 18 residues may be absent
<220> FEATURE:
<221> NAME/KEY: misc_feature
<222> LOCATION: (97)..(126)
<223> OTHER INFORMATION: At least 4 to 12 of the residues are Gly
<220> FEATURE:
<221> NAME/KEY: misc_feature
<222> LOCATION: (127)..(144)
<223> OTHER INFORMATION: Up to 10 residues may be absent
<220> FEATURE:
<221> NAME/KEY: misc_feature
<222> LOCATION: (127)..(144)
<223> OTHER INFORMATION: Up to 3 amino acid residues may be an amino
      acid other than Ala
<220> FEATURE:
<221> NAME/KEY: misc_feature
<222> LOCATION: (145)..(174)
<223> OTHER INFORMATION: Up to 18 residues may be absent
<220> FEATURE:
<221> NAME/KEY: misc_feature
<222> LOCATION: (145)..(174)
<223> OTHER INFORMATION: At least 4 to 12 of the residues are Gly
<220> FEATURE:
<221> NAME/KEY: misc_feature
<222> LOCATION: (175)..(192)
<223> OTHER INFORMATION: Up to 10 residues may be absent
<220> FEATURE:
<221> NAME/KEY: misc_feature
<222> LOCATION: (175)..(192)
```

```
<223> OTHER INFORMATION: Up to 3 amino acid residues may be an amino
      acid other than Ala
<220> FEATURE:
<221> NAME/KEY: misc_feature
<222> LOCATION: (193)..(222)
<223> OTHER INFORMATION: Up to 18 residues may be absent
<220> FEATURE:
<221> NAME/KEY: misc_feature
<222> LOCATION: (193)..(222)
<223> OTHER INFORMATION: At least 4 to 12 of the residues are Gly
<220> FEATURE:
<221> NAME/KEY: misc_feature
<222> LOCATION: (223)..(240)
<223> OTHER INFORMATION: Up to 10 residues may be absent
<220> FEATURE:
<221> NAME/KEY: misc_feature
<222> LOCATION: (223)..(240)
<223> OTHER INFORMATION: Up to 3 amino acid residues may be an amino
      acid other than Ala
<220> FEATURE:
<221> NAME/KEY: misc_feature
<222> LOCATION: (241)..(270)
<223> OTHER INFORMATION: Up to 18 residues may be absent
<220> FEATURE:
<221> NAME/KEY: misc_feature
<222> LOCATION: (241)..(270)
<223> OTHER INFORMATION: At least 4 to 12 of the residues are Gly
<220> FEATURE:
<221> NAME/KEY: misc_feature
<222> LOCATION: (271)..(288)
<223> OTHER INFORMATION: Up to 10 residues may be absent
<220> FEATURE:
<221> NAME/KEY: misc_feature
<222> LOCATION: (271)..(288)
<223> OTHER INFORMATION: Up to 3 amino acid residues may be an amino
      acid other than Ala
<220> FEATURE:
<221> NAME/KEY: misc_feature
<222> LOCATION: (289)..(318)
<223> OTHER INFORMATION: Up to 18 residues may be absent
<220> FEATURE:
<221> NAME/KEY: misc_feature
<222> LOCATION: (289)..(318)
<223> OTHER INFORMATION: At least 4 to 12 of the residues are Gly
<220> FEATURE:
<221> NAME/KEY: misc_feature
<222> LOCATION: (319)..(336)
<223> OTHER INFORMATION: Up to 10 residues may be absent
<220> FEATURE:
<221> NAME/KEY: misc_feature
<222> LOCATION: (319)..(336)
<223> OTHER INFORMATION: Up to 3 amino acid residues may be an amino
      acid other than Ala
<220> FEATURE:
<221> NAME/KEY: misc_feature
<222> LOCATION: (337)..(366)
<223> OTHER INFORMATION: Up to 18 residues may be absent
<220> FEATURE:
<221> NAME/KEY: misc_feature
<222> LOCATION: (337)..(366)
<223> OTHER INFORMATION: At least 4 to 12 of the residues are Gly
<220> FEATURE:
<221> NAME/KEY: misc_feature
<222> LOCATION: (367)..(384)
<223> OTHER INFORMATION: Up to 10 residues may be absent
<220> FEATURE:
<221> NAME/KEY: misc_feature
<222> LOCATION: (367)..(384)
<223> OTHER INFORMATION: Up to 3 amino acid residues may be an amino
      acid other than Ala
<220> FEATURE:
<221> NAME/KEY: misc_feature
<222> LOCATION: (385)..(414)
<223> OTHER INFORMATION: Up to 18 residues may be absent
<220> FEATURE:
<221> NAME/KEY: misc_feature
<222> LOCATION: (385)..(414)
<223> OTHER INFORMATION: At least 4 to 12 of the residues are Gly

<400> SEQUENCE: 20
```

```
Gly Gly Gly Gly Gly Gly Gly Gly Gly Gly Gly Gly Gly Gly Gly
1               5                   10                  15
Gly Gly Gly Gly Gly Gly Gly Gly Gly Gly Gly Gly Gly Ala Ala
            20                  25                  30
Ala Ala Ala Ala Ala Ala Ala Ala Ala Ala Ala Ala Ala Ala Ala
            35                  40                  45
Gly Gly Gly Gly Gly Gly Gly Gly Gly Gly Gly Gly Gly Gly Gly
50                  55                  60
Gly Gly Gly Gly Gly Gly Gly Gly Gly Gly Gly Gly Gly Ala Ala
65                  70                  75                  80
Ala Ala Ala Ala Ala Ala Ala Ala Ala Ala Ala Ala Ala Ala Ala
            85                  90                  95
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Ala Ala
            115                 120                 125
Ala Ala Ala Ala Ala Ala Ala Ala Ala Ala Ala Ala Ala Ala Ala
130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Ala Ala
            165                 170                 175
Ala Ala Ala Ala Ala Ala Ala Ala Ala Ala Ala Ala Ala Ala Ala
            180                 185                 190
Gly Gly Gly Gly Gly Gly Gly Gly Gly Gly Gly Gly Gly Gly Gly
            195                 200                 205
Gly Gly Gly Gly Gly Gly Gly Gly Gly Gly Gly Gly Gly Ala Ala
            210                 215                 220
Ala Ala Ala Ala Ala Ala Ala Ala Ala Ala Ala Ala Ala Ala Ala
225                 230                 235                 240
Gly Gly Gly Gly Gly Gly Gly Gly Gly Gly Gly Gly Gly Gly Gly
            245                 250                 255
Gly Gly Gly Gly Gly Gly Gly Gly Gly Gly Gly Gly Gly Ala Ala
            260                 265                 270
Ala Ala Ala Ala Ala Ala Ala Ala Ala Ala Ala Ala Ala Ala Ala
            275                 280                 285
Gly Gly Gly Gly Gly Gly Gly Gly Gly Gly Gly Gly Gly Gly Gly
            290                 295                 300
Gly Gly Gly Gly Gly Gly Gly Gly Gly Gly Gly Gly Gly Ala Ala
305                 310                 315                 320
Ala Ala Ala Ala Ala Ala Ala Ala Ala Ala Ala Ala Ala Ala Ala
            325                 330                 335
Gly Gly Gly Gly Gly Gly Gly Gly Gly Gly Gly Gly Gly Gly Gly
            340                 345                 350
Gly Gly Gly Gly Gly Gly Gly Gly Gly Gly Gly Gly Gly Ala Ala
            355                 360                 365
Ala Ala Ala Ala Ala Ala Ala Ala Ala Ala Ala Ala Ala Ala Ala
            370                 375                 380
Gly Gly Gly Gly Gly Gly Gly Gly Gly Gly Gly Gly Gly Gly Gly
385                 390                 395                 400
Gly Gly Gly Gly Gly Gly Gly Gly Gly Gly Gly Gly Gly Gly
            405                 410
```

```
<210> SEQ ID NO 21
<211> LENGTH: 14
<212> TYPE: PRT
<213> ORGANISM: Artificial Sequence
<220> FEATURE:
<223> OTHER INFORMATION: Synthetic peptide

<400> SEQUENCE: 21

Ala Ala Ala Ala Ala Ala Ala Ala Ala Ala Ala Ala Ala Ala
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Ala Ser Ala Ser Ala Ala Ala Ser Ala Ala Ser Thr Val Ala Asn Ser
1               5                   10                  15

Val Ser

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Ala Ser Ala Ala Ser Ala Ala Ala Ser
1               5

<210> SEQ ID NO 24
<211> LENGTH: 100
<212> TYPE: PRT
<213> ORGANISM: Artificial Sequence
<220> FEATURE:
<223> OTHER INFORMATION: Synthetic peptide

<400> SEQUENCE: 24

Ser Arg Leu Ser Ser Pro Glu Ala Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
                35                  40                  45

Ser Gly Cys Asp Val Leu Val Gln Ala Leu Leu Glu Val Val Ser Ala
        50                  55                  60

Leu Ile His Ile Leu Gly Ser Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
            100

<210> SEQ ID NO 25
<211> LENGTH: 98
<212> TYPE: PRT
<213> ORGANISM: Artificial Sequence
<220> FEATURE:
<223> OTHER INFORMATION: Synthetic peptide

<400> SEQUENCE: 25
```

```
Ser Arg Leu Ser Ser Pro Ser Ala Val Ser Arg Val Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
            35                  40                  45

Ser Gly Cys Glu Val Ile Val Gln Ala Leu Leu Glu Val Ile Thr Ala
        50                  55                  60

Leu Val Gln Ile Val Ser Ser Ser Val Gly Tyr Ile Asn Pro Ser
65              70                  75                  80

Ala Val Asn Gln Ile Thr Asn Val Val Ala Asn Ala Met Ala Gln Val
                85                  90                  95

Met Gly
```

<210> SEQ ID NO 26
<211> LENGTH: 99
<212> TYPE: PRT
<213> ORGANISM: Artificial Sequence
<220> FEATURE:
<223> OTHER INFORMATION: Synthetic peptide

<400> SEQUENCE: 26

```
Ser Arg Leu Ser Ser Pro Gly Ala Ala Ser Arg Val Ser Ala Val
1               5                   10                  15

Thr Ser Leu Val Ser Ser Gly Gly Pro Thr Asn Ser Ala Ala Leu Ser
            20                  25                  30

Asn Thr Ile Ser Asn Val Val Ser Gln Ile Ser Ser Asn Pro Gly
            35                  40                  45

Leu Ser Gly Cys Asp Val Leu Val Gln Ala Leu Leu Glu Ile Val Ser
        50                  55                  60

Ala Leu Val His Ile Leu Gly Ser Ala Asn Ile Gly Gln Val Asn Ser
65              70                  75                  80

Ser Gly Val Gly Arg Ser Ala Ser Ile Val Gly Gln Ser Ile Asn Gln
                85                  90                  95

Ala Phe Ser
```

<210> SEQ ID NO 27
<211> LENGTH: 89
<212> TYPE: PRT
<213> ORGANISM: Artificial Sequence
<220> FEATURE:
<223> OTHER INFORMATION: Synthetic peptide

<400> SEQUENCE: 27

```
Ser His Leu Ser Ser Pro Glu Ala Ser Ser Arg Val Ser Ala Val
1               5                   10                  15

Ser Asn Leu Val Ser Ser Gly Ser Thr Asn Ser Ala Ala Leu Pro Asn
            20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65              70                  75                  80

Ser Ala Gly Gln Ala Thr Gln Ile Val
                85
```

```
<210> SEQ ID NO 28
<211> LENGTH: 98
<212> TYPE: PRT
<213> ORGANISM: Artificial Sequence
<220> FEATURE:
<223> OTHER INFORMATION: Synthetic peptide

<400> SEQUENCE: 28

Ser Ala Leu Ala Ala Pro Ala Thr Ser Ala Arg Ile Ser Ser His Ala
1               5                   10                  15

Ser Thr Leu Leu Ser Asn Gly Pro Thr Asn Pro Ala Ser Ile Ser Asn
            20                  25                  30

Val Ile Ser Asn Ala Val Ser Gln Ile Ser Ser Asn Pro Gly Ala
        35                  40                  45

Ser Ser Cys Asp Val Leu Val Gln Ala Leu Leu Glu Leu Val Thr Ala
    50                  55                  60

Leu Leu Thr Ile Ile Gly Ser Ser Asn Val Gly Asn Val Asn Tyr Asp
65                  70                  75                  80

Ser Ser Gly Gln Tyr Ala Gln Val Val Ser Gln Ser Val Gln Asn Ala
                85                  90                  95

Phe Val

<210> SEQ ID NO 29
<211> LENGTH: 98
<212> TYPE: PRT
<213> ORGANISM: Artificial Sequence
<220> FEATURE:
<223> OTHER INFORMATION: Synthetic peptide

<400> SEQUENCE: 29

Ser Ala Leu Ser Ala Pro Ala Thr Ser Ala Arg Ile Ser Ser His Ala
1               5                   10                  15

Ser Ala Leu Leu Ser Ser Gly Pro Thr Asn Pro Ala Ser Ile Ser Asn
            20                  25                  30

Val Ile Ser Asn Ala Val Ser Gln Ile Ser Ser Ser Asn Pro Gly Ala
        35                  40                  45

Ser Ala Cys Asp Val Leu Val Gln Ala Leu Leu Glu Leu Val Thr Ala
    50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Val
                85                  90                  95

Phe Gly

<210> SEQ ID NO 30
<211> LENGTH: 93
<212> TYPE: PRT
<213> ORGANISM: Artificial Sequence
<220> FEATURE:
<223> OTHER INFORMATION: Synthetic peptide

<400> SEQUENCE: 30

Ser His Leu Ser Ser Pro Glu Ala Ser Ser Arg Val Ser Ala Val
1               5                   10                  15

Ser Asn Leu Val Ser Gly Gly Ser Thr Asn Ser Ala Ala Leu Pro Asn
            20                  25                  30

Thr Ile Ser Asn Val Val Ser Gln Ile Ser Ser Asn Pro Gly Leu
        35                  40                  45

Ser Gly Cys Asp Val Leu Val Gln Ala Leu Leu Glu Val Val Ser Ala
    50                  55                  60
```

```
Leu Ile His Ile Leu Gly Ser Ser Ile Gly Gln Val Asp Tyr Gly
65                  70                  75                  80

Ser Ala Gly Gln Ala Thr Gln Ile Val Gly Gln Ser Ala
                85                  90
```

<210> SEQ ID NO 31
<211> LENGTH: 98
<212> TYPE: PRT
<213> ORGANISM: Artificial Sequence
<220> FEATURE:
<223> OTHER INFORMATION: Synthetic peptide

<400> SEQUENCE: 31

```
Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Ile Gln Ile Leu Gly Ser Ser Ile Gly Gln Val Asn Tyr Gly
65                  70                  75                  80

Ser Ala Gly Gln Ala Thr Gln Ile Val Gly Gln Ser Val Tyr Gln Ala
                85                  90                  95

Leu Gly
```

<210> SEQ ID NO 32
<211> LENGTH: 89
<212> TYPE: PRT
<213> ORGANISM: Artificial Sequence
<220> FEATURE:
<223> OTHER INFORMATION: Synthetic peptide

<400> SEQUENCE: 32

```
Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85
```

<210> SEQ ID NO 33
<211> LENGTH: 87
<212> TYPE: PRT
<213> ORGANISM: Artificial Sequence
<220> FEATURE:
<223> OTHER INFORMATION: Synthetic peptide

<400> SEQUENCE: 33

```
Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30
```

```
Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln
                85
```

<210> SEQ ID NO 34
<211> LENGTH: 87
<212> TYPE: PRT
<213> ORGANISM: Artificial Sequence
<220> FEATURE:
<223> OTHER INFORMATION: Synthetic peptide

<400> SEQUENCE: 34

```
Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
 50                  55                  60

Leu Val His Ile Leu Gly Ser Ser Ile Gly Gln Val Asn Tyr Gly
 65                  70                  75                  80

Ser Ala Gly Gln Ala Thr Gln
                85
```

<210> SEQ ID NO 35
<211> LENGTH: 89
<212> TYPE: PRT
<213> ORGANISM: Artificial Sequence
<220> FEATURE:
<223> OTHER INFORMATION: Synthetic peptide

<400> SEQUENCE: 35

```
Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Asn
            20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
 50                  55                  60

Pro Ile His Ile Leu Gly Ser Ser Ile Gly Gln Val Asn Tyr Gly
 65                  70                  75                  80

Ser Ala Gly Gln Ala Thr Gln Ile Val
                85
```

<210> SEQ ID NO 36
<211> LENGTH: 89
<212> TYPE: PRT
<213> ORGANISM: Artificial Sequence
<220> FEATURE:
<223> OTHER INFORMATION: Synthetic peptide

<400> SEQUENCE: 36

```
Ser Arg Leu Ser Ser Pro Glu Ala Ser Ser Arg Val Ser Ser Ala Val
```

-continued

```
                1               5                  10                 15
Ser Asn Leu Val Ser Ser Gly Pro Thr Asn Ser Ala Ala Leu Pro Asn
                20                 25                 30

Thr Ile Ser Asn Val Val Ser Gln Ile Ser Ser Asn Pro Gly Leu
            35                 40                 45

Ser Gly Cys Asp Val Leu Val Gln Ala Leu Leu Glu Val Val Ser Ala
    50                  55                 60

Leu Ile His Ile Leu Gly Ser Ser Ile Gly Gln Val Asn Tyr Gly
65                  70                 75                  80

Ser Ala Gly Gln Ala Thr Gln Ile Val
                85
```

<210> SEQ ID NO 37
<211> LENGTH: 88
<212> TYPE: PRT
<213> ORGANISM: Artificial Sequence
<220> FEATURE:
<223> OTHER INFORMATION: Synthetic peptide

<400> SEQUENCE: 37

```
Ser Leu Leu Ser Ser Pro Ala Ser Asn Ala Arg Ile Ser Ala Val
1               5                  10                 15

Ser Ala Leu Ala Ser Gly Ala Ala Ser Gly Pro Gly Tyr Leu Ser Ser
            20                 25                 30

Val Ile Ser Asn Val Val Ser Gln Val Ser Asn Ser Gly Gly Leu
            35                 40                 45

Val Gly Cys Asp Thr Leu Val Gln Ala Leu Leu Glu Ala Ala Ala Ala
    50                  55                 60

Leu Val His Val Leu Ala Ser Ser Gly Gly Gln Val Asn Leu Asn
65                  70                 75                  80

Thr Ala Gly Tyr Thr Ser Gln Leu
                85
```

<210> SEQ ID NO 38
<211> LENGTH: 88
<212> TYPE: PRT
<213> ORGANISM: Artificial Sequence
<220> FEATURE:
<223> OTHER INFORMATION: Synthetic peptide

<400> SEQUENCE: 38

```
Ser Arg Leu Ser Ser Pro Ala Ser Asn Ala Arg Ile Ser Ser Ala Val
1               5                  10                 15

Ser Ala Leu Ala Ser Gly Gly Ala Ser Ser Pro Gly Tyr Leu Ser Ser
            20                 25                 30

Ile Ile Ser Asn Val Val Ser Gln Val Ser Ser Asn Asn Asp Gly Leu
            35                 40                 45

Ser Gly Cys Asp Thr Val Val Gln Ala Leu Leu Glu Val Ala Ala
    50                  55                 60

Leu Val His Val Leu Ala Ser Ser Asn Ile Gly Gln Val Asn Leu Asn
65                  70                 75                  80

Thr Ala Gly Tyr Thr Ser Gln Leu
                85
```

<210> SEQ ID NO 39
<211> LENGTH: 89
<212> TYPE: PRT
<213> ORGANISM: Artificial Sequence
<220> FEATURE:
<223> OTHER INFORMATION: Synthetic peptide

<400> SEQUENCE: 39

Ser Arg Leu Ser Ser Ala Ala Ser Ser Arg Val Ser Ser Ala Val
1               5                   10                  15

Ser Ser Leu Val Ser Ser Gly Pro Thr Thr Pro Ala Ala Leu Ser Asn
            20                  25                  30

Thr Ile Ser Ser Ala Val Ser Gln Ile Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Val Gly Gln Ile Asn Tyr Gly
65                  70                  75                  80

Ala Ser Ala Gln Tyr Ala Gln Met Val
                85

<210> SEQ ID NO 40
<211> LENGTH: 97
<212> TYPE: PRT
<213> ORGANISM: Artificial Sequence
<220> FEATURE:
<223> OTHER INFORMATION: Synthetic peptide

<400> SEQUENCE: 40

Arg Leu Ser Ser Pro Gln Ala Ser Ser Arg Val Ser Ser Ala Val Ser
1               5                   10                  15

Thr Leu Val Ser Ser Gly Pro Thr Asn Pro Ala Ser Leu Ser Asn Ala
            20                  25                  30

Ile Gly Ser Val Val Ser Gln Val Ser Ala Ser Asn Pro Gly Leu Pro
        35                  40                  45

Ser Cys Asp Val Leu Val Gln Ala Leu Leu Glu Ile Val Ser Ala Leu
    50                  55                  60

Val His Ile Leu Gly Ser Ser Ile Gly Gln Ile Asn Tyr Ser Ala
65                  70                  75                  80

Ser Ser Gln Tyr Ala Arg Leu Val Gly Gln Ser Ile Ala Gln Ala Leu
                85                  90                  95

Gly

<210> SEQ ID NO 41
<211> LENGTH: 82
<212> TYPE: PRT
<213> ORGANISM: Artificial Sequence
<220> FEATURE:
<223> OTHER INFORMATION: Synthetic peptide

<400> SEQUENCE: 41

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ala Leu Ser Asn
            20                  25                  30

Ala Ile Ser Ser Val Val Ser Gln Val Ser Ala Ser Asn Pro Gly Leu
        35                  40                  45

Ser Gly Cys Asp Val Leu Val Gln Ala Leu Leu Glu Leu Val Ser Ala
    50                  55                  60

Leu Val His Ile Leu Gly Ser Ser Ile Gly Gln Ile Asn Tyr Ala
65                  70                  75                  80

Ala Ser

<210> SEQ ID NO 42

```
<211> LENGTH: 98
<212> TYPE: PRT
<213> ORGANISM: Artificial Sequence
<220> FEATURE:
<223> OTHER INFORMATION: Synthetic peptide

<400> SEQUENCE: 42

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ser Leu Ser Asn
            20                  25                  30

Ala Ile Ser Ser Val Val Ser Gln Val Ser Ser Asn Pro Gly Leu
        35                  40                  45

Ser Gly Cys Asp Val Leu Val Gln Ala Leu Leu Glu Ile Val Ser Ala
    50                  55                  60

Leu Val His Ile Leu Gly Ser Ser Ile Gly Gln Ile Asn Tyr Ala
65                  70                  75                  80

Ala Ser Ser Gln Tyr Ala Gln Leu Val Gly Gln Ser Leu Thr Gln Ala
                85                  90                  95

Leu Gly

<210> SEQ ID NO 43
<211> LENGTH: 89
<212> TYPE: PRT
<213> ORGANISM: Artificial Sequence
<220> FEATURE:
<223> OTHER INFORMATION: Synthetic peptide

<400> SEQUENCE: 43

Ser Arg Leu Ser Ser Pro Gln Ala Gly Ala Arg Val Ser Ser Ala Val
1               5                   10                  15

Ser Ala Leu Val Ala Ser Gly Pro Thr Ser Pro Ala Ala Val Ser Ser
            20                  25                  30

Ala Ile Ser Asn Val Ala Ser Gln Ile Ser Ala Ser Asn Pro Gly Leu
        35                  40                  45

Ser Gly Cys Asp Val Leu Val Gln Ala Leu Leu Glu Ile Val Ser Ala
    50                  55                  60

Leu Val Ser Ile Leu Ser Ser Ala Ser Ile Gly Gln Ile Asn Tyr Gly
65                  70                  75                  80

Ala Ser Gly Gln Tyr Ala Ala Met Ile
                85

<210> SEQ ID NO 44
<211> LENGTH: 90
<212> TYPE: PRT
<213> ORGANISM: Artificial Sequence
<220> FEATURE:
<223> OTHER INFORMATION: Synthetic peptide

<400> SEQUENCE: 44

Ser Ala Leu Ser Ser Pro Thr Thr His Ala Arg Ile Ser Ser His Ala
1               5                   10                  15

Ser Thr Leu Leu Ser Ser Gly Pro Thr Asn Ser Ala Ala Ile Ser Asn
            20                  25                  30

Val Ile Ser Asn Ala Val Ser Gln Val Ser Ala Ser Asn Pro Gly Ser
        35                  40                  45

Ser Ser Cys Asp Val Leu Val Gln Ala Leu Leu Glu Leu Ile Thr Ala
    50                  55                  60

Leu Ile Ser Ile Val Asp Ser Ser Asn Ile Gly Gln Val Asn Tyr Gly
65                  70                  75                  80
```

```
Ser Ser Gly Gln Tyr Ala Gln Met Val Gly
                85                  90

<210> SEQ ID NO 45
<211> LENGTH: 98
<212> TYPE: PRT
<213> ORGANISM: Artificial Sequence
<220> FEATURE:
<223> OTHER INFORMATION: Synthetic peptide

<400> SEQUENCE: 45

Ser Ala Leu Ser Ser Pro Thr Thr His Ala Arg Ile Ser Ser His Ala
1               5                   10                  15

Ser Thr Leu Leu Ser Ser Gly Pro Thr Asn Ala Ala Ala Leu Ser Asn
                20                  25                  30

Val Ile Ser Asn Ala Val Ser Gln Val Ser Ala Ser Asn Pro Gly Ser
            35                  40                  45

Ser Ser Cys Asp Val Leu Val Gln Ala Leu Leu Glu Ile Ile Thr Ala
        50                  55                  60

Leu Ile Ser Ile Leu Asp Ser Ser Ser Val Gly Gln Val Asn Tyr Gly
65                  70                  75                  80

Ser Ser Gly Gln Tyr Ala Gln Ile Val Gly Gln Ser Met Gln Asn Ala
                85                  90                  95

Met Gly

<210> SEQ ID NO 46
<211> LENGTH: 97
<212> TYPE: PRT
<213> ORGANISM: Artificial Sequence
<220> FEATURE:
<223> OTHER INFORMATION: Synthetic peptide

<400> SEQUENCE: 46

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
                20                  25                  30

Val Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Ile Val Ser Ala
        50                  55                  60

Cys Val Thr Ile Leu Ser Ser Ser Ile Gly Gln Val Asn Tyr Gly
65                  70                  75                  80

Ala Ala Ser Gln Phe Ala Gln Val Val Gly Gln Ser Val Leu Ser Ala
                85                  90                  95

Phe

<210> SEQ ID NO 47
<211> LENGTH: 82
<212> TYPE: PRT
<213> ORGANISM: Artificial Sequence
<220> FEATURE:
<223> OTHER INFORMATION: Synthetic peptide

<400> SEQUENCE: 47

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
                20                  25                  30
```

```
Val Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

<210> SEQ ID NO 48
<211> LENGTH: 82
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 48

```
Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Xaa Asn Ala Val Ser Gln Ile Gly Ala Ser Asn Pro Gly Leu
            35                  40                  45

Ser Gly Cys Asp Val Leu Leu Xaa Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

<210> SEQ ID NO 49
<211> LENGTH: 71
<212> TYPE: PRT
<213> ORGANISM: Artificial Sequence
<220> FEATURE:
<223> OTHER INFORMATION: Synthetic peptide

<400> SEQUENCE: 49

```
Ser Arg Leu Ser Ser Pro Glu Ala Ala Ser Arg Val Ser Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
            35                  40                  45

Ser Asp Cys Glu Val Leu Val Gln Val Leu Leu Glu Val Val Ser Ala
    50                  55                  60

Leu Val Gln Ile Val Cys Ser
65                  70
```

<210> SEQ ID NO 50
<211> LENGTH: 97
<212> TYPE: PRT
<213> ORGANISM: Artificial Sequence
<220> FEATURE:
<223> OTHER INFORMATION: Synthetic peptide

<400> SEQUENCE: 50

```
Ser Arg Leu Ser Ser Pro Gln Ala Ala Ser Arg Val Ser Ser Ala Val
  1               5                  10                  15

Ser Ser Leu Val Ser Asn Gly Gln Val Asn Val Ala Ala Leu Pro Ser
             20                  25                  30

Ile Ile Ser Ser Leu Ser Ser Ile Ser Ala Ser Ser Thr Ala Ala
         35                  40                  45

Ser Asp Cys Glu Val Leu Val Gln Val Leu Leu Glu Ile Val Ser Ala
 50                  55                  60

Leu Val Gln Ile Val Ser Ser Ala Asn Val Gly Tyr Ile Asn Pro Glu
 65                  70                  75                  80

Ala Ser Gly Ser Leu Asn Ala Val Gly Ser Ala Leu Ala Ala Ala Met
                 85                  90                  95

Gly

<210> SEQ ID NO 51
<211> LENGTH: 93
<212> TYPE: PRT
<213> ORGANISM: Artificial Sequence
<220> FEATURE:
<223> OTHER INFORMATION: Synthetic peptide

<400> SEQUENCE: 51

Asn Arg Leu Ser Ser Ala Gly Ala Ala Ser Arg Val Ser Ser Asn Val
  1               5                  10                  15

Ala Ala Ile Ala Ser Ala Gly Ala Ala Ala Leu Pro Asn Val Ile Ser
             20                  25                  30

Asn Ile Tyr Ser Gly Val Leu Ser Ser Gly Val Ser Ser Ser Glu Ala
         35                  40                  45

Leu Ile Gln Ala Leu Leu Glu Val Ile Ser Ala Leu Ile His Val Leu
 50                  55                  60

Gly Ser Ala Ser Ile Gly Asn Val Ser Ser Val Gly Val Asn Ser Ala
 65                  70                  75                  80

Leu Asn Ala Val Gln Asn Ala Val Gly Ala Tyr Ala Gly
                 85                  90

<210> SEQ ID NO 52
<211> LENGTH: 98
<212> TYPE: PRT
<213> ORGANISM: Artificial Sequence
<220> FEATURE:
<223> OTHER INFORMATION: Synthetic peptide

<400> SEQUENCE: 52

Ser Arg Leu Ser Ser Pro Ser Ala Ala Ala Arg Val Ser Ser Ala Val
  1               5                  10                  15

Ser Leu Val Ser Asn Gly Gly Pro Thr Ser Pro Ala Ala Leu Ser Ser
             20                  25                  30

Ser Ile Ser Asn Val Val Ser Gln Ile Ser Ala Ser Asn Pro Gly Leu
         35                  40                  45

Ser Gly Cys Asp Ile Leu Val Gln Ala Leu Leu Glu Leu Ile Ser Ala
 50                  55                  60

Leu Val His Ile Leu Gly Ser Ala Asn Ile Gly Pro Val Asn Ser Ser
 65                  70                  75                  80

Ser Ala Gly Gln Ser Ala Ser Ile Val Gly Gln Ser Val Tyr Arg Ala
                 85                  90                  95

Leu Ser
```

-continued

```
<210> SEQ ID NO 53
<211> LENGTH: 98
<212> TYPE: PRT
<213> ORGANISM: Artificial Sequence
<220> FEATURE:
<223> OTHER INFORMATION: Synthetic peptide

<400> SEQUENCE: 53

Ser Arg Leu Ser Ser Pro Ala Ala Ser Ser Arg Val Ser Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val Ser Ile Leu Gly Ser Ser Ile Gly Gln Ile Asn Tyr Gly
65                  70                  75                  80

Ala Ser Ala Gln Tyr Thr Gln Met Val Gly Gln Ser Val Ala Gln Ala
                85                  90                  95

Leu Ala

<210> SEQ ID NO 54
<211> LENGTH: 94
<212> TYPE: PRT
<213> ORGANISM: Artificial Sequence
<220> FEATURE:
<223> OTHER INFORMATION: Synthetic peptide

<400> SEQUENCE: 54

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
            20                  25                  30

Ala Leu Asn Ser Leu Val Ser Gln Ile Ser Ala Ser Asn Pro Gly Leu
        35                  40                  45

Ser Gly Cys Asp Ala Leu Val Gln Ala Leu Leu Glu Leu Val Ser Ala
    50                  55                  60

Leu Val Ala Ile Leu Ser Ser Ala Ser Ile Gly Gln Val Asn Val Ser
65                  70                  75                  80

Ser Val Ser Gln Ser Thr Gln Met Ile Ser Gln Ala Leu Ser
                85                  90

<210> SEQ ID NO 55
<211> LENGTH: 100
<212> TYPE: PRT
<213> ORGANISM: Artificial Sequence
<220> FEATURE:
<223> OTHER INFORMATION: Synthetic peptide

<400> SEQUENCE: 55

Ser Arg Leu Ser Ser Pro Gln Ala Ser Ser Arg Val Ser Ser Ala Val
1               5                   10                  15

Ser Asn Leu Val Ser Ser Gly Pro Thr Asn Ser Ala Ala Leu Ser Asn
            20                  25                  30

Thr Ile Ser Asn Val Val Ser Gln Leu Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Ser Ile Gly Gln Val Asn Tyr Gly
```

```
                65                  70                  75                  80
Ser Ala Gly Gln Ala Thr Gln Ile Val Gly Gln Ser Val Ala Gln Ala
                    85                  90                  95

Leu Gly Glu Phe
            100

<210> SEQ ID NO 56
<211> LENGTH: 240
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(18)
<223> OTHER INFORMATION: Up to 10 residues may be absent
<220> FEATURE:
<221> NAME/KEY: misc_feature
<222> LOCATION: (1)..(18)
<223> OTHER INFORMATION: Up to 3 amino acid residues may be an amino
      acid other than Ala
<220> FEATURE:
<221> NAME/KEY: misc_feature
<222> LOCATION: (19)..(48)
<223> OTHER INFORMATION: Up to 18 residues may be absent
<220> FEATURE:
<221> NAME/KEY: misc_feature
<222> LOCATION: (19)..(48)
<223> OTHER INFORMATION: At least 4 to 12 of the residues are Gly
<220> FEATURE:
<221> NAME/KEY: misc_feature
<222> LOCATION: (49)..(66)
<223> OTHER INFORMATION: Up to 10 residues may be absent
<220> FEATURE:
<221> NAME/KEY: misc_feature
<222> LOCATION: (49)..(66)
<223> OTHER INFORMATION: Up to 3 amino acid residues may be an amino
      acid other than Ala
<220> FEATURE:
<221> NAME/KEY: misc_feature
<222> LOCATION: (67)..(96)
<223> OTHER INFORMATION: Up to 18 residues may be absent
<220> FEATURE:
<221> NAME/KEY: misc_feature
<222> LOCATION: (67)..(96)
<223> OTHER INFORMATION: At least 4 to 12 of the residues are Gly
<220> FEATURE:
<221> NAME/KEY: misc_feature
<222> LOCATION: (97)..(114)
<223> OTHER INFORMATION: Up to 10 residues may be absent
<220> FEATURE:
<221> NAME/KEY: misc_feature
<222> LOCATION: (97)..(114)
<223> OTHER INFORMATION: Up to 3 amino acid residues may be an amino
      acid other than Ala
<220> FEATURE:
<221> NAME/KEY: misc_feature
<222> LOCATION: (115)..(144)
<223> OTHER INFORMATION: Up to 18 residues may be absent
<220> FEATURE:
<221> NAME/KEY: misc_feature
<222> LOCATION: (115)..(144)
<223> OTHER INFORMATION: At least 4 to 12 of the residues are Gly
<220> FEATURE:
<221> NAME/KEY: misc_feature
<222> LOCATION: (145)..(162)
<223> OTHER INFORMATION: Up to 10 residues may be absent
<220> FEATURE:
<221> NAME/KEY: misc_feature
<222> LOCATION: (145)..(162)
<223> OTHER INFORMATION: Up to 3 amino acid residues may be an amino
      acid other than Ala
<220> FEATURE:
<221> NAME/KEY: misc_feature
<222> LOCATION: (163)..(192)
<223> OTHER INFORMATION: Up to 18 residues may be absent
<220> FEATURE:
```

```
<221> NAME/KEY: misc_feature
<222> LOCATION: (163)..(192)
<223> OTHER INFORMATION: At least 4 to 12 of the residues are Gly
<220> FEATURE:
<221> NAME/KEY: misc_feature
<222> LOCATION: (193)..(210)
<223> OTHER INFORMATION: Up to 10 residues may be absent
<220> FEATURE:
<221> NAME/KEY: misc_feature
<222> LOCATION: (193)..(210)
<223> OTHER INFORMATION: Up to 3 amino acid residues may be an amino
      acid other than Ala
<220> FEATURE:
<221> NAME/KEY: misc_feature
<222> LOCATION: (211)..(240)
<223> OTHER INFORMATION: Up to 18 residues may be absent
<220> FEATURE:
<221> NAME/KEY: misc_feature
<222> LOCATION: (211)..(240)
<223> OTHER INFORMATION: At least 4 to 12 of the residues are Gly

<400> SEQUENCE: 56

Ala Ala Ala Ala Ala Ala Ala Ala Ala Ala Ala Ala Ala Ala Ala Ala
1               5                   10                  15

Ala Ala Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Ala Ala Ala Ala Ala Ala Ala Ala Ala Ala Ala Ala Ala Ala Ala Ala
 50                  55                  60

Ala Ala Gly Gly Gly Gly Gly Gly Gly Gly Gly Gly Gly Gly Gly Gly
65                   70                  75                  80

Gly Gly Gly Gly Gly Gly Gly Gly Gly Gly Gly Gly Gly Gly Gly Gly
            85                  90                  95

Ala Ala Ala Ala Ala Ala Ala Ala Ala Ala Ala Ala Ala Ala Ala Ala
        100                 105                 110

Ala Ala Gly Gly Gly Gly Gly Gly Gly Gly Gly Gly Gly Gly Gly Gly
    115                 120                 125

Gly Gly Gly Gly Gly Gly Gly Gly Gly Gly Gly Gly Gly Gly Gly Gly
130                 135                 140

Ala Ala Ala Ala Ala Ala Ala Ala Ala Ala Ala Ala Ala Ala Ala Ala
145                 150                 155                 160

Ala Ala Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly Gly
        180                 185                 190

Ala Ala Ala Ala Ala Ala Ala Ala Ala Ala Ala Ala Ala Ala Ala Ala
    195                 200                 205

Ala Ala Gly Gly Gly Gly Gly Gly Gly Gly Gly Gly Gly Gly Gly Gly
210                 215                 220

Gly Gly Gly Gly Gly Gly Gly Gly Gly Gly Gly Gly Gly Gly Gly Gly
225                 230                 235                 240

<210> SEQ ID NO 57
<211> LENGTH: 258
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(18)
<223> OTHER INFORMATION: Up to 10 residues may be absent
<220> FEATURE:
```

```
<221> NAME/KEY: misc_feature
<222> LOCATION: (1)..(18)
<223> OTHER INFORMATION: Up to 3 amino acid residues may be an amino
      acid other than Ala
<220> FEATURE:
<221> NAME/KEY: misc_feature
<222> LOCATION: (19)..(48)
<223> OTHER INFORMATION: Up to 18 residues may be absent
<220> FEATURE:
<221> NAME/KEY: misc_feature
<222> LOCATION: (19)..(48)
<223> OTHER INFORMATION: At least 4 to 12 of the residues are Gly
<220> FEATURE:
<221> NAME/KEY: misc_feature
<222> LOCATION: (49)..(66)
<223> OTHER INFORMATION: Up to 10 residues may be absent
<220> FEATURE:
<221> NAME/KEY: misc_feature
<222> LOCATION: (49)..(66)
<223> OTHER INFORMATION: Up to 3 amino acid residues may be an amino
      acid other than Ala
<220> FEATURE:
<221> NAME/KEY: misc_feature
<222> LOCATION: (67)..(96)
<223> OTHER INFORMATION: Up to 18 residues may be absent
<220> FEATURE:
<221> NAME/KEY: misc_feature
<222> LOCATION: (67)..(96)
<223> OTHER INFORMATION: At least 4 to 12 of the residues are Gly
<220> FEATURE:
<221> NAME/KEY: misc_feature
<222> LOCATION: (97)..(114)
<223> OTHER INFORMATION: Up to 10 residues may be absent
<220> FEATURE:
<221> NAME/KEY: misc_feature
<222> LOCATION: (97)..(114)
<223> OTHER INFORMATION: Up to 3 amino acid residues may be an amino
      acid other than Ala
<220> FEATURE:
<221> NAME/KEY: misc_feature
<222> LOCATION: (115)..(144)
<223> OTHER INFORMATION: Up to 18 residues may be absent
<220> FEATURE:
<221> NAME/KEY: misc_feature
<222> LOCATION: (115)..(144)
<223> OTHER INFORMATION: At least 4 to 12 of the residues are Gly
<220> FEATURE:
<221> NAME/KEY: misc_feature
<222> LOCATION: (145)..(162)
<223> OTHER INFORMATION: Up to 10 residues may be absent
<220> FEATURE:
<221> NAME/KEY: misc_feature
<222> LOCATION: (145)..(162)
<223> OTHER INFORMATION: Up to 3 amino acid residues may be an amino
      acid other than Ala
<220> FEATURE:
<221> NAME/KEY: misc_feature
<222> LOCATION: (163)..(192)
<223> OTHER INFORMATION: Up to 18 residues may be absent
<220> FEATURE:
<221> NAME/KEY: misc_feature
<222> LOCATION: (163)..(192)
<223> OTHER INFORMATION: At least 4 to 12 of the residues are Gly
<220> FEATURE:
<221> NAME/KEY: misc_feature
<222> LOCATION: (193)..(210)
<223> OTHER INFORMATION: Up to 10 residues may be absent
<220> FEATURE:
<221> NAME/KEY: misc_feature
<222> LOCATION: (193)..(210)
<223> OTHER INFORMATION: Up to 3 amino acid residues may be an amino
      acid other than Ala
<220> FEATURE:
<221> NAME/KEY: misc_feature
<222> LOCATION: (211)..(240)
<223> OTHER INFORMATION: Up to 18 residues may be absent
<220> FEATURE:
<221> NAME/KEY: misc_feature
<222> LOCATION: (211)..(240)
<223> OTHER INFORMATION: At least 4 to 12 of the residues are Gly
```

```
<220> FEATURE:
<221> NAME/KEY: misc_feature
<222> LOCATION: (241)..(258)
<223> OTHER INFORMATION: Up to 10 residues may be absent
<220> FEATURE:
<221> NAME/KEY: misc_feature
<222> LOCATION: (241)..(258)
<223> OTHER INFORMATION: Up to 3 amino acid residues may be an amino
      acid other than Ala

<400> SEQUENCE: 57

Ala Ala Ala Ala Ala Ala Ala Ala Ala Ala Ala Ala Ala Ala Ala Ala
1               5                   10                  15

Ala Ala Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Ala Ala Ala Ala Ala Ala Ala Ala Ala Ala Ala Ala Ala Ala Ala Ala
    50                  55                  60

Ala Ala Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
            85                  90                  95

Ala Ala Ala Ala Ala Ala Ala Ala Ala Ala Ala Ala Ala Ala Ala Ala
                100                 105                 110

Ala Ala Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Ala Ala Ala Ala Ala Ala Ala Ala Ala Ala Ala Ala Ala Ala Ala Ala
145                 150                 155                 160

Ala Ala Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly Gly
                180                 185                 190

Ala Ala Ala Ala Ala Ala Ala Ala Ala Ala Ala Ala Ala Ala Ala Ala
        195                 200                 205

Ala Ala Gly Gly Gly Gly Gly Gly Gly Gly Gly Gly Gly Gly Gly Gly
    210                 215                 220

Gly Gly Gly Gly Gly Gly Gly Gly Gly Gly Gly Gly Gly Gly Gly Gly
225                 230                 235                 240

Ala Ala Ala Ala Ala Ala Ala Ala Ala Ala Ala Ala Ala Ala Ala Ala
            245                 250                 255

Ala Ala

<210> SEQ ID NO 58
<211> LENGTH: 240
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(30)
<223> OTHER INFORMATION: Up to 18 residues may be absent
<220> FEATURE:
<221> NAME/KEY: misc_feature
<222> LOCATION: (1)..(30)
<223> OTHER INFORMATION: At least 4 to 12 of the residues are Gly
<220> FEATURE:
<221> NAME/KEY: misc_feature
<222> LOCATION: (31)..(48)
```

```
<223> OTHER INFORMATION: Up to 10 residues may be absent
<220> FEATURE:
<221> NAME/KEY: misc_feature
<222> LOCATION: (31)..(48)
<223> OTHER INFORMATION: Up to 3 amino acid residues may be an amino
      acid other than Ala
<220> FEATURE:
<221> NAME/KEY: misc_feature
<222> LOCATION: (49)..(78)
<223> OTHER INFORMATION: Up to 18 residues may be absent
<220> FEATURE:
<221> NAME/KEY: misc_feature
<222> LOCATION: (49)..(78)
<223> OTHER INFORMATION: At least 4 to 12 of the residues are Gly
<220> FEATURE:
<221> NAME/KEY: misc_feature
<222> LOCATION: (79)..(96)
<223> OTHER INFORMATION: Up to 10 residues may be absent
<220> FEATURE:
<221> NAME/KEY: misc_feature
<222> LOCATION: (79)..(96)
<223> OTHER INFORMATION: Up to 3 amino acid residues may be an amino
      acid other than Ala
<220> FEATURE:
<221> NAME/KEY: misc_feature
<222> LOCATION: (97)..(126)
<223> OTHER INFORMATION: Up to 18 residues may be absent
<220> FEATURE:
<221> NAME/KEY: misc_feature
<222> LOCATION: (97)..(126)
<223> OTHER INFORMATION: At least 4 to 12 of the residues are Gly
<220> FEATURE:
<221> NAME/KEY: misc_feature
<222> LOCATION: (127)..(144)
<223> OTHER INFORMATION: Up to 10 residues may be absent
<220> FEATURE:
<221> NAME/KEY: misc_feature
<222> LOCATION: (127)..(144)
<223> OTHER INFORMATION: Up to 3 amino acid residues may be an amino
      acid other than Ala
<220> FEATURE:
<221> NAME/KEY: misc_feature
<222> LOCATION: (145)..(174)
<223> OTHER INFORMATION: Up to 18 residues may be absent
<220> FEATURE:
<221> NAME/KEY: misc_feature
<222> LOCATION: (145)..(174)
<223> OTHER INFORMATION: At least 4 to 12 of the residues are Gly
<220> FEATURE:
<221> NAME/KEY: misc_feature
<222> LOCATION: (175)..(192)
<223> OTHER INFORMATION: Up to 10 residues may be absent
<220> FEATURE:
<221> NAME/KEY: misc_feature
<222> LOCATION: (175)..(192)
<223> OTHER INFORMATION: Up to 3 amino acid residues may be an amino
      acid other than Ala
<220> FEATURE:
<221> NAME/KEY: misc_feature
<222> LOCATION: (193)..(222)
<223> OTHER INFORMATION: Up to 18 residues may be absent
<220> FEATURE:
<221> NAME/KEY: misc_feature
<222> LOCATION: (193)..(222)
<223> OTHER INFORMATION: At least 4 to 12 of the residues are Gly
<220> FEATURE:
<221> NAME/KEY: misc_feature
<222> LOCATION: (223)..(240)
<223> OTHER INFORMATION: Up to 10 residues may be absent
<220> FEATURE:
<221> NAME/KEY: misc_feature
<222> LOCATION: (223)..(240)
<223> OTHER INFORMATION: Up to 3 amino acid residues may be an amino
      acid other than Ala

<400> SEQUENCE: 58

Gly Gly Gly Gly Gly Gly Gly Gly Gly Gly Gly Gly Gly Gly Gly Gly
1               5                   10                  15
```

Gly Gly Gly Gly Gly Gly Gly Gly Gly Gly Gly Ala Ala
        20                  25                  30

Ala Ala Ala Ala Ala Ala Ala Ala Ala Ala Ala Ala Ala
        35                  40                  45

Gly Gly Gly Gly Gly Gly Gly Gly Gly Gly Gly Gly Gly
50                  55                  60

Gly Gly Gly Gly Gly Gly Gly Gly Gly Gly Gly Ala Ala
65                  70                  75                  80

Ala Ala Ala Ala Ala Ala Ala Ala Ala Ala Ala Ala Ala
        85                  90                  95

Gly Gly Gly Gly Gly Gly Gly Gly Gly Gly Gly Gly Gly
        100                 105                 110

Gly Gly Gly Gly Gly Gly Gly Gly Gly Gly Gly Ala Ala
        115                 120                 125

Ala Ala Ala Ala Ala Ala Ala Ala Ala Ala Ala Ala Ala
        130                 135                 140

Gly Gly Gly Gly Gly Gly Gly Gly Gly Gly Gly Gly Gly
145                 150                 155                 160

Gly Gly Gly Gly Gly Gly Gly Gly Gly Gly Gly Ala Ala
        165                 170                 175

Ala Ala Ala Ala Ala Ala Ala Ala Ala Ala Ala Ala Ala
        180                 185                 190

Gly Gly Gly Gly Gly Gly Gly Gly Gly Gly Gly Gly Gly
        195                 200                 205

Gly Gly Gly Gly Gly Gly Gly Gly Gly Gly Gly Ala Ala
        210                 215                 220

Ala Ala Ala Ala Ala Ala Ala Ala Ala Ala Ala Ala Ala Ala Ala
225                 230                 235                 240

<210> SEQ ID NO 59
<211> LENGTH: 270
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(30)
<223> OTHER INFORMATION: Up to 18 residues may be absent
<220> FEATURE:
<221> NAME/KEY: misc_feature
<222> LOCATION: (1)..(30)
<223> OTHER INFORMATION: At least 4 to 12 of the residues are Gly
<220> FEATURE:
<221> NAME/KEY: misc_feature
<222> LOCATION: (31)..(48)
<223> OTHER INFORMATION: Up to 10 residues may be absent
<220> FEATURE:
<221> NAME/KEY: misc_feature
<222> LOCATION: (31)..(48)
<223> OTHER INFORMATION: Up to 3 amino acid residues may be an amino
      acid other than Ala
<220> FEATURE:
<221> NAME/KEY: misc_feature
<222> LOCATION: (49)..(78)
<223> OTHER INFORMATION: Up to 18 residues may be absent
<220> FEATURE:
<221> NAME/KEY: misc_feature
<222> LOCATION: (49)..(78)
<223> OTHER INFORMATION: At least 4 to 12 of the residues are Gly
<220> FEATURE:
<221> NAME/KEY: misc_feature
<222> LOCATION: (79)..(96)
<223> OTHER INFORMATION: Up to 10 residues may be absent
<220> FEATURE:
<221> NAME/KEY: misc_feature

```
<222> LOCATION: (79)..(96)
<223> OTHER INFORMATION: Up to 3 amino acid residues may be an amino
      acid other than Ala
<220> FEATURE:
<221> NAME/KEY: misc_feature
<222> LOCATION: (97)..(126)
<223> OTHER INFORMATION: Up to 18 residues may be absent
<220> FEATURE:
<221> NAME/KEY: misc_feature
<222> LOCATION: (97)..(126)
<223> OTHER INFORMATION: At least 4 to 12 of the residues are Gly
<220> FEATURE:
<221> NAME/KEY: misc_feature
<222> LOCATION: (127)..(144)
<223> OTHER INFORMATION: Up to 10 residues may be absent
<220> FEATURE:
<221> NAME/KEY: misc_feature
<222> LOCATION: (127)..(144)
<223> OTHER INFORMATION: Up to 3 amino acid residues may be an amino
      acid other than Ala
<220> FEATURE:
<221> NAME/KEY: misc_feature
<222> LOCATION: (145)..(174)
<223> OTHER INFORMATION: Up to 18 residues may be absent
<220> FEATURE:
<221> NAME/KEY: misc_feature
<222> LOCATION: (145)..(174)
<223> OTHER INFORMATION: At least 4 to 12 of the residues are Gly
<220> FEATURE:
<221> NAME/KEY: misc_feature
<222> LOCATION: (175)..(192)
<223> OTHER INFORMATION: Up to 10 residues may be absent
<220> FEATURE:
<221> NAME/KEY: misc_feature
<222> LOCATION: (175)..(192)
<223> OTHER INFORMATION: Up to 3 amino acid residues may be an amino
      acid other than Ala
<220> FEATURE:
<221> NAME/KEY: misc_feature
<222> LOCATION: (193)..(222)
<223> OTHER INFORMATION: Up to 18 residues may be absent
<220> FEATURE:
<221> NAME/KEY: misc_feature
<222> LOCATION: (193)..(222)
<223> OTHER INFORMATION: At least 4 to 12 of the residues are Gly
<220> FEATURE:
<221> NAME/KEY: misc_feature
<222> LOCATION: (223)..(240)
<223> OTHER INFORMATION: Up to 10 residues may be absent
<220> FEATURE:
<221> NAME/KEY: misc_feature
<222> LOCATION: (223)..(240)
<223> OTHER INFORMATION: Up to 3 amino acid residues may be an amino
      acid other than Ala
<220> FEATURE:
<221> NAME/KEY: misc_feature
<222> LOCATION: (241)..(270)
<223> OTHER INFORMATION: Up to 18 residues may be absent
<220> FEATURE:
<221> NAME/KEY: misc_feature
<222> LOCATION: (241)..(270)
<223> OTHER INFORMATION: At least 4 to 12 of the residues are Gly

<400> SEQUENCE: 59

Gly Gly Gly Gly Gly Gly Gly Gly Gly Gly Gly Gly Gly Gly Gly Gly
 1               5                   10                  15

Gly Gly Gly Gly Gly Gly Gly Gly Gly Gly Gly Gly Gly Gly Ala Ala
                20                  25                  30

Ala Ala Ala Ala Ala Ala Ala Ala Ala Ala Ala Ala Ala Ala Ala Ala
            35                  40                  45

Gly Gly Gly Gly Gly Gly Gly Gly Gly Gly Gly Gly Gly Gly Gly Gly
        50                  55                  60

Gly Gly Gly Gly Gly Gly Gly Gly Gly Gly Gly Gly Gly Gly Ala Ala
65                  70                  75                  80
```

```
Ala Ala Ala Ala Ala Ala Ala Ala Ala Ala Ala
            85                  90                  95
Gly Gly Gly Gly Gly Gly Gly Gly Gly Gly Gly Gly Gly
            100                 105                 110
Gly Gly Gly Gly Gly Gly Gly Gly Gly Gly Gly Ala Ala
            115                 120                 125
Ala Ala Ala Ala Ala Ala Ala Ala Ala Ala Ala Ala
            130                 135                 140
Gly Gly Gly Gly Gly Gly Gly Gly Gly Gly Gly Gly Gly
145                 150                 155                 160
Gly Gly Gly Gly Gly Gly Gly Gly Gly Gly Gly Ala Ala
            165                 170                 175
Ala Ala Ala Ala Ala Ala Ala Ala Ala Ala Ala Ala
            180                 185                 190
Gly Gly Gly Gly Gly Gly Gly Gly Gly Gly Gly Gly Gly
            195                 200                 205
Gly Gly Gly Gly Gly Gly Gly Gly Gly Gly Gly Ala Ala
            210                 215                 220
Ala Ala Ala Ala Ala Ala Ala Ala Ala Ala Ala Ala
225                 230                 235                 240
Gly Gly Gly Gly Gly Gly Gly Gly Gly Gly Gly Gly Gly
            245                 250                 255
Gly Gly Gly Gly Gly Gly Gly Gly Gly Gly Gly Gly Gly
            260                 265                 270

<210> SEQ ID NO 60
<211> LENGTH: 18
<212> TYPE: PRT
<213> ORGANISM: Artificial Sequence
<220> FEATURE:
<223> OTHER INFORMATION: Synthetic peptide

<400> SEQUENCE: 60

Ala Ser Ala Ser Ala Ala Ala Ser Ala Ala Ser Thr Val Ala Asn Ser
1               5                   10                  15

Val Ser

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide

<400> SEQUENCE: 61

Ala Ser Ala Ala Ser Ala Ala Ala
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide

<400> SEQUENCE: 62

Gly Ser Ala Met Gly Gln Gly Ser
1               5

<210> SEQ ID NO 63
<211> LENGTH: 6
```

```
<212> TYPE: PRT
<213> ORGANISM: Artificial Sequence
<220> FEATURE:
<223> OTHER INFORMATION: Synthetic peptide

<400> SEQUENCE: 63

Leu Val Pro Arg Gly Ser
1               5

<210> SEQ ID NO 64
<211> LENGTH: 4
<212> TYPE: PRT
<213> ORGANISM: Artificial Sequence
<220> FEATURE:
<223> OTHER INFORMATION: Synthetic peptide

<400> SEQUENCE: 64

Asp Asp Asp Lys
1

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Leu Gly Val Leu Phe Gln Gly Pro
1               5

<210> SEQ ID NO 66
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Glu or Asp

<400> SEQUENCE: 66

Ile Xaa Gly Arg
1

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is Gly or Ser

<400> SEQUENCE: 67

Glu Xaa Xaa Tyr Xaa Gln Xaa
1               5

<210> SEQ ID NO 68
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Glu Asn Leu Tyr Phe Gln Gly
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide

<400> SEQUENCE: 69

Glu Asp Asn Leu Tyr Phe Gln Gly
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic peptide

<400> SEQUENCE: 70

Leu Glu Val Leu Phe Gln Gly Pro
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic peptide

<400> SEQUENCE: 71

Gly Arg Gly Gln Gly
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic peptide

<400> SEQUENCE: 72

Gly Gln Gly Gln Gly
1               5
```

SPIDER SILK PROTEINS AND METHODS FOR PRODUCING SPIDER SILK PROTEINS

This application is a Continuation of application Ser. No. 13/598,119, filed on Aug. 29, 2012, which is a Continuation of application Ser. No. 13/441,118, filed Apr. 6, 2012, now U.S. Pat. No. 8,278,416, which is a Continuation of application Ser. No. 12/087,289 filed Jun. 30, 2008, now U.S. Pat. No. 8,173,772, which is the National phase of PCT International Application No. PCT/SE2006/001505 filed on Dec. 28, 2006. This application also claims priority to Patent Application No. 0502932-7 filed in Sweden on Dec. 30, 2005. All of the above applications are hereby expressly incorporated by reference into the present application.

TECHNICAL FIELD OF THE INVENTION

The present invention relates to the field of recombinant production of proteins. More specifically, the present invention is concerned with recombinant production of spider silk proteins. The present invention provides novel isolated major ampullate spidroin proteins and major ampullate spidroin fusion proteins, as well as methods and polynucleic acid molecules for producing such proteins. There is also provided polymers of the major ampullate spidroin proteins and methods for producing such polymers.

BACKGROUND OF THE INVENTION

Spider silks are nature's high-performance polymers, obtaining extraordinary toughness due to a combination of strength and elasticity. Up to seven specialized glands exist in spiders, which produce a variety of silk fiber types with different mechanical properties and functions. Dragline silk, produced by the major ampullate gland, is the toughest fiber, and on a weight basis it outperforms man-made materials, such as high tensile steel and Kevlar. The properties of dragline silk are attractive in development of new materials for medical or technical purposes.

Dragline silk consists of two main polypeptides, mostly referred to as major ampullate spidroin (MaSp) 1 and 2, but to ADF-3 and ADF-4 in *Araneus diadematus*. These proteins have apparent molecular masses in the range of 200-720 kDa, depending on sample age and conditions of analysis, but no full-length dragline spider silk gene has yet been reported. The properties of dragline silk polypeptides are discussed in Huemmerich, D. et al. Novel assembly properties of recombinant spider dragline silk proteins. Curr. Biol. 14, 2070-2074 (2004). The known dragline silk spidroins are composed of highly iterated blocks of alternating alanine-rich segments, forming crystalline β-sheets in the fiber, and glycine-rich segments which are more flexible and mainly lack ordered structure. The C-terminal region is non-repetitive, highly conserved between species, and adopts α-helical conformation. The N-terminal region of dragline silk proteins has not been characterized until very recently, revealing an N-terminal domain that is highly conserved between different spidroins, and also between different spider species (Rising, A. et al. N-terminal nonrepetitive domain common to dragline, flagelliform, and cylindriform spider silk proteins. Biomacromolecules 7, 3120-3124 (2006)).

The mechanical properties of dragline silk varies between species; *Euprosthenops* sp dragline silk is stiffer, stronger (requires more force to break) and less extendible than dragline silk from e.g. *Araneus diadematus* or *Nephila clavipes*. Dragline silk from *Euprosthenops* sp appears to have a greater proportion of crystalline β-sheet structure than dragline silk from *Araneus diadematus*, most likely due to that the *Euprosthenops* sp MaSp has the highest polyalanine content among all species analyzed so far (Pouchkina-Stantcheva, N. N. & McQueen-Mason, S. J. Molecular studies of a novel dragline silk from a nursery web spider, *Euprosthenops* sp. (Pisauridae). Comp Biochem Physiol B Biochem Mol Biol 138, 371-376 (2004)).

Attempts to produce artificial spider silks have employed natural or synthetic gene fragments encoding dragline silk proteins, since no full-length gene has yet been reported. Recombinant dragline silk proteins have been expressed in various systems including bacteria, yeast, mammalian cells, plants, insect cells, transgenic silkworms and transgenic goats. See e.g. Lewis, R. V. et al. Expression and purification of a spider silk protein: a new strategy for producing repetitive proteins. Protein Expr. Purif. 7, 400-406 (1996); Fahnestock, S. R. & Irwin, S. L. Synthetic spider dragline silk proteins and their production in *Escherichia coli*. Appl. Microbiol. Biotechnol. 47, 23-32 (1997); Arcidiacono, S. et al. Purification and characterization of recombinant spider silk expressed in *Escherichia coli*. Appl. Microbiol. Biotechnol. 49, 31-38 (1998); Fahnestock, S. R. & Bedzyk, L. A. Production of synthetic spider dragline silk protein in *Pichia pastoris*. Appl. Microbiol. Biotechnol. 47, 33-39 (1997); and Lazaris, A. et al. Spider silk fibers spun from soluble recombinant silk produced in mammalian cells. Science 295, 472-476 (2002).

WO 2004/016651 (The University of York) discloses nucleic acid sequences coding for internal, repetitive parts of MaSp1 proteins from *Euprosthenops* sp. No protein is expressed.

Huemmerich, D. et al. Primary structure elements of spider dragline silks and their contribution to protein solubility. Biochemistry 43, 13604-13612 (2004) discloses a synthetic gene, "$(AQ)_{12}NR3$", coding for repetitive Ala-rich and Gly/Gln-rich fragments and a non-repetitive fragment, all derived from ADF3 from *Araneus*. The gene is expressed into a soluble protein (59.8 kD, >528 aa), which aggregates but does not form polymers or fibers. The alanine content of the protein is 10-15%.

WO 03/057727 discloses expression of soluble recombinant silk polypeptides in mammalian cell lines and animals. One expressed silk polypeptide (ADF-3; 60 kD, 652 aa) consists of a repetitive unit and a non-repetitive hydrophilic domain. Another expressed silk polypeptide (ADF-3 His; 63 kD, 677 aa) consists of a repetitive unit, a non-repetitive hydrophilic domain, a c-myc epitope and a six-Histidine tag. The repetitive unit has a low content of Ala (10-20%). The obtained silk polypeptides exhibit poor solubility in aqueous media and/or form precipitates. Since the obtained silk polypeptides do not polymerize spontaneously, spinning is required to obtain polymers or fibers.

Several factors complicate the expression of dragline silk proteins. Due to the highly repetitive nature of the genes, and the concomitant restricted amino acid composition of the proteins, transcription and translation errors occur. Depletion of tRNA-pools in microbial expression systems, with subsequent discontinuous translation, leading to premature termination of protein synthesis might be another reason. Other reasons discussed for truncation of protein synthesis are secondary structure formation of the mRNA, and recombination of the genes. Native MaSp genes larger than 2.5 kb have been shown to be instable in bacterial hosts. Additionally, there are difficulties in maintaining the recombinant silk proteins in soluble form, since both natural-derived dragline silk fragments and designed block copolymers, especially MaSp1/ADF-4-derived proteins, easily self-assemble into amorphous aggregates, causing precipitation and loss of protein.

See Huemmerich, D. et al. Primary structure elements of spider dragline silks and their contribution to protein solubility. Biochemistry 43, 13604-13612 (2004) and Lazaris, A. et al. Spider silk fibers spun from soluble recombinant silk produced in mammalian cells. Science 295, 472-476 (2002).

SUMMARY OF THE INVENTION

It is an object of the present invention to provide a novel spider silk protein, which can provide spider silk fibers.

It is another object of the present invention to provide a water-soluble spider silk protein, which can readily be manipulated to self-polymerize into fibers at wish. This allows for unique applications, such as culturing of eukaryotic cells on the fibers. Furthermore, this property allows for all the following steps to be undertaken under physiological conditions, which decreases the risk for toxicity and protein denaturation.

It is yet another object of the present invention to provide fibers of a novel spider silk protein.

It is one object of the present invention to provide spider silk proteins in large scale, which proteins can readily be manipulated to self-polymerize into fibers at wish.

It is also an object of the invention to provide methods of producing silk proteins and fibers of spider silk proteins.

For these and other objects that will be evident from the following disclosure, the present invention provides according to one aspect an isolated major ampullate spidroin protein, wherein the protein consists of from 150 to 420 amino acid residues and is defined by the formula REP-CT, wherein REP is a protein fragment having from 80 to 300 amino acid residues, wherein said fragment is selected from the group of L(AG)$_n$L (SEQ ID NO: 17), L(AG)$_n$AL (SEQ ID NO: 18), L(GA)$_n$L (SEQ ID NO: 19), L(GA)$_n$GL (SEQ ID NO: 20), wherein n is an integer from 4 to 8;
each individual A segment is an amino acid sequence of from 8 to 18 amino acid residues, wherein from 0 to 3 of the amino acid residues are not Ala, and the remaining amino acid residues are Ala; each individual G segment is an amino acid sequence of from 12 to 30 amino acid residues, wherein at least 40% of the amino acid residues are Gly; and each individual L segment is a linker amino acid sequence of from 0 to 20 amino acid residues; and CT is a protein fragment having from 70 to 120 amino acid residues, which fragment is a C-terminal fragment derived from a major ampullate spidroin protein, or a derivative thereof.

The present invention is based on the identification of a protein motif, which is sufficient to form silk-like fibers, and the use of said motif for construction of recombinant MaSp proteins, which are possible to produce in suitable hosts, such as bacteria, preferably *E. coli*.

In certain embodiments according to the invention, each individual A segment has at least 80% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3; amino acid residues 31-42, 61-75, 90-104, 122-135 and 153-171 of SEQ ID NO: 9; amino acid residues 12-25, 46-60, 75-88, 112-119, 150-158 and 173-180 of SEQ ID NO: 13; amino acid residues 31-42 of SEQ ID NO: 14; and amino acid residues 122-135 of SEQ ID NO: 15. In specific embodiments, each individual A segment is an amino acid sequence selected from this group of amino acid sequences.

In some embodiments according to the invention, each individual G segment has at least 80% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3; SEQ ID NO: 5; SEQ ID NO: 6; SEQ ID NO: 7; amino acid residues 11-30, 43-60, 76-89, 105-121 and 136-152 of SEQ ID NO: 9; and amino acid residues 1-11, 26-45, 61-74, 89-111, 120-149 and 159-172 of SEQ ID NO: 13. In specific embodiments, each individual G segment is identical to an amino acid sequence selected from this group of amino acid sequences.

In certain embodiments according to the invention, said CT fragment has at least 50% identity to SEQ ID NO: 8 or at least 80% identity to an amino acid sequence selected from the group consisting of SEQ ID NO: 4, amino acid residues 172-269 of SEQ ID NO: 9, amino acid residues 181-276 of SEQ ID NO: 13 and amino acid residues 172-269 of SEQ ID NO: 16 as well as any amino acid sequence of FIG. 3, in particular the MaSp1 sequences of FIG. 3. In specific embodiments, said CT fragment is an amino acid sequence selected from this group of amino acid sequences.

In certain embodiments according to the invention, the content of lipopolysaccharides (LPS) and other pyrogens in the isolated major ampullate spidroin protein is 1 endotoxin unit (EU)/mg protein or lower.

According to another aspect, the present invention provides an isolated fusion protein consisting of a first protein fragment, which is a major ampullate spidroin protein, and a second protein fragment, wherein said second protein fragment comprises a fusion partner and a cleavage agent recognition site, wherein said first protein fragment is coupled via said cleavage agent recognition site to said fusion partner.

The present invention provides an isolated fusion protein selected from the group of X-REP-CT, and REP-CT-X, wherein REP and CT are protein fragments according to the invention; and X is a protein fragment comprising a fusion partner and a cleavage agent recognition site; wherein the combined protein fragment REP-CT is coupled via said cleavage agent recognition site to said fusion partner.

In certain embodiments according to the invention, the content of LPS and other pyrogens in the isolated fusion protein is 1 EU/mg protein or lower.

According to yet another aspect, the present invention provides a method of producing a major ampullate spidroin protein according to the invention, comprising the steps of: (i) providing a solution of a fusion protein according to the invention in a liquid medium, (ii) adding to said liquid medium a suitable cleaving agent for achieving cleavage of the fusion protein at the cleavage agent recognition site, and thereby obtaining the major ampullate spidroin protein; and optionally (iii) isolating the major ampullate spidroin protein obtained in step (ii) from said liquid medium.

The present invention also provides a method of producing a polymer of a major ampullate spidroin protein according to the invention, comprising the steps of: (i) providing a solution of a fusion protein according to the invention in a liquid medium, (ii) adding to said liquid medium a suitable cleaving agent for achieving cleavage of the fusion protein at the cleavage agent recognition site, and thereby obtaining the major ampullate spidroin protein; (iii) allowing the major ampullate spidroin protein obtained in step (ii) to polymerize in the liquid medium; and optionally (iv) isolating the polymer obtained in step (iii) from said liquid medium. In a preferred method, said step (iii) further comprises providing an interface between said liquid medium and another phase selected from the group consisting of a gas phase, a liquid phase and a solid phase, wherein said polymerizing initiates at said interface or in a region surrounding said interface. In a preferred method, said liquid medium is an aqueous medium and said other phase is selected from the group consisting of air and water-immiscible organic solvents.

According to another aspect, the present invention provides an isolated polynucleic acid molecule comprising a nucleic acid sequence which encodes a major ampullate spidroin protein according to the invention, or its complementary nucleic acid sequence.

According to yet another aspect, the present invention provides an isolated polynucleic acid molecule comprising a nucleic acid sequence which encodes a fusion protein according to the invention, or its complementary nucleic acid sequence.

Another aspect of the invention resides in a method of producing a soluble fusion protein according to the invention, comprising the steps of: (i) expressing a polynucleic acid molecule encoding a soluble fusion protein according to the invention in a suitable host; and (ii) isolating the soluble fusion protein obtained in step (i). Optionally, said step (ii) of isolating the soluble fusion protein involves removal of LPS and other pyrogens.

The present invention also provides a method of producing a major ampullate spidroin protein according to the invention, comprising the steps of: (i) expressing a polynucleic acid molecule encoding a soluble fusion protein according to the invention in a suitable host; (ii) isolating the soluble fusion protein obtained in step (i); (iii) providing a solution of said soluble fusion protein obtained in step (ii) in a liquid medium, (iv) adding to said liquid medium a suitable cleaving agent for achieving cleavage of the fusion protein at the cleavage agent recognition site, and thereby obtaining the major ampullate spidroin protein; and optionally (v) isolating the major ampullate spidroin protein obtained in step (iv) from said liquid medium. Further optionally, said step (ii) of isolating the soluble fusion protein, and optionally step (v) of isolating the major ampullate spidroin protein, involve(s) removal of LPS and other pyrogens.

The present invention further provides a method of producing a polymer of a major ampullate spidroin protein according to the invention, comprising the steps of: (i) expressing a polynucleic acid molecule encoding a soluble fusion protein according to the invention in a suitable host; (ii) isolating the soluble fusion protein obtained in step (i); (iii) providing a solution of said soluble fusion protein obtained in step (ii) in a liquid medium, (iv) adding to said liquid medium a suitable cleaving agent for achieving cleavage of the fusion protein at the cleavage agent recognition site, and thereby obtaining the major ampullate spidroin protein; (v) allowing the major ampullate spidroin protein obtained in step (iv) to polymerize in the liquid medium; and optionally (vi) isolating the polymer obtained in step (v) from said liquid medium. In a preferred method, said step (v) further comprises providing an interface between said liquid medium and another phase selected from the group consisting of a gas phase, a liquid phase and a solid phase, wherein said polymerizing initiates at said interface or in a region surrounding said interface. In a preferred method, said liquid medium is an aqueous medium and said other phase is selected from the group consisting of air and water-immiscible organic solvents.

According to another aspect, the present invention provides a polymer of a major ampullate spidroin protein according to the invention. The present invention also provides a polymer of a major ampullate spidroin protein obtainable by a method according to the invention. In a preferred embodiment, said polymer is a fiber. In other preferred embodiments, said polymer forms a structure selected from the group consisting of a foam, a gel, a mesh or a film.

According to yet another aspect, the present invention provides a novel use of a protein fragment comprising a fusion partner and a cleavage agent recognition site for the manufacture of a fusion protein comprising said protein fragment coupled via said cleavage agent recognition site to a spider silk protein fragment. In preferred embodiments, said spider silk protein fragment consists of from 150 to 420 amino acid residues.

According to a final aspect, the present invention provides an isolated polynucleic acid molecule comprising a nucleic acid sequence selected from the group consisting of SEQ ID NO: 1 and nucleic acid sequences encoding SEQ ID NOS: 2-16, or its complementary nucleic acid sequences. The present invention also provides use of the isolated polynucleic acid molecule for the manufacture of a non-natural gene encoding a spider silk protein.

BRIEF DESCRIPTION OF THE DRAWINGS

FIG. 1 is an alignment of the segments within the repetitive part of *Euprosthenops australis* MaSp1 protein, i.e. SEQ ID NO: 3.

FIG. 3 is an alignment of C-terminal regions of MaSp1 and MaSp2, illustrating their conserved nature (SEQ ID NOS: 24-55).

DETAILED DISCLOSURE OF THE INVENTION

Figure 2:
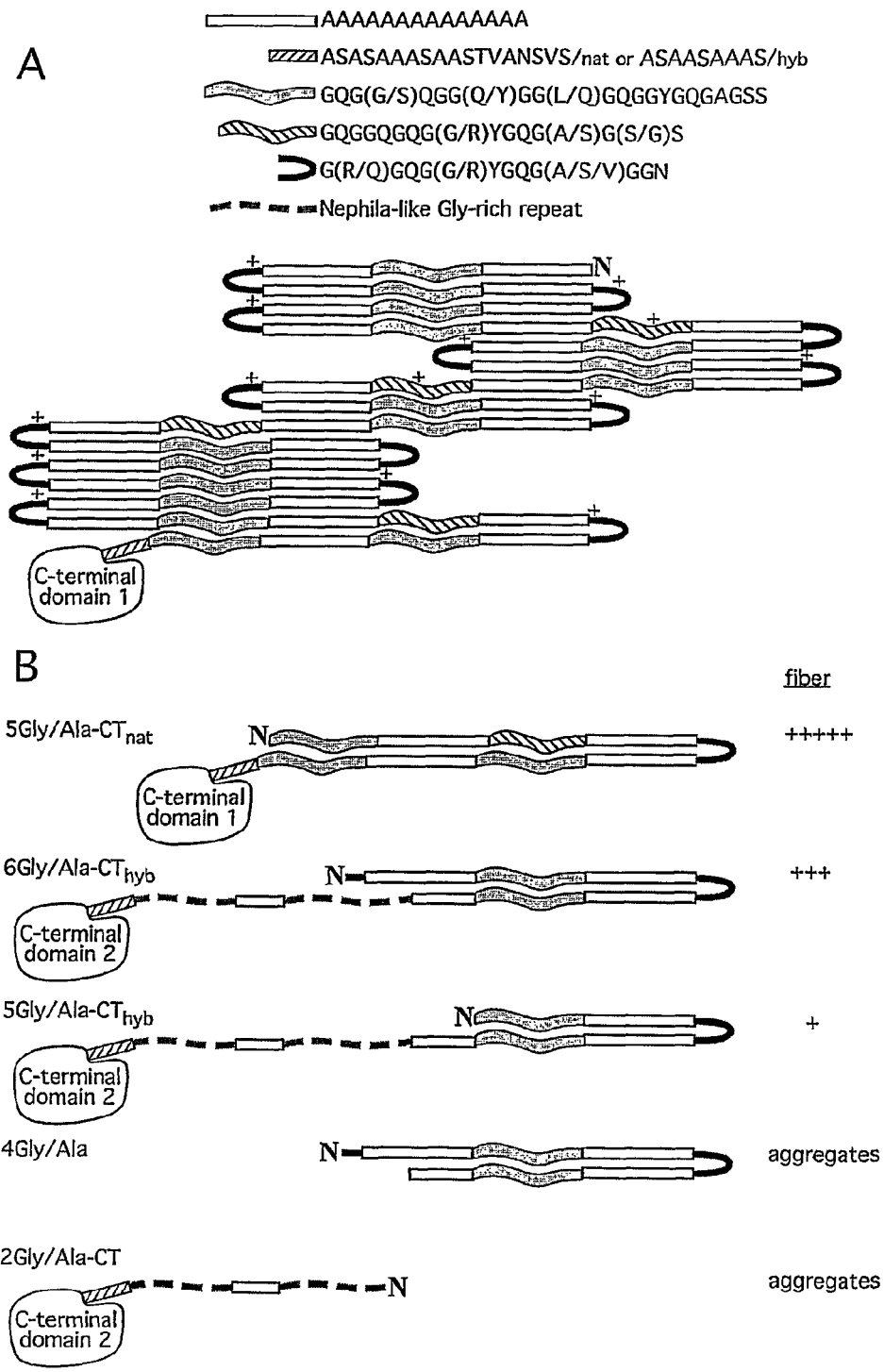
FIG. 2A illustrates a schematic, predicted structural organization of the repetitive part of *Euprosthenops australis* MaSp1 protein (SEQ ID NO: 3). The various peptide segments shown correspond to SEQ ID NOS: 21-23 and 5-6, respectively.
FIG. 2B illustrates schematic, predicted structural organizations of the spidroin proteins constructed according to examples 5-8 (SEQ ID NOS: 9-13).

The present invention is generally based on the identification of a spidroin protein motif, which is sufficient for recombinant production of spider silk fibers. The motif is based on the deduced amino acid sequence from cloning and sequencing of a partial major spidroin 1 (MaSp1) cDNA from *Euprosthenops australis*. It follows that the isolated MaSp1 cDNA is useful as a starting point for construction of novel spidroin genes, such as those reported herein. The polymers which are formed from the proteins resulting from the novel spidroin cDNAs are useful for their physical properties, especially the useful combination of high strength, elasticity and light weight. They are also useful for their ability to support cell adherence and growth. The properties of dragline silk are attractive in development of new materials for medical or technical purposes. In particular, spider silks according to the invention are useful in medical devices, such as implants and medical products, such as wound closure systems, band-aids, sutures, wound dressings, and scaffolds for tissue engineering and guided cell regeneration. Spider silks according to the invention are also particularly useful for use as textile or fabric, such as in parachutes, bulletproof clothing, seat belts, etc.

The term "fiber" as used herein relates to polymers having a thickness of at least 1 µm, preferably macroscopic polymers that are visible to the human eye, i.e. having a thickness of at least 1 µm, and have a considerable extension in length compared to its thickness, preferably above 5 mm. The term "fiber" does not encompass unstructured aggregates or precipitates.

The terms "major ampullate spidroin proteins", "spidroin proteins" are used interchangeably throughout the description and encompass all known major ampullate spidroin proteins, typically abbreviated "MaSp", or "ADF" in the case of *Araneus diadematus*. These major ampullate spidroin proteins are generally of two types, 1 and 2. These terms furthermore include the new proteins according to the invention, as defined in the appended claims, and other non-natural proteins with a high degree of identity and/or similarity to the known major ampullate spidroin proteins.

The present inventors have utilized the identified spidroin protein motif for construction of novel gene constructs, coding for non-natural spidroin proteins. It has been found that a major ampullate spidroin protein consisting of from 150 to 420 amino acid residues, i.e. more than or equal to 150, preferably more than or equal to 220, preferably more than or equal to 250, and less than or equal to 420, preferably less than or equal to 380 amino acid residues, preferably less than or equal to 320 amino acid residues, preferably less than or equal to 280 amino acid residues, such as 220-360 amino acid residues, can be recombinantly produced, e.g. in bacteria or other suitable production organisms. The resulting spidroin proteins spontaneously form macroscopic silk fibers according to the invention. This is a surprising result, since the naturally occurring spidroin proteins and previously known, recombinantly produced, fiber-forming spidroin proteins are considerably longer than the proteins according to the invention. Moreover, the naturally occurring spidroin proteins and previously known, recombinantly produced, fiber-forming spidroin proteins tend to contain a large number of internal repeats and require use of spinning and/or harsh solvents for polymerization.

It is here for the first time shown that spidroin proteins can spontaneously form fibers in vitro. The data presented herein also show that only a fraction of the spidroin sequence need to be present to dictate fiber formation. Moreover, a species hybrid containing a *Euprosthenops* repetitive domain and a *Nephila* non-repetitive C-terminal domain (c.f. Example 6C) forms fibers as well, indicating that the fiber-forming potential of this motif is robust.

In its general aspect, the major ampullate spidroin protein according to the invention is defined by the formula REP-CT. The REP protein fragment and the CT protein fragment are covalently coupled, typically via a peptide bond.

The protein fragment REP has a repetitive character, alternating between alanine-rich stretches and glycine-rich stretches. The REP fragment generally contains more than 80, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

$L(AG)_nL$ (SEQ ID NO: 17), such as $LA_1G_1A_2G_2A_3G_3A_4G_4A_5G_5L$ (SEQ ID NO: 56);
$L(AG)_nAL$ (SEQ ID NO: 18), such as $LA_1G_1A_2G_2A_3G_3A_4G_4A_5G_5A_6L$ (SEQ ID NO: 57);
$L(GA)_nL$ (SEQ ID NO: 19), such as $LG_1A_1G_2A_2G_3A_3G_4A_4G_5A_5L$ (SEQ ID NO: 58); or
$L(GA)_nGL$ (SEQ ID NO: 20), such as $LG_1A_1G_2A_2G_3A_3G_4A_4G_5A_5G_6L$ (SEQ ID NO: 59).

It follows that it is not critical whether an alanine-rich or a glycine-rich segment is adjacent to the N-terminal or C-terminal linker segments. It is preferred that n is an integer from 4 to 8, more preferred from 4 to 6, i.e. n=4, n=5 or n=6.

In preferred embodiments, the alanine content of the REP fragment according to the invention is above 20%, preferably above 25%, more preferably above 30%, and below 50%, preferably below 40%, more preferably below 35%. This is advantageous, since it is contemplated that a higher alanine content provides a stiffer and/or stronger and/or less extendible fiber. The reason for this is likely to be that a higher alanine content is associated with a higher content of β-sheet structures in the fiber. Thus, in a preferred embodiment, the β-sheet content in a polymer, such as a fiber, of the major ampullate spidroin protein according to the invention is above 50%, i.e. more than 50% of the secondary structure of the protein is in β-sheet form.

In certain embodiments, the REP fragment is void of proline residues, i.e. there are no Pro residues in the REP fragment.

Now turning to the segments that constitute the REP fragment according to the invention, it shall be emphasized that each segment is individual, i.e. any two A segments, any two G segments or any two L segments of a specific REP fragment may be identical or may not be identical. Thus, it is not a general feature of the invention that each type of segment is identical within a specific REP fragment. Rather, the following disclosure provides the skilled person with guidelines how to design individual segments and gather them into a REP fragment, which is a part of a functional spidroin protein according to the invention.

It has been concluded from experimental data presented herein that each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In a preferred embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

Figure 1:
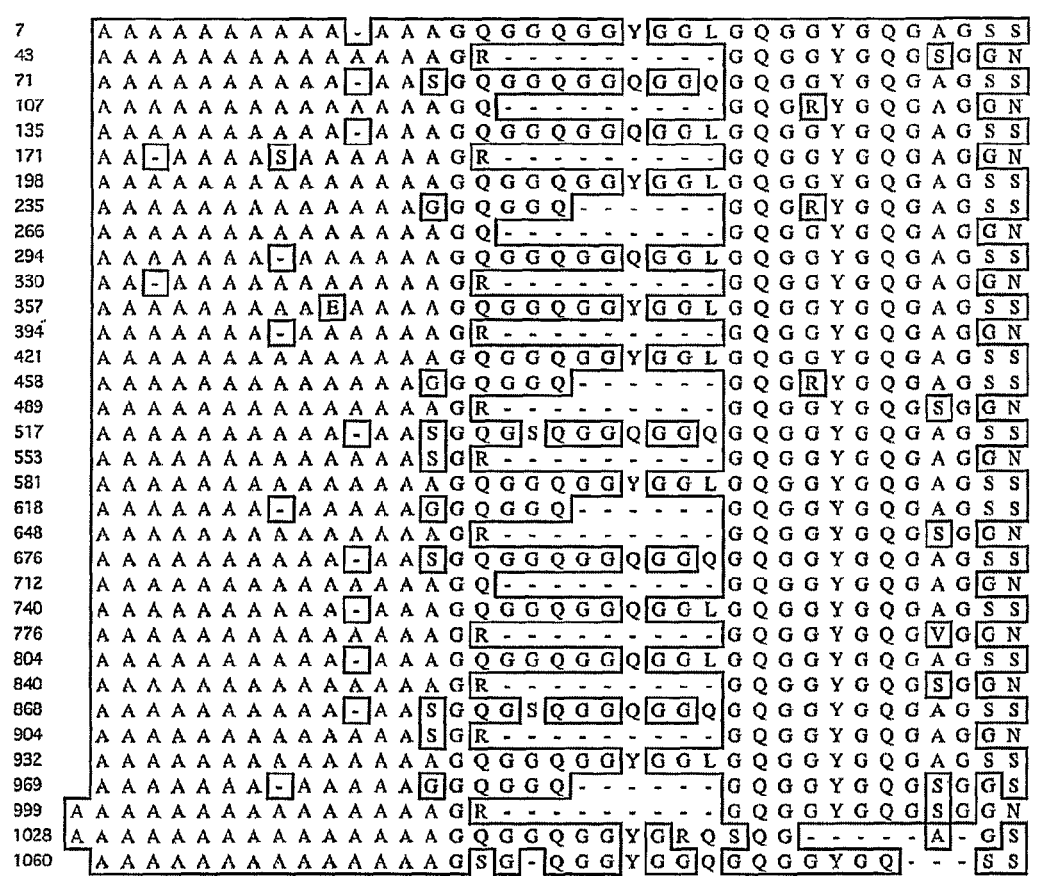

It is preferred that each individual A segment has at least 80% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3. Each sequence of this group corresponds to a segment of the naturally occurring sequence of *Euprosthenops australis* MaSp1 protein, which is deduced from cloning of the corresponding cDNA, see Examples 1-2 and FIG. 1-2A. Alternatively, each individual A segment has at least 80% identity to an amino acid sequence selected from the group of amino acid residues 31-42, 61-75, 90-104, 122-135 and 153-171 of SEQ ID NO: 9, amino acid residues 12-25, 46-60, 75-88, 112-119, 150-158 and 173-180 of SEQ ID NO: 13, amino acid residues 31-42 of SEQ ID NO: 14 and amino acid residues 122-135 of SEQ ID NO: 15. Each sequence of this group corresponds to a segment of expressed, non-natural spidroin proteins according to the invention, which proteins have capacity to form silk fibers under appropriate conditions. See Examples 5-8, 12 and FIG. 2B. Without wishing to be bound by any particular theory, it is envisaged that A segments according to the invention form helical structures or beta sheets.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In preferred embodiments according to the invention, each individual A segment has at least 90%, more preferably 95%, most preferably 100%, identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3; amino acid residues 31-42, 61-75, 90-104, 122-135 and 153-171 of SEQ ID NO: 9; amino acid residues 12-25, 46-60, 75-88, 112-119, 150-158 and 173-180 of SEQ ID NO: 13; amino acid residues 31-42 of SEQ ID NO: 14; and amino acid residues 122-135 of SEQ ID NO: 15. Thus, in certain embodiments according to the invention, each individual A segment is identical to an amino acid sequence selected from the above-mentioned amino acid segments.

Furthermore, it has been concluded from experimental data presented herein that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3. Each sequence of this group corresponds to a segment of the naturally occurring sequence of *Euprosthenops australis* MaSp1 protein, which is deduced from cloning of the corresponding cDNA, see Examples 1-2 and FIG. 1-2A. Alternatively, each individual G segment has at least 80% identity to an amino acid sequence selected from the group of amino acid residues 11-30, 43-60, 76-89, 105-121 and 136-152 of SEQ ID NO: 9 and amino acid residues 1-11, 26-45, 61-74, 89-111, 120-149 and 159-172 of SEQ ID NO: 13. Each sequence of this group corresponds to a segment of expressed, non-natural spidroin proteins according to the invention, which proteins have capacity to form silk fibers under appropriate conditions. See Examples 5-8, 12 and FIG. 2B.

In preferred embodiments according to the invention, each individual G segment has at least 90%, more preferably 95%, most preferably 100%, identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3; amino acid residues 11-30, 43-60, 76-89, 105-121 and 136-152 of SEQ ID NO: 9; and amino acid residues 1-11, 26-45, 61-74, 89-111, 120-149 and 159-172 of SEQ ID NO: 13. Thus, in certain embodiments according to the invention, each individual G segment is identical to an amino acid sequence selected from the above-mentioned amino acid segments.

In certain embodiments, the first two amino acid residues of each G segment according to the invention are not -Gln-Gln-.

In certain embodiments, the position corresponding to the conserved Tyr residue (i.e. corresponding to position 16 in SEQ ID NO: 5, position 10 in SEQ ID NO: 6 and position 7 in SEQ ID NO: 7) is not Phe in any G segment according to the invention.

In certain embodiments, the position corresponding to the conserved Tyr residue (i.e. corresponding to position 16 in SEQ ID NO: 5, position 10 in SEQ ID NO: 6 and position 7 in SEQ ID NO: 7) is Tyr in each G segment according to the invention.

It follows that certain embodiments of the proteins according to the invention display a combination of the above-mentioned limitations, i.e. the first two amino acid residues of each G segment according to the invention are not -Gln-Gln-, and the conserved Tyr residue (i.e. corresponding to position 16 in SEQ ID NO: 5, position 10 in SEQ ID NO: 6 and position 7 in SEQ ID NO: 7) is Tyr in each G segment according to the invention. In certain embodiments, the above-mentioned limitations, taken separately or in any possible combination, can be further combined with the limitation that the REP fragment is void of proline residues, as discussed hereinabove.

With reference to FIGS. 1-2 and Examples 3-4, there are the three subtypes of the G segment according to the invention. This classification is based upon careful analysis of the *Euprosthenops australis* MaSp1 protein sequence (FIGS. 1-2A), and the information has been employed and verified in the construction of novel, non-natural spider silk proteins (FIG. 2B).

The first subtype of the G segment according to the invention is represented by the amino acid one letter consensus sequence GQG(G/S)QGG(Q/Y)GG (L/Q)GQGGYGQGA GSS, as shown in FIG. 2A and SEQ ID NO: 5. This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 3; amino acid residues 11-30, 105-121 and 136-152 of SEQ ID NO: 9; and amino acid residues 26-45 and 89-111 of SEQ ID NO: 13. Alternative G segments of this first subtype are amino acid residues 120-149 and 159-172 of SEQ ID NO: 13. In certain embodiments, the first two amino acid residues of each G segment of this first subtype according to the invention are not -Gln-Gln-.

The second subtype of the G segment according to the invention is represented by the amino acid one letter consensus sequence GQGGQGQG(G/R)Y GQG(A/S)G(S/G)S, as shown in FIG. 2A and SEQ ID NO: 6. This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 3; and amino acid residues 43-60 of SEQ ID NO: 9.

The third subtype of the G segment according to the invention is represented by the amino acid one letter consensus sequence G(R/Q)GQG(G/R)YGQG (A/S/V)GGN, as shown in FIG. 2A and SEQ ID NO: 7. This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 3; amino acid residues 76-89 of SEQ ID NO: 9; and amino acid residues 61-74 of SEQ ID NO: 13. An alternative G segment of this third subtype is amino acid residues 1-11 of SEQ ID NO: 13.

Thus, in preferred embodiments, each individual G segment has at least 80%, preferably 90%, more preferably 95%, identity to an amino acid sequence selected from SEQ ID NO: 5, SEQ ID NO: 6 and SEQ ID NO: 7.

In a preferred embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . (SEQ ID NO: 56) In another preferred embodiment of the REP fragment, one G segment of the second subtype interrupts the G segment regularity via an insertion, e.g. . . . $A_1G_{short}A_2G_{long}A_3G_{mid}A_4G_{short}A_5G_{long}$ . . . (SEQ ID NO: 56)

Each individual L segment represents an optional linker amino acid sequence, which may contain from 0 to 20 amino acid residues, such as from 0 to 10 amino acid residues. While this segment is optional and not functionally critical for the spidroin protein, its presence still allows for fully functional spidroin proteins, forming spider silk fibers according to the invention. There are also linker amino acid sequences present in the repetitive part (SEQ ID NO: 3) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in FIG. 2A, a linker segment arranged at the C-terminal part of the REP fragment can be represented by the amino acid one letter consensus sequences ASASAAASAA STVANSVS (SEQ ID NO: 60) and ASAASAAA (SEQ ID NO: 61), which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS (SEQ ID NO: 62), which is rich in glycine and has a high degree of similarity to G segments according to the invention.

Representative L segments are amino acid residues 1-6 and 1093-1110 of SEQ ID NO: 3; amino acid residues 1-10 and 153-171 of SEQ ID NO: 9; and amino acid residues 173-180 of SEQ ID NO: 13, but the skilled person in the art will readily recognize that there are many suitable alternative amino acid sequences for these segments. In one embodiment of the REP fragment according to the invention, one of the L segments contains 0 amino acids, i.e. one of the L segments is void. In another embodiment of the REP fragment according to the invention, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

Figure 3:
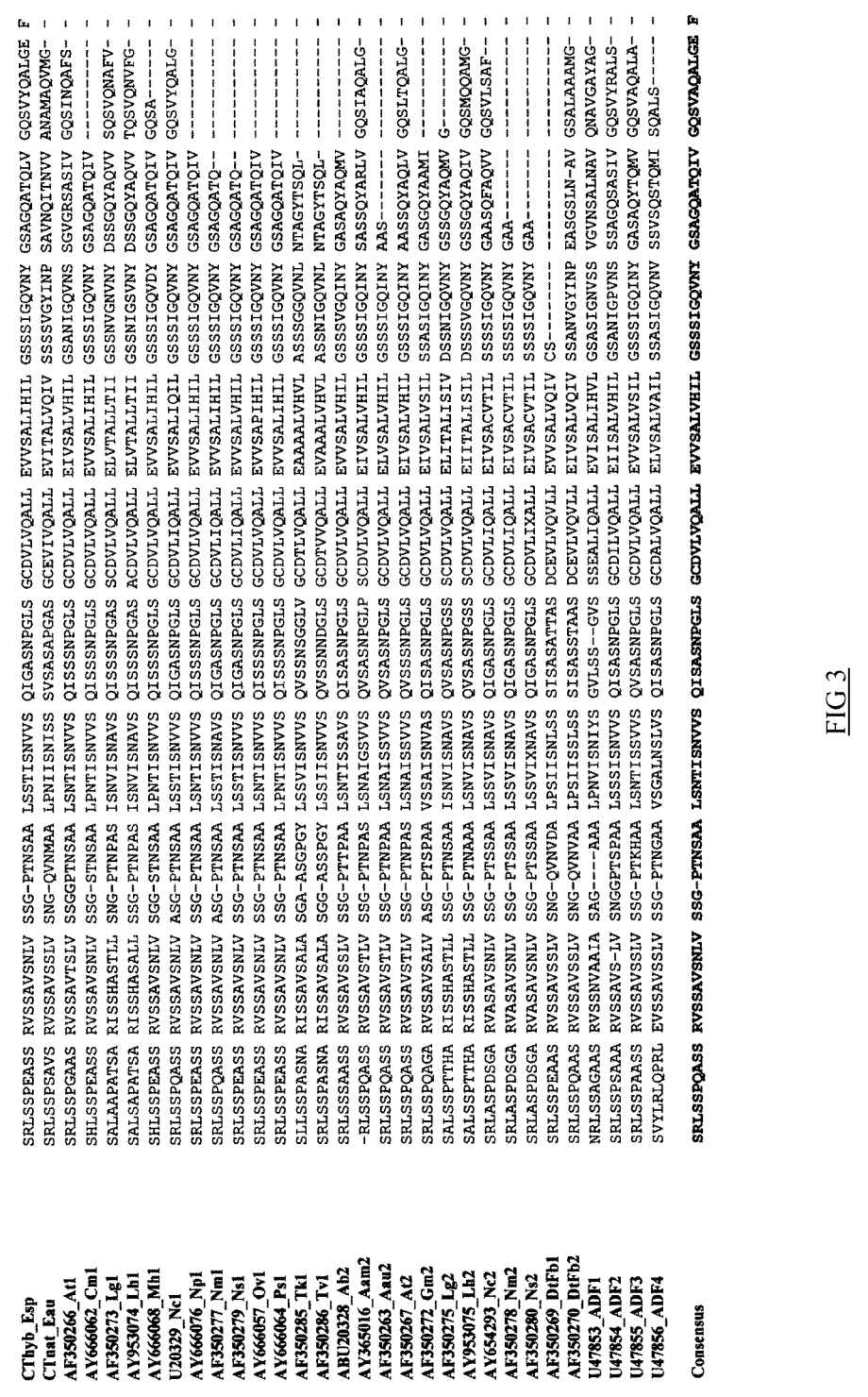

The C-terminal (CT) fragment of the spidroin protein according to the invention has a high degree of similarity to the C-terminal amino acid sequence of spidroin proteins. As shown in FIG. 3, this amino acid sequence is well conserved among various species and spidroin proteins, including MaSp1 and MaSp2. It is demonstrated in the following examples that it is not critical which specific CT fragment is present in spidroin proteins according to the invention, as long as the CT fragment is not entirely missing. Thus, the CT fragment according to the invention can be selected from any of the amino acid sequences shown in FIG. 3 or sequences with a high degree of similarity. It is notable that the $CT_{hyb}$ fragment of SEQ ID NO: 13 has 96% identity to the consensus amino acid sequence SEQ ID NO: 8, while the $CT_{nat}$ fragment of SEQ ID NO: 9 displays only 59% identity to the consensus amino acid sequence SEQ ID NO: 8. This illustrates that a wide variety of C-terminal sequences can be used in the spidroin protein according to the invention.

The sequence of the CT fragment according to the invention has at least 50% identity, preferably at least 60% identity, to the consensus amino acid sequence SEQ ID NO: 8, which is based on the amino acid sequences of FIG. 3. In a preferred embodiment, the sequence of the CT fragment according to the invention has at least 65% identity, preferably at least 70% identity, to amino acid residues 1-71 of the consensus amino acid sequence SEQ ID NO: 8. In preferred embodiments, the CT fragment according to the invention has furthermore 70%, preferably 80%, similarity to the consensus amino acid sequence SEQ ID NO: 8, or amino acid residues 1-71 thereof.

Representative CT fragments according to the invention are the *Euprosthenops australis* sequence SEQ ID NO: 4, the *Euprosthenops australis*-derived amino acid residues 172-269 of SEQ ID NO: 9 and amino acid residues 181-276 of SEQ ID NO: 13, alleged to be derived from *Euprosthenops* sp (Pouchkina-Stantcheva, N. N. & McQueen-Mason, S. J. Molecular studies of a novel dragline silk from a nursery web spider, *Euprosthenops* sp. (Pisauridae). Comp Biochem Physiol B Biochem Mol Biol 138, 371-376 (2004)), but with a high degree of similarity to MaSp1 from *Nephila clavipes* and *Nephila senegalensis*. Thus, according to a preferred aspect of the invention, the CT fragment has at least 80% identity to SEQ ID NO: 4, amino acid residues 172-269 of SEQ ID NO: 9, amino acid residues 181-276 of SEQ ID NO: 13, amino acid residues 172-269 of SEQ ID NO: 16 or any individual MaSp1/ADF-4 amino acid sequence of FIG. 3 and Example 4. In preferred aspects of the invention, the CT fragment has at least 90%, such as at least 95% identity, to SEQ ID NO: 4, amino acid residues 172-269 of SEQ ID NO: 9, amino acid residues 181-276 of SEQ ID NO: 13, amino acid residues 172-269 of SEQ ID NO: 16 or any individual MaSp1/ADF-4 amino acid sequence of FIG. 3 and Example 4. In preferred aspects of the invention, the CT fragment is identical to SEQ ID NO: 4, amino acid residues 172-269 of SEQ ID NO: 9, amino acid residues 181-276 of SEQ ID NO: 13, amino acid residues 172-269 of SEQ ID NO: 16 or any individual MaSp1/ADF-4 amino acid sequence of FIG. 3 and Example 4.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

According to another aspect, the present invention provides an isolated fusion protein consisting of a first protein fragment, which is a major ampullate spidroin protein, preferably consisting of from 150 to 420 amino acid residues, and a second protein fragment, which comprises a fusion partner and a cleavage agent recognition site. The first protein fragment is coupled via the cleavage agent recognition site to the fusion partner, i.e. the fusion partner can be cleaved off by treating the fusion protein with a suitable cleaving agent under appropriate conditions, providing a major ampullate spidroin protein, preferably consisting of from 150 to 420 amino acid residues. An advantage with this fusion protein is that large amounts thereof can be produced in solution, preferably in a physiological medium, typically a buffered aqueous medium, such as a 10-100 mM Tris-HCl buffer, pH 6-9, without causing precipitation and other production problems when produced in suitable hosts, such as bacteria, preferably *E. coli*. The fusion proteins in the solution are soluble for long time periods, typically days or weeks, which facilitates large-scale production and decreases the risk for protein aggregation. By the terms "soluble" and "in solution" is meant that the protein is not visibly aggregated and does not precipitate from the solvent at 60 000×g. At wish, the fusion proteins in the solution can be subjected to cleavage using a suitable cleaving agent, providing a major ampullate spidroin protein which spontaneously forms silk fibers.

In a preferred aspect, the present invention provides an isolated fusion protein selected from the group of X-REP-CT and REP-CT-X, preferably X-REP-CT. REP and CT are protein fragments according to the invention, implying that the resulting MaSp protein of the form REP-CT is a MaSp protein according to the invention. X is a protein fragment comprising a fusion partner and a cleavage agent recognition site as defined above. The combined protein fragment REP-CT is coupled via the cleavage agent recognition site to the fusion partner.

Fusion partners according to the invention include any protein fragment which improves the solubility and/or stability of its partner protein fragment, here the MaSp protein according to the invention. The fusion partner also provides a suitable handle for affinity purification. Without being limited thereto, examples of fusion partners according to the invention include thioredoxin, maltose-binding protein, glutathione S-transferase (GST), MTB32-C, Gb1, ZZ and Nus A. The skilled person is well aware of alternative suitable fusion partners. In a preferred embodiment of the invention, the fusion partner is a thioredoxin moiety (ThrX) in combination with a His tag and an S tag. In one preferred embodiment of the invention, the fusion partner is a ThrX moiety in combination with two His tags, i.e. His-tag/ThrX/His-tag. In another preferred embodiment of the invention, the fusion partner is a thioredoxin moiety (ThrX).

The cleavage agent recognition site is situated at that X protein fragment terminal which is coupled to the MaSp protein fragment, so that cleavage at the recognition site results in a MaSp protein and a fusion partner. Without being limited thereto, examples of the cleavage agent recognition site according to the invention include a thrombin recognition site having the amino acid sequence LVPRGS (SEQ ID NO: 63) (cleaves between R and G); an enterokinase recognition site having the amino acid sequence DDDK (SEQ ID NO: 64) (cleaves after K); an hydroxylamine recognition site having the amino acid sequence NG (cleaves between N and G); a HRV 3C protease recognition site having the amino acid sequence LGVLFQGP (SEQ ID NO: 65)(cleaves between Q and G); a Factor Xa recognition site having the amino acid sequence I(E/D)GR (SEQ ID NO: 66) (cleaves after R); a TEV recognition site having the amino acid sequence EXX-YXQ(G/S) (SEQ ID NO: 67), commonly ENLYFQG (SEQ ID NO: 68)(cleaves between Q and G/S), an Ac-TEV recognition site having the amino acid sequence EDNLYFQG (SEQ ID NO: 69)(cleaves between Q and G); and a PreScission recognition site having the amino acid sequence LEVLFQGP (SEQ ID NO: 70) (cleaves between Q and G). Other suitable recognition sites are the cleavage sites for trypsin, endoproteinase, V8 protease, pepsin and CNBr. Further examples of suitable cleavage recognition sites are well within the reach of the skilled person. In a preferred embodiment of the invention, the cleavage agent recognition site is a thrombin recognition site.

In a preferred embodiment, the X fragment according to the invention has the structure ThrX/His-tag/S-tag/thrombin cleavage site, and the X fragment is coupled to the N-terminal of the REP-CT protein fragment according to the invention.

In one preferred embodiment, the X fragment according to the invention has the structure His-tag/ThrX/His-tag/thrombin cleavage site, and the X fragment is coupled to the N-terminal of the REP-CT protein fragment according to the invention.

According to another aspect, the present invention provides a method of producing a major ampullate spidroin protein according to the invention. In the first step, a solution of a fusion protein according to the invention in a liquid medium is provided. Preferably, the fusion protein does not aggregate, and therefore, resolubilization procedures are not required. The fusion protein can be recombinantly produced and purified using an affinity handle at the fusion protein, such as a His-tag or any suitable epitope in the fusion protein. The liquid medium can be any suitable medium, preferably a physiological medium, typically a buffered aqueous medium, such as a 10-100 mM Tris-HCl buffer, pH 6-9. In the second step, a cleavage agent according to the invention is added to the liquid medium in order to achieve cleavage of the fusion protein at the cleavage agent recognition site. As disclosed above, the major ampullate spidroin protein according to the invention is thereby obtained. In a third, optional step, the thus obtained major ampullate spidroin protein is isolated from the liquid medium using suitable isolation techniques, such as chromatography and/or filtration.

According to yet another aspect, the present invention provides a method of producing a polymer of a major ampullate spidroin protein according to the invention. In the first step, a solution of a fusion protein according to the invention in a liquid medium is provided. Preferably, the fusion protein does not aggregate, and therefore, resolubilization procedures are not required. The fusion protein can be recombinantly produced and purified using an affinity handle at the fusion protein, such as a His-tag or any suitable epitope in the fusion protein. The liquid medium can be any suitable medium, preferably a physiological medium, typically a buffered aqueous medium, such as a 10-100 mM Tris-HCl buffer, pH 6-9. In the second step, a cleavage agent according to the invention is added to the liquid medium in order to achieve cleavage of the fusion protein at the cleavage agent recognition site. As disclosed above, the major ampullate spidroin protein according to the invention is thereby obtained. In the third step, the thus obtained major ampullate spidroin protein is allowed to polymerize in the liquid medium. The polymerization typically initiates at the interface between two different phases, such as liquid/air, liquid/solid, and water/oil interfaces. Thus, this third step may also further comprise providing an interface between the liquid medium and another phase. The other phase is selected from the group consisting of a gas phase, a liquid phase and a solid phase. As detailed above, the liquid medium is typically an aqueous medium, and suitable other phases are for instance air and water-immiscible organic solvents, such as oil, e.g. mineral oil suitable for PCR reactions. The presence of the resulting interface stimulates polymerization at the interface or in the region surrounding the interface, which region extends into the liquid medium, such that said polymerizing initiates at said interface or in said interface region. Preferred interfaces include water/air and water/oil interfaces. Polymerization typically occurs spontaneously within minutes or a few hours, such as within from 1 min to 5 h, upon incubation at room temperature. In a fourth, optional step, the thus obtained polymer of the major ampullate spidroin protein is isolated from the liquid medium using suitable isolation techniques.

As discussed above, fiber formation is induced by proteolytic release of the miniature spidroin from the fusion protein. If the cleavage reaction is performed in a tube that is gently wagged from side to side, a fiber is formed at the air-water interface along the tube. The tube can be made of any suitable material, such as plastic or glass. If the cleavage mixture is allowed to stand still, a film is formed at the air-water interface. If oil is added on top of the aqueous cleavage mixture, a film is formed at the oil-water interface, either if allowed to stand still or if wagged. If the cleavage mixture is foamed, e.g. by bubbling of air or whipping, the foam is stable and solidifies if allowed to dry.

Using the method(s) of the present invention, it is possible to recombinantly produce large amounts of fusion proteins according the invention, which can be cleaved and allowed to polymerize at desire. This provides a better control of the polymerization process and allows for optimization of parameters for obtaining silk fibers with desirable properties.

The major ampullate spidroin protein according to the invention is typically recombinantly produced using a variety of suitable hosts. According to another aspect, the present invention therefore provides an isolated polynucleic acid molecule comprising a nucleic acid sequence which encodes a major ampullate spidroin protein according to the invention, or its complementary nucleic acid sequence, such as SEQ ID NOS: 9-13, preferably SEQ ID NOS: 9, 12 and 13. These polynucleic acid molecules as well as polynucleic acid molecules coding for the various proteins disclosed herein (SEQ ID NOS: 2-16) may also be useful in further developments of non-natural spidroin proteins or production systems therefor.

The fusion protein according to the invention is typically recombinantly produced using a variety of suitable hosts, such as bacteria, yeast, mammalian cells, plants, insect cells, and transgenic animals. It is preferred that the fusion protein according to the invention is produced in bacteria.

According to another aspect, the present invention therefore provides an isolated polynucleic acid molecule comprising a nucleic acid sequence which encodes a fusion protein according to the invention, or its complementary nucleic acid sequence. The polynucleic acid molecule may also be useful in further developments of non-natural spidroin proteins or production systems therefor.

Polynucleic acid molecules according to the invention can be DNA molecules, including cDNA molecules, or RNA molecules. As the skilled person is well aware, a nucleic acid sequence may as well be described by its complementary nucleic acid sequence. Therefore, nucleic acid sequences that are complementary to the nucleic acid sequences according to the invention are also encompassed by the protective scope of the invention.

According to one aspect, the present invention provides a method of producing a soluble fusion protein according to the invention. In the first step, a polynucleic acid molecule which encodes a fusion protein according to the invention is expressed in a suitable host. In the second step, the thus obtained soluble fusion protein in step is isolated, e.g. using chromatography and/or filtration. Optionally, said second step of isolating the soluble fusion protein involves removal of LPS and other pyrogens.

The present invention further provides a method of producing a major ampullate spidroin protein according to the invention. In the first step, a polynucleic acid molecule which encodes a fusion protein according to the invention is expressed in a suitable host. In the second step, the thus obtained soluble fusion protein is isolated, e.g. using chromatography and/or filtration. In the third step, a solution of the isolated fusion protein is provided, and in the fourth step, a suitable cleaving agent is added to the liquid medium. This achieves cleavage of the fusion protein at the cleavage agent recognition site, and thereby provides the major ampullate spidroin protein. In an optional fifth step, the thus obtained major ampullate spidroin protein is isolated from the liquid medium. Further optionally, said second step of isolating the soluble fusion protein, and optionally the fifth step of isolating the major ampullate spidroin protein, involve(s) removal of LPS and other pyrogens.

The present invention also provides a method of producing a polymer of a major ampullate spidroin protein according to the invention. In the first step, a polynucleic acid molecule which encodes a fusion protein according to the invention is expressed in a suitable host. In the second step, the thus obtained soluble fusion protein is isolated, e.g. using chromatography and/or filtration. In the third step, a solution of the isolated fusion protein is provided, and in the fourth step, a suitable cleaving agent is added to the liquid medium. This achieves cleavage of the fusion protein at the cleavage agent recognition site, and thereby provides the major ampullate spidroin protein. In the fifth step, the thus obtained major ampullate spidroin protein is allowed to polymerize in the liquid medium. The polymerization typically initiates at the interface between two different phases, such as liquid/air, liquid/solid, and water/oil interfaces. Thus, this fifth step may also further comprise providing an interface between the liquid medium and another phase. The other phase is selected from the group consisting of a gas phase, a liquid phase and a solid phase. As detailed above, the liquid medium is typically an aqueous medium, and suitable other phases are for instance air and water-immiscible organic solvents, such as oil, e.g. mineral oil suitable for PCR reactions. The presence of the resulting interface stimulates polymerization at the interface or in the region surrounding the interface, which region extends into the liquid medium, such that said polymerizing initiates at said interface or in said interface region. Preferred interfaces include water/air and water/oil interfaces. Polymerization typically occurs spontaneously within minutes or a few hours, such as within from 1 min to 5 h, upon incubation at room temperature. In an optional sixth step, the thus obtained polymer is isolated from the liquid medium.

In order to obtain a protein with low pyrogenic content, which is an obligate for usage as a biomaterial in vivo, a purification protocol optimized for removal of lipopolysaccharides (LPS) has been developed. To avoid contamination by released LPS, the producing bacterial cells are subjected to washing steps with altering $CaCl_2$ and EDTA. After cell lysis, all subsequent purifications steps are performed in low conductivity buffers in order to minimize hydrophobic interactions between the target protein and LPS. The LPS content is further minimized by passage of the protein solution through an Endotrap column, which has a ligand that specifically adsorbs LPS. To assure constant low content of LPS and other pyrogens, all batches are analyzed using an in vitro pyrogen test (IPT) and/or a *Limulus amebocyte* lysate (LAL) kinetic assay. Although produced in a gram-negative bacterial host, the recombinant spidroin proteins can be purified so that residual levels of LPS and other pyrogens are below the limits required for animal tests, i.e. below 25 EU/implant. In certain embodiments according to the invention, the content of LPS and other pyrogens in the isolated fusion protein is 1 EU/mg protein or lower. In certain embodiments according to the invention, the content of LPS and other pyrogens in the isolated major ampullate spidroin protein is 1 EU/mg protein or lower, preferably 0.25 EU/mg protein or lower.

According to another aspect, the present invention provides a polymer of a major ampullate spidroin protein according to the invention. In a preferred embodiment, the polymer of this protein is obtainable by any one of the methods therefor according to the invention.

In preferred embodiments, the β-sheet content of the polymer of the major ampullate spidroin protein according to the invention is above 50%, i.e. more than 50% of the secondary structure of the polymer of this protein is in β-sheet form. This is advantageous, since it is contemplated that a higher content of β-sheet structures provides a stiffer and/or stronger and/or less extendible fiber.

It is preferable that the polymer of the spidroin protein according to the invention is a fiber with a macroscopic size, i.e. with a diameter above 1 μm, preferably above 10 μm and a length above 5 mm. It is preferred that the fiber has a diameter in the range of 10-400 μm, preferably 60-120 μm, and a length in the range of 0.5-300 cm, preferably 1-100 cm. Other preferred ranges are 0.5-30 cm and 1-20 cm. It is also preferred that the polymer of the spidroin protein according to the invention has a tensile strength above 1 MPa, preferably above 2 MPa, more preferably 10 MPa or higher. It is preferred that the polymer of the spidroin protein according to the invention has a tensile strength above 100 MPa, more preferably 200 MPa or higher. The fiber has the capacity to remain intact during physical manipulation, i.e. can be used for spinning, weaving, twisting, crocheting and similar procedures.

In other preferred embodiments, the polymer of the spidroin protein according to the invention forms a foam, a gel, a mesh or a film.

According to yet another aspect, the present invention provides a novel use of a protein fragment comprising a fusion partner and a cleavage agent recognition site for the manufacture of a fusion protein. The fusion protein is comprising said protein fragment and a spider silk protein fragment according to the invention, and the two fragments are coupled via said cleavage agent recognition site. The spider silk protein fragment preferably consists of from 150 to 420 amino acid residues.

The present invention will in the following be further illustrated by the following non-limiting examples.

EXAMPLES

Example 1

Cloning and Sequencing of *Euprosthenops australis* MaSp1 cDNA

The major ampullate glands from approximately 100 adult female *Euprosthenops australis* spiders, collected in South Africa, were used to construct a custom-made pDONR222-based CloneMiner cDNA library (Invitrogen, Paisley, UK). cDNA clones encoding the MaSp1 protein were obtained by screening the library with a cDNA probe encoding an alanine- and glycine-rich fragment originating from *Euprosthenops* spiders of unknown subspecies. Colony blotting and detection were performed with an ECL direct labelling and detection system (Amersham Biosciences, Uppsala, Sweden) according to the manufacturer's instruction.

One single clone was chosen for further characterization. To obtain full length sequence of the cDNA insert from this clone, nested deletions were made using the Erase-a-Base System (Promega, Southampton, UK), and sequencing was performed on a MegaBase 1000 instrument (Amersham Biosciences).

The resulting 3.8 kb cDNA (SEQ ID NO: 1) encodes a MaSp1 protein (SEQ ID NO: 2) of 1207 amino acid residues, containing a repetitive fragment of 34 alanine- and glycine-rich segments (SEQ ID NO: 3), and a C-terminal non-repetitive fragment of 97 amino acid residues (SEQ ID NO: 4).

Example 2

Sequence Analysis of the Repetitive Fragment of *Euprosthenops australis* MaSp1 Protein The repetitive fragment of the *Euprosthenops australis* MaSp1 protein sequence of Example 1 (SEQ ID NO: 3) was further analyzed by alignment of the repetitive segments of the fragment, see FIG. 1. The alignment was carefully scrutinized and the following structural information was concluded.

The alanine-rich segments of the *Euprosthenops australis* MaSp1 protein are 13-15 amino acid residues long and consists of only alanine residues or all alanine residues but one residue, which is a serine, glutamate or glycine residue.

The repetitive fragment of the *Euprosthenops australis* MaSp1 protein further contains three related, but distinct, types of glycine-rich segments, c.f. FIG. 2A. Two of the glycine-rich segments differ almost only in length and occurrence; the most common glycine-rich segment contains 23 amino acid residues, while a less abundant variant contains 17 amino acid residues. Both of these glycine-rich segments generally lack charged residues or contain one charged residue. In contrast, the shortest glycine-rich segment, containing 14 amino acid residues, uniquely contains the sequence GRGQG (SEQ ID NO: 71) or GQGQG (SEQ ID NO: 72) at the N-terminal end, and GN at the C-terminal end.

The longest glycine-rich segment is represented by the amino acid one letter consensus sequence GQG(G/S)QGG (Q/Y)GG (L/Q)GQGGYGQGA GSS (SEQ ID NO: 5), and lacks charged residues. It is predicted that this segment forms coil structures or $3_1$-helix structures. The mid-sized glycine-rich segment is represented by the amino acid one letter consensus sequence GQGGQGQG(G/R)Y GQG(A/S)G(S/G)S (SEQ ID NO: 6), and lacks charged residues or contains one charged residue. It is predicted that this segment forms coil structures. The shortest glycine-rich segment is represented by the amino acid one letter consensus sequence G(R/Q)GQG(G/R)YGQG (A/S/V)GGN (SEQ ID NO: 7). It is predicted that this segment forms turn structures.

The repetitive fragment of the *Euprosthenops australis* MaSp1 protein is built up from alternating alanine-rich and glycine rich segments, e.g. . . . $A_1G_1A_2G_2A_3G_3A_4G_4A_5G_5$ . . . (SEQ ID NO: 56)

It is observed that each of the above-identified shortest and longest glycine-rich segments generally occur as every second glycine-rich segment, e.g. . . . $A_1G_{short}A_2G_{long}A_3G_{short}A_4G_{long}A_5G_{short}$ (SEQ ID NO: 56) . . . .

In contrast, the less abundant, mid-sized glycine-rich fragment generally occurs in between a glycine-rich segment of the longer type and a glycine-rich segment of the shorter type, e.g. . . . $A_1G_{short}A_2G_{long}A_3G_{mid}A_4G_{short}A_5G_{long}$ . . . (SEQ ID NO: 56)

Example 3

Prediction of Secondary and Tertiary Structure of the Repetitive Fragment of *Euprosthenops australis* MaSp1 Protein Spidroin polypeptides in solution typically fold by formation of hairpin structures, which prefigures the anti-parallel β-sheet structure of the mature fiber. To discern possible folding patterns for the repetitive fragment (SEQ ID NO: 3) of the *Euprosthenops australis* MaSp1 protein of examples 1-2, protein regions that are compatible with formation of hairpin or turn structures were identified. The alanine-rich segments are unlikely candidates for turn formation since they are predicted to form helical structures, and more importantly, these segments are generally held to make up the β-sheets in the fiber.

Using a recently described algorithm for turn predictions (Fuchs, P F & Alix, A J, High accuracy prediction of beta-turns and their types using propensities and multiple alignments. Proteins 59, 828-839 (2005)), the shortest glycine-rich segments shows high likelihood for formation of type II β-turns, while the two longer glycine-rich segments are predicted to form coil structures. The high content of GGX triplets in the longer Gly-rich segments suggests that they can form $3_1$-helix structures.

The repetitive nature of the spidroin amino acid sequences implies an equally repetitive nature of the folding pattern. Taken together, these observations result in a folding of the repetitive fragment of the *Euprosthenops australis* MaSp1 protein as shown in FIG. 2A. It is notable that the positively charged residues almost invariably are located in the proposed turn structures.

From the folding pattern of the repetitive fragment of the *Euprosthenops australis* MaSp1 protein, a motif consisting of alanine-rich segment/(longer) glycine-rich coil segment/alanine-rich segment/(shorter) glycine-rich turn segment/alanine-rich segment/(longer) glycine-rich coil segment/alanine-rich segment, can be discerned (schematically illustrated in FIG. 2A).

Example 4

Sequence Analysis of the Non-Repetitive C-Terminal Fragment of MaSp1 Proteins The primary structure of the C-terminal non-repetitive fragment (SEQ ID NO: 4) of MaSp1 protein from *Euprosthenops australis*, obtained in Example 1, was aligned with a number of known C-terminal fragments of MaSp1 and MaSp2 proteins, inter alia from *Euprosthenops* sp. (Pouchkina-Stantcheva, N N & McQueen-Mason, S J, Molecular studies of a novel dragline silk from a nursery web spider, *Euprosthenops* sp. (Pisauridae). Comp Biochem Physiol B Biochem Mol Biol 138, 371-376 (2004)), *Nephila clavipes* P19837-5 (Xu, M & Lewis, R V, Structure of a protein superfiber: spider dragline silk. Proc Natl Acad Sci USA 87, 7120-7124 (1990)) and others.

From the alignment shown in FIG. 3, starting from the last Ser in the repetitive fragment, it is evident that the C-terminal regions of MaSp1 and MaSp2 are well conserved. *Euprosthenops* sp and *Nephila clavipes* have 95% identical residues; *Euprosthenops australis* and *Nephila clavipes* have 54% identical residues; and *Euprosthenops australis* and *Euprosthenops* sp have 55% identical residues. A consensus sequence of the C-terminal regions of MaSp1 and MaSp2 is provided as SEQ ID NO: 8. In FIG. 3, the following MaSp proteins are aligned, denoted with GenBank accession entries where applicable:

| Species and spidroin protein | Entry |
|---|---|
| *Euprosthenops* sp MaSp1 (Pouchkina-Stantcheva, NN & McQueen-Mason, SJ, ibid) | Cthyb_Esp |
| *Euprosthenops australis* MaSp1 (SEQ ID NO: 4) | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenaries* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

Example 5

Construction of MaSp1 Genes

A DNA sequence encoding the *Euprosthenops australis*-derived protein 5Gly/Ala-CT$_{nat}$ (SEQ ID NO: 9) was amplified by PCR with an Advantage GC2 kit (BD Biosciences, San Jose, Calif., USA), using a MaSp1 clone from the cDNA library of Example 1 as template. Restriction enzyme recognition sites BamHI and HindIII were introduced at the 5'- and 3'-ends, respectively, and a stop codon was introduced upstream of the HindIII site, by use of designed primers. The BamHI-5Gly/Ala-CT$_{nat}$-HindIII construct was then subcloned into a modified pET32 vector (Merck Biosciences, Darmstadt, Germany), prepared as described in Example 6(C) below.

Example 6

Construction of Chimeric MaSp1 Genes (A) REP Gene Fragments

DNA sequences coding for partial repetitive fragments (REP) denoted 3Gly/Ala and 4Gly/Ala were amplified by PCR with LA Taq (TaKaRa Bio; Saint Germain-en-laye, France) in the presence of betaine (Henke W et al, Betaine improves the PCR amplification of GC-rich DNA sequences. Nucleic Acids Res 25, 3957-3958 (1997)), using a partial cDNA clone encoding a repetitive region of *Euprosthenops* sp MaSp1 protein (Pouchkina-Stantcheva, N N & McQueen-Mason, S J, Molecular studies of a novel dragline silk from a nursery web spider, *Euprosthenops* sp. (Pisauridae). Comp Biochem Physiol B Biochem Mol Biol 138, 371-376 (2004)) (GenBank entry CQ974358 or CQ816656) as template. Restriction enzyme recognition sites were introduced at the 5'- and 3'-ends, giving the following constructs: NcoI-3Gly/Ala-NheI and NcoI-4Gly/Ala-NheI to be joined with a CT fragment (see below); and a NcoI-4Gly/Ala-XhoI clone to be individually expressed, where a stop codon was inserted directly upstream of the XhoI site.

(B) CT Gene Fragments

A DNA sequence coding for the non-repetitive C-terminal domain from *Euprosthenops* sp (but with a high degree of similarity to MaSp1 from *Nephila clavipes* and *Nephila senegalensis*) was amplified by PCR using a genomic DNA clone encoding a C-terminal MaSp1 domain (Pouchkina-Stantcheva, N N & McQueen-Mason, S J, Molecular studies of a novel dragline silk from a nursery web spider, *Euprosthenops* sp. (Pisauridae). Comp Biochem Physiol B Biochem Mol Biol 138, 371-376 (2004)). Restriction enzyme recognition sites were introduced at the 5'- and 3'-ends, giving NheI-2Gly/Ala-CT$_{hyb}$-XhoI, to be joined with the 3Gly/Ala and 4Gly/Ala partial REP clones (see above), and NcoI-2Gly/Ala-CT$_{hyb}$-XhoI, to be individually expressed.

(C) Construction of REP-CT Hybrid MaSp1 Genes

The 3Gly/Ala and 4Gly/Ala REP clones were joined with the CT clones using the pCR® 2.1-TOPO® vector (Invitrogen). Then, the resulting, fused 5Gly/Ala-CT$_{hyb}$ and 6Gly/Ala-CT$_{hyb}$ clones were excised with NcoI and XhoI, and subcloned into a modified pET32 vector (Novagen), where the original thrombin cleavage site was removed and a new thrombin site was introduced downstream of the enterokinase cleavage site.

Example 7

Expression of MaSp1 Fusion Proteins

The MaSp1 proteins coded for by the genes constructed in examples 5-6 were expressed as fusion proteins (of the type X-REP-CT) as follows, using a modified pET32vector: thioredoxin-tag/His-tag/S-tag/thrombin cleavage site/MaSp1 gene, encoding a thioredoxin/His$_6$/S-tag/thrombin cleavage site/MaSp1 protein, and an ampicillin resistance gene under control of the T7 promoter.

The different MaSp1 constructs in pET32 expression vectors were transformed into *Escherichia coli* BL21(DE3) cells (Merck Biosciences). The cells were grown at 30° C. in Luria-Bertani medium containing ampicillin to an $OD_{600}$ of 1.0-1.5, induced with IPTG and further incubated for 4 h at room temperature. The cells were harvested by centrifugation, and lysed by DNAseI and lysozyme in 20 mM Tris-HCl, pH 8.0, 20 mM imidazole, with 0.5 M NaCl, and further purified by His-tag affinity chromatography on Ni-NTA agarose (Qiagen, West Sussex, UK). Bound fusion proteins were eluted from the Ni-NTA column with 200 mM imidazole in 20 mM Tris-HCl, pH 8.0, with 0.5 M NaCl, and dialyzed against 20 mM Tris-HCl, pH 8.0. The resulting fusion proteins were >90% pure as judged by coomassie-stained SDS polyacrylamide gels and soluble in 20 mM Tris-HCl, pH 8.0. This process yielded approximately 40 mg/l culture of fusion protein, which was stable for weeks without significant precipitation.

In another experiment, the fusion proteins were expressed as $His_6$/thioredoxin/$His_6$/thrombin cleavage site/MaSp1 proteins from a plasmid containing the corresponding gene and a kanamycin resistance gene under control of the T7 promoter.

Example 8

Formation of Fibers from MaSp1 Proteins

Figure 4:
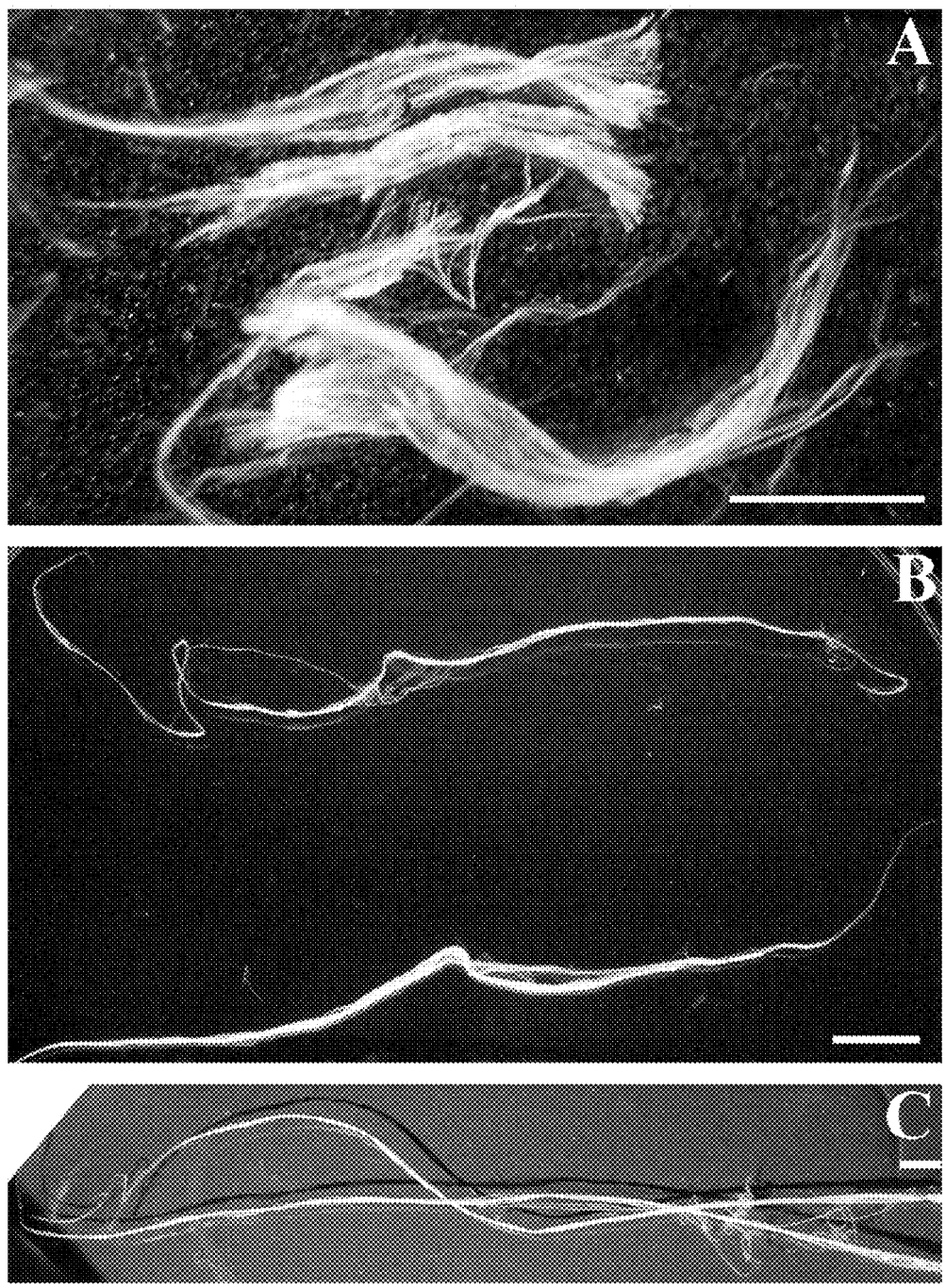
FIG. 4 illustrates macroscopic appearances of fibers formed from spidroin proteins constructed according to examples 5-8. (A): 6Gly/Ala-CT$_{hyb}$ protein (SEQ ID NO: 13) fibers, bar 0.5 cm; (B): 5Gly/Ala-CT$_{nat}$ (SEQ ID NO: 9) protein fibers, bar 1 cm. (C): 5Gly/Ala-CT$_{nat}$ (SEQ ID NO: 9) protein fibers, bar 1 cm.

Cleavage of the tags from the fusion proteins resulting from Example 7, was performed in 20 mM Tris-HCl, pH 8, with a thrombin:fusion protein ratio of 1:1000 (w/w), under very gentle rocking at room temperature. Thrombin cleavage was complete within 30-60 min, as judged by SDS-PAGE. The resulting MaSp1 proteins (FIG. 2B, SEQ ID NOS: 9-13) spontaneously polymerized into macroscopic fibers to varying extents, see Table 1. The fibers were initially formed at the water/air interface. The formation could be observed by the naked eye from about 1 hour of incubation (see FIG. 4A, 4B), and after about 5 hours occurred no further fiber growth. 6Gly/Ala-$CT_{hyb}$ fibers were up to approximately 2 cm long, and 5Gly/Ala-$CT_{nat}$ fibers were ≥10 cm long. Repeated experiments yielded 5Gly/Ala-$CT_{nat}$ fibers that were ≥20 cm (see FIG. 4C), and even ≥2 m long. Fiber formation could be observed by the naked eye from about 10 min of incubation.

Fibers were isolated and washed with buffer and thereafter subjected to N-terminal amino acid sequence analysis, which showed only the sequence of the MaSp1 protein. This shows that the cleaved tags are absent in the fibers.

Example 9

Analysis of MaSp1 Protein Fibers

A. Tensile Strength Measurements

The tensile strength of the 6Gly/Ala-$CT_{hyb}$ (SEQ ID NO: 13) and 5Gly/Ala-$CT_{nat}$ (SEQ ID NO: 9) fibers of example 8 was determined as follows. In order to handle the shorter (1-2 cm) 6Gly/Ala-$CT_{hyb}$ fibers for tensile strength measurements, they were incubated shortly in 15% glycerol in water before they were air-dried. The longer (10 cm) 5Gly/Ala-$CT_{nat}$ fibers were either untreated, incubated shortly in 15% glycerol, or drawn by hand in 75% methanol before air-drying. Tensile strength of air-dried fibers was measured by pulling the fibers in a Zwick Material Tester at a rate of 10 mm/min. See Table 1.

The tensile strength of glycerol-treated air-dried 1-2 cm long fibers from 6Gly/Ala-$CT_{hyb}$ (SEQ ID NO: 13) was about 2 MPa, and the strength of 10 cm fibers from 5Gly/Ala-$CT_{nat}$ (SEQ ID NO: 9) was 4-5 MPa. Ten cm long 5Gly/Ala-$CT_{nat}$ fibers drawn in the dehydrating solvent methanol before air-drying displayed a tensile strength of 2-3 MPa, which is slightly less than for glycerol-treated fibers of the same type. The highest tensile strength now measured was 10 MPa, which was found for an air-dried 10 cm long 5Gly/Ala-$CT_{nat}$ fiber without further treatment.

The range of tensile strengths (2-10 MPa) is comparable to the lower values reported for regenerated spider silk fibers (2-320 MPa). The longest spontaneously formed fibers derive from the 5Gly/Ala-$CT_{nat}$ construct, and such air-dried fibers also show the greatest tensile strength. Potentially, this could be due to its 12-15 residues long poly-Ala segments, relative the 8-14 residue Ala segments in 6Gly/Ala-$CT_{hyb}$, which would give a greater proportion of crystalline β-sheet conformation in the former protein.

TABLE 1

Fiber forming capacity of MaSp1 proteins

| Protein | SEQ ID NO | Fiber forming capacity | Fiber length (cm) | Fiber tensile strength (MPa) |
|---|---|---|---|---|
| 5Gly/Ala-$CT_{nat}$ | 9 | ++++ | ≥10 | 2-10 |
| 5Gly/Ala-$CT_{nat}$ (Example 11) | 9 | +++++ | ≥20 | 180-230 |
| 4Gly/Ala | 10 | aggregates | n.a. | n.a. |
| 2Gly/Ala-$CT_{hyb}$ | 11 | aggregates | n.a. | n.a. |
| 5Gly/Ala-$CT_{hyb}$ | 12 | + | ≤1 | n.d. |
| 6Gly/Ala-$CT_{hyb}$ | 13 | +++ | 1-2 | ≤2 | n.a. = not applicable
n.d. = not determined

B. Scanning Electron Microscopy

Figure 5:
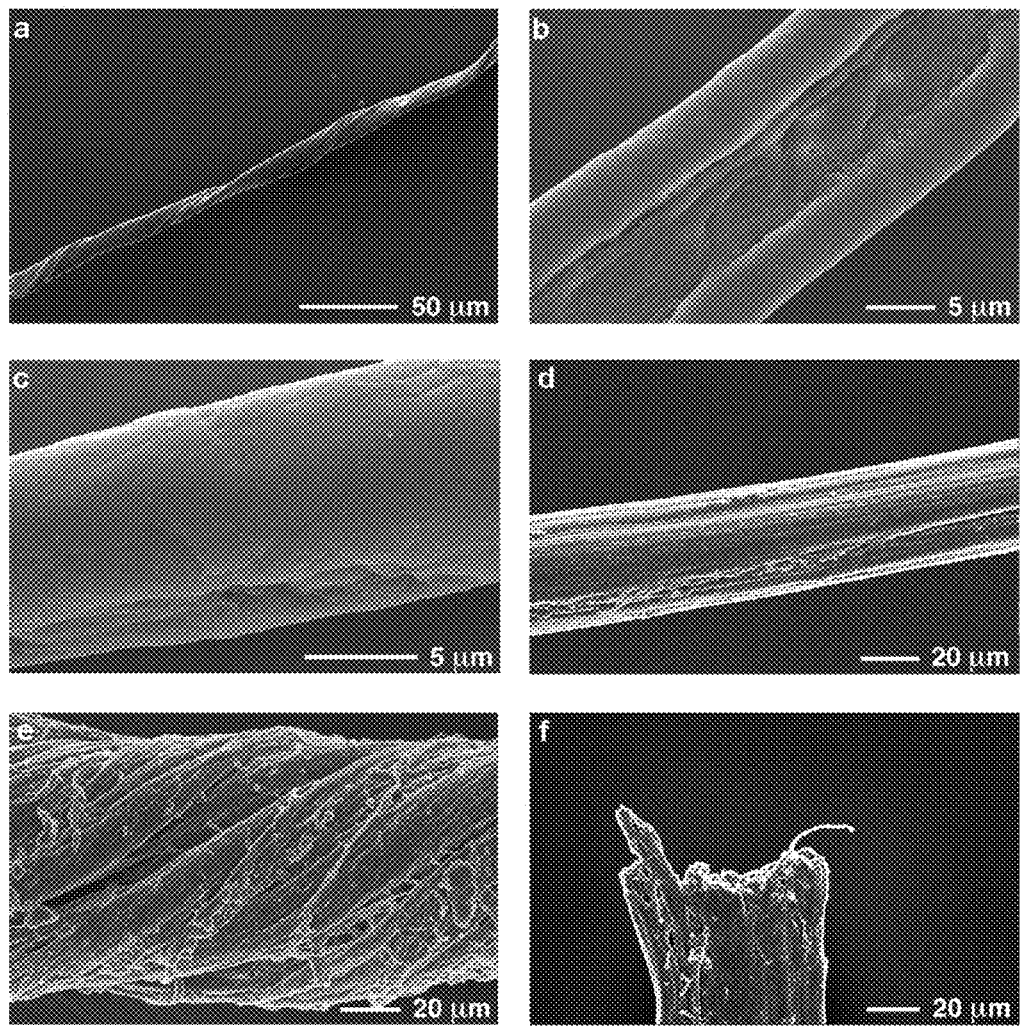
FIG. 5 shows scanning electron microscopy (SEM) micrographs of fibers formed from spidroin proteins constructed according to examples 5-8. Single fibers (a) and gel-phase (b, c) from 6Gly/Ala-CT$_{hyb}$ (SEQ ID NO: 13). Fibers of 5Gly/Ala-CT$_{nat}$ (SEQ ID NO: 9), drawn in 75% methanol, air-dried and applied on SEM-stubs (d, e, f). Fiber twisted before air-drying (e), end of fiber (f).

The microscopic architecture of the 6Gly/Ala-$CT_{hyb}$ and 5Gly/Ala-$CT_{nat}$ fibers was analyzed with scanning electron microscopy (SEM) (FIG. 5). Briefly, samples were applied on SEM-stubs and vacuum-coated with a 6 nm layer of gold and palladium. Specimens were observed and photographed in a LEO 1550 FEG SEM using an acceleration voltage of 10 kV.

This revealed diameters of 10-30 µm for single fibers, with individual fibers displaying rather homogenous diameters (FIG. 5a showing 6Gly/Ala-$CT_{hyb}$, SEQ ID NO: 13). In addition to the macroscopic fibers, gel-like particles were found. After air-drying such particles of 6Gly/Ala-$CT_{hyb}$ directly on a SEM-stub, fibers approximately 10-15 µm in diameter were seen (FIG. 5b, c). The diameter of macroscopic fibers of 5Gly/Ala-$CT_{nat}$ (SEQ ID NO: 9), drawn in 75% methanol and air-dried, were 60-120 µm and they apparently contain several aligned fibers (FIG. 5d-f). Fiber twisted before air-drying (FIG. 5e), end of fiber (FIG. 5f).

C. Circular Dichroism Spectroscopy

Fibers consisting of 6Gly/Ala-$CT_{hyb}$ protein (SEQ ID NO: 13) or 5Gly/Ala-$CT_{nat}$ (SEQ ID NO: 9), prepared in Example 8, were washed in 20 mM phosphate buffer, pH 7, and suspended in 2% SDS in the same buffer. Circular Dichroism spectra from 250 to 190 nm were recorded at 22° C. in a 0.1 cm path length quartz cuvette, using a Jasco J-810 spectropolarimeter. The scan speed was 50 nm/min, response time 2 sec, acquisition interval 0.1 nm, and the band width 1 nm.

Figure 6:
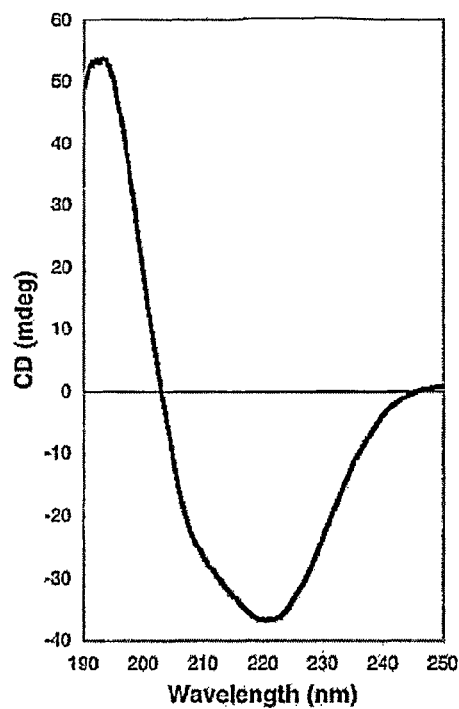
FIG. 6 displays a circular dichroism (CD) spectrum of 6Gly/Ala-CT$_{hyb}$ (SEQ ID NO: 13) fiber.

The spectrum shown in FIG. 6 is an accumulation of three scans of fibers of 6Gly/Ala-$CT_{hyb}$ protein (SEQ ID NO: 13). It displays a minimum at 220 nm and a maximum at 195 nm, features that are characteristic of antiparallel β-sheet structures. Highly similar spectra were obtained for fibers of 5Gly/Ala-CT$_{nat}$ (not shown). The spontaneously formed fibers thus exhibit similar morphology and structure as native and regenerated spider silk fibers.

Example 10

Biocompatibility of Recombinant Spider Silk

Since it is desirable to use spider silk fibers in biomedical applications, the biocompatibility of the fibers has been evaluated by an investigation of effects of recombinantly produced silk using two different cell types.

The MaSp1 protein 5Gly/Ala-CT$_{nat}$ (SEQ ID NO: 9) was expressed in bacteria as described in examples 7-8. Purified protein was used to produce artificial silk fibers with lengths of >10 cm, and even >20-200 cm, and diameters of around 100 μm.

A. Embryonal Mouse Mast Cells

Figure 7:
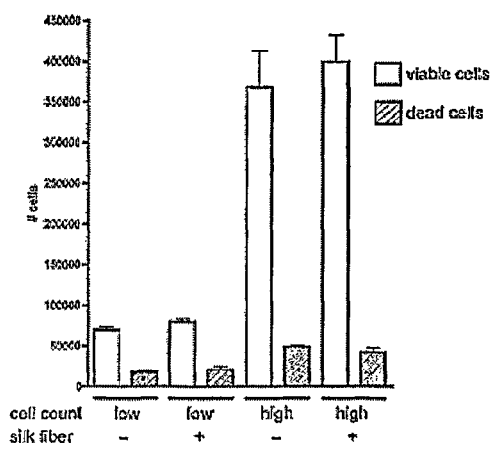
FIG. 7 illustrates the results from a mouse mast cell toxicity study, showing the numbers of live and dead cells after three days of culture in the presence or absence of in vitro produced silk fibers.

Embryonal (day 12.5) mouse mast cells (in vitro proliferated for eight weeks using IL-8 and mast stem cell factor) were seeded at two different cell densities, the higher density being about four times the lower density. These cells do not adhere to the plastic surface, but grow in suspension. Pieces of the silk fiber, each about 0.5 cm long, were added to the wells. Mast cells were incubated for three days, with or without the presence of silk fiber, and thereafter living and dead cells were counted after staining with Trypan blue (FIG. 7). The bars show the mean values with standard error mean, n=2, each sample is counted in triplicate.

The mast cells are not affected by the presence of the silk fibers. After three days of growth, there are no significant differences in cell death or proliferation compared to the negative controls grown without silk fibers.

B. Human Embryonic Kidney (HEK) 293 Cells

Pieces of the silk fiber, about 0.5 cm long, were adsorbed to the bottom of 6-well microtiter plates by letting them dry from a small volume of buffer. The fibers do not detach when cell growth media is added. Human embryonic kidney (HEK) 293 cells were then plated at different cell densities and allowed to grow for a total of six days. The HEK-293 cells adhere and grow attached to the plastic cell surface. The ability of the HEK-293 cells to grow in the proximity of the fibers, and the physical attachment of the cells to the fibers was studied.

Figure 8:
FIG. 8 is a picture of HEK293 cells following exposure to in vitro produced silk fibers in a biocompatibility study.

The HEK-293 cells attached and proliferated normally in the wells containing silk fibers (as observed under the light microscope). The cells grew very closely along the fiber edges, and apparently even grew under a partly detached fiber (FIG. 8). After seven days, the fibers were carefully detached from the plastic surface, and it was clearly seen that groups of cells were physically attached to the fibers. The fiber covers the upper right half of the figure. HEK293-cells are seen attached to the edge of the fiber, and also grow under the fiber.

The two different cell types (mast cells, HEK-293) studied were not affected by the presence of recombinant silk fibers, even at comparatively high amounts of silk. This indicates that the tested artificial silk fibers resemble wild type dragline silk of *Euprosthenops australis*, in being non-toxic and biocompatible. The artificial silk fibers thus appear suitable for biomedical applications.

Example 11

Mechanical Properties and Structure of MaSp1 Protein Fibers

Figure 9:
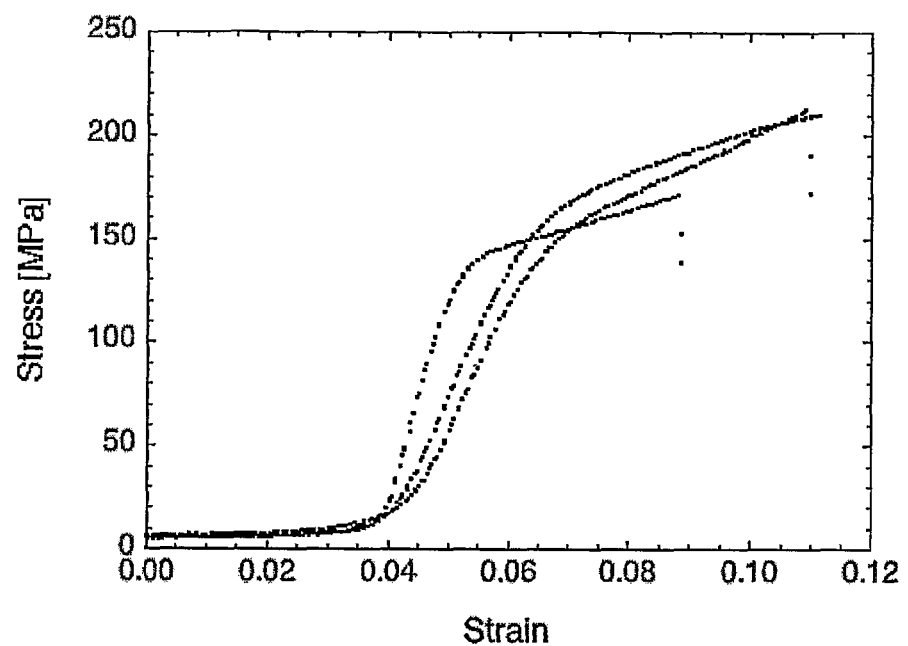
FIG. 9 is a stress-strain curve displaying the tensile strength of double drawn fibers from 5Gly/Ala-CT$_{nat}$ (SEQ ID NO: 9).

The mechanical properties of fibers from 5Gly/Ala-CT$_{nat}$ (SEQ ID NO: 9) were examined using tensile tests performed to yield stress-strain curves (FIG. 9). The tensile properties were characterized using a Zwick Roell Z2.5 material tester (Zwick, Ulm, Germany). The tests were performed in air at ambient conditions (20° C. and 52% relative humidity) using a loading speed of 10 mm/min. Fiber pieces were transferred directly from buffer, mounted and subjected to two stretching-relaxation cycles. In order to generate a homogenous silk thread suitable for tensile testing, the fibers were elongated using stretch-relaxation cycles. First, the fibers were elongated by pulling up to a force of 0.1 N. After relaxation, they were further drawn until a force of 0.25 N was applied.

This treatment generated elongated homogenous fibers with a diameter of approximately 80 μm as determined by height measurements using a Mitutoyo IDC-112B instrument (Mitutoyo Corp, Tokyo, Japan) and confirmed by scanning electron microscopy (SEM) as follows. Before and after stretch-relaxation cycles, fiber pieces were applied on SEM stubs and air-dried overnight. The samples were vacuum-coated with a 6 nm layer of gold and palladium. Specimens were observed and photographed with a LEO 1550 FEG microscope (Carl Zeiss, Oberkochen, Germany) using an acceleration voltage of 10 kV.

The drawn fibers were cut into pieces, the ends of which were fixed between cardboard paper with glue (Loctite 420, Loctite, Göteborg, Sweden). Fiber samples were then fixed in the grips of the material tester and stretched until they broke. Stress-strain curves were constructed using the initial cross-sectional area of the pre-drawn fibre, assuming a circular cross-section. The stress values are normalized to the initial cross-sectional area of the fiber. The strain corresponds to $dL/L_0$ where $L_0$ is the initial length of the fiber and dL is the change in fiber length. In FIG. 9, the stress-strain curves for three different samples of double drawn fibers of 5Gly/Ala-CT$_{nat}$ (SEQ ID NO: 9) are shown, and their tensile strength measured approximately 0.2 GPa.

Figure 10:
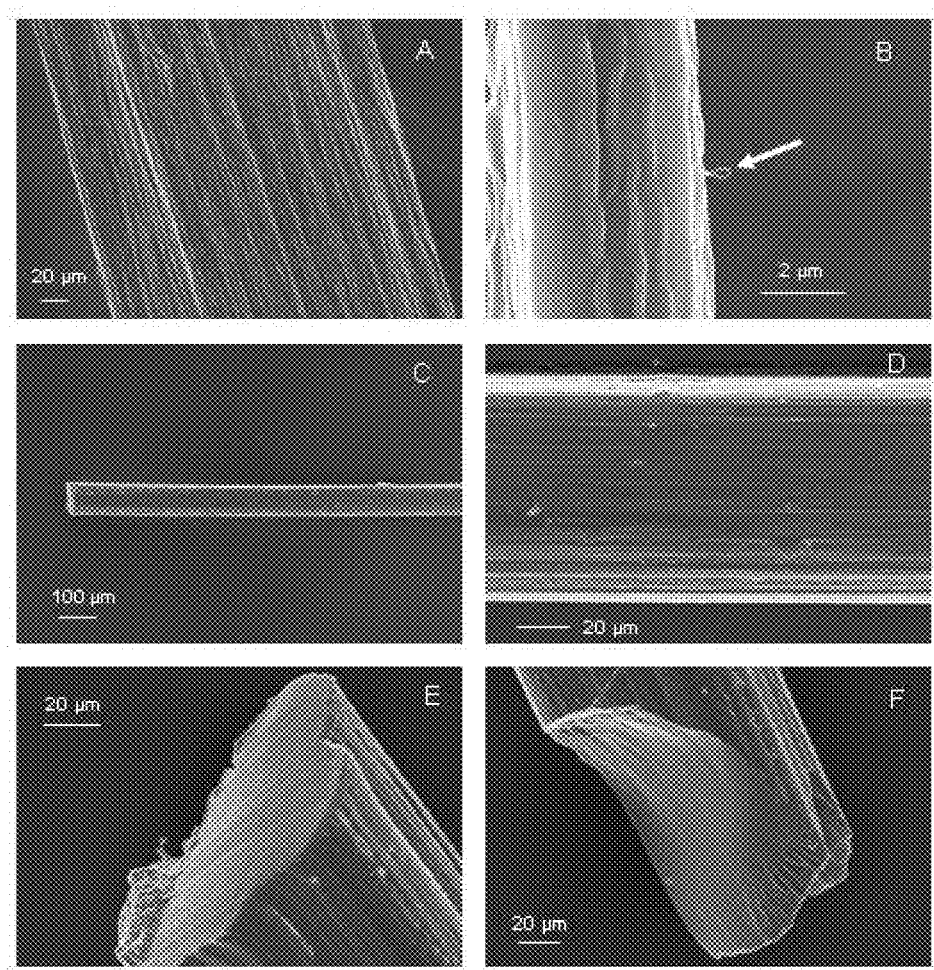
FIG. 10 shows SEM micrographs of recombinant fibers from 5Gly/Ala-CT$_{nat}$ (SEQ ID NO: 9). a,b, Spontaneously formed fibers. The close-up image (b) shows the fibrillar substructure. The small fibril that bulges out (arrow) has a width of about 300 nm. c-f, Fibers after two stretching-relaxation cycles. c and d shows the same fiber at different magnifications. e shows a cut fiber end, and f shows a point of breakage after tensile testing.

The microscopic architecture of the fibers was analyzed by SEM (FIG. 10). The spontaneously formed fibers have a homogenous flattened appearance and a width of up to several hundred micrometers, while the height measures some ten micrometers (FIG. 10a,b).

After the fibers had been subjected to stretch-relaxation cycles, their cross section adopted a more rounded shape with a compact substructure of tightly aligned fibrils (FIG. 10c-f). The appearance of cut or fractured surfaces (FIG. 10e,f) further attest to the compactness of the produced fiber.

In conclusion, the spontaneously formed fibers show similar morphology and mechanical properties as native or regenerated spider silk fibers, even without spinning.

Example 12

Spidroin Protein Variants

Strong intermolecular interactions are thought to contribute to the impressive tensile strength of spider silk. Therefore, variants of miniature spidroins that allow intermolecular covalent cross-linking in the fibers have been produced. Two different mutant spidroin proteins have been constructed by site-directed mutagenesis to introduce two cysteine residues in the first (SEQ ID NO: 14, positions 36 and 37) and the fourth (SEQ ID NO: 15, positions 128 and 129) alanine block, respectively. These variants have been expressed and isolated using the same protocol as described in Examples 7-8 for the genes constructed in Examples 5-6.

These variants (SEQ ID NOS: 14-15) form fibers in the same manner as 5Gly/Ala-CT$_{nat}$ (SEQ ID NO: 9).

In order to elucidate the importance of dimerization of the C-terminal domain, a variant where the cysteine residue in the C-terminal domain is exchanged for a serine residue has been constructed (SEQ ID NO: 16, position 222). However, this variant (SEQ ID NO: 16) forms fibers in the same manner as 5Gly/Ala-CT$_{nat}$ (SEQ ID NO: 9).

Example 13

Removal of LPS and Other Pyrogens from Expressed Spidroin Proteins

*E. coli* cells expressing the desired spidroin fusion protein are washed with the following buffers:
A: 100 mM Tris, pH 8,
B: 5 mM CaCl$_2$, 100 mM Tris, pH 8,
C: 10 mM EDTA, 100 mM Tris, pH 8,
D: 100 mM Tris, pH 8, and
E: 100 mM Tris, pH 8.

Thereafter, the cells are lysed in 20 mM Tris, pH 8 supplemented with lysozyme and DNaseI. The protein sample is then loaded on a Ni-sepharose matrix and washed with 20 mM Tris, 10-100 mM imidazole, pH 8 before elution with 20 mM Tris, 100-300 mM imidazole, pH 8. Relevant fractions are pooled and dialyzed against 20 mM Tris, pH 8 over night. The protein sample is then supplemented with 100 μM CaCl$_2$ and finally passed through an EndoTrap Blue column, previously equilibrated with 20 mM Tris, 100 μM CaCl$_2$, pH 8. In this way, protein samples with a pyrogen content of 1 EU/mg protein can be obtained, as judged by IPT and a LAL kinetic assay.

The fusion protein is then proteolytically cleaved with thrombin using a 1:1000 (w/w) thrombin:fusion protein ratio, which induces fiber formation (as described above). The fibers are washed 3 times in 20 mM Tris, pH 8 and finally 3 times in water. This gives fibers with a pyrogen content of 0.25 EU/mg fiber.

The structural characteristics of the fibers are unaffected after autoclaving at 125° C. and 1.5 bar for 10 min, which enables efficient sterilization of the material. The fibers are chemically stable and can not be solubilized in either of 8 M urea, 6 M GuaHCl, or neat HAc. However, the fibers can be solubilized in neat HFIP or formic acid.

The invention claimed is:

1. A support for cell adherence and growth, comprising a polymer of a major ampullate spidroin protein, which major ampullate spidroin protein is consisting of from 150 to 420 amino acid residues and being defined by the formula REP-CT, wherein REP is a protein fragment having from 80 to 300 amino acid residues, wherein said fragment is selected from the group of $L(AG)_nL$, $L(AG)_nAL$, $L(GA)_nL$, and $L(GA)_nGL$, wherein n is an integer from 4 to 8;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 20 amino acid residues; and CT is a protein fragment having from 70 to 120 amino acid residues and at least 80% identity to an amino acid sequence selected from the group consisting of SEQ ID NO: 4, amino acid residues 172-269 of SEQ ID NO: 9, and amino acid residues 172-269 of SEQ ID NO: 16.

2. The support for cell adherence and growth according to claim 1, wherein the polymer has a shape selected from the group consisting of a fiber, a foam, a gel, a mesh, and a film.

3. The support for cell adherence and growth according to claim 1, wherein n is an integer from 4 to 6.

4. The support for cell adherence and growth according to claim 3, wherein n is an integer from 4 to 5.

5. The support for cell adherence and growth according to claim 1, wherein
each individual A segment is, or has at least 80% identity to, an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3; amino acid residues 31-42, 61-75, 90-104, 122-135 and 153-171 of SEQ ID NO: 9; amino acid residues 12-25, 46-60, 75-88, 112-119, 150-158 and 173-180 of SEQ ID NO: 13; amino acid residues 31-42 of SEQ ID NO: 14; and amino acid residues 122-135 of SEQ ID NO: 15; and
each individual G segment is, or has at least 80% identity to, an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3; SEQ ID NOS: 5-7; amino acid residues 11-30, 43-60, 76-89, 105-121 and 136-152 of SEQ ID NO: 9; and amino acid residues 1-11, 26-45, 61-74, 89-111, 120-149 and 159-172 of SEQ ID NO: 13.

6. The support for cell adherence and growth according to claim 1, wherein said CT fragment has at least 90% identity to an amino acid sequence selected from the group consisting of SEQ ID NO: 4, amino acid residues 172-269 of SEQ ID NO: 9, and amino acid residues 172-269 of SEQ ID NO: 16.

7. The support for cell adherence and growth according to claim 6, wherein said CT fragment has at least 95% identity to an amino acid sequence selected from the group consisting of SEQ ID NO: 4, amino acid residues 172-269 of SEQ ID NO: 9, and amino acid residues 172-269 of SEQ ID NO: 16.

8. The support for cell adherence and growth according to claim 7, wherein said CT fragment is an amino acid sequence selected from the group consisting of SEQ ID NO: 4, amino acid residues 172-269 of SEQ ID NO: 9, and amino acid residues 172-269 of SEQ ID NO: 16.

9. The support for cell adherence and growth according to claim 1, wherein the major ampullate spidroin protein has at least 80% identity to amino acid residues 11-269 of SEQ ID NO: 9.

10. The support for cell adherence and growth according to claim 9, wherein the major ampullate spidroin protein has at least 90% identity to amino acid residues 11-269 of SEQ ID NO: 9.

11. The support for cell adherence and growth according to claim 10, wherein the major ampullate spidroin protein has at least 95% identity to amino acid residues 11-269 of SEQ ID NO: 9.

12. The support for cell adherence and growth according to claim 1, wherein the major ampullate spidroin protein is selected from SEQ ID NOS: 9 and 12-16.

13. The support for cell adherence and growth according to claim 12, wherein the major ampullate spidroin protein is SEQ ID NO: 9.

14. The support for cell adherence and growth according to claim 1, wherein the content of lipopolysaccharide (LPS) and other pyrogens is 1 EU/mg of isolated protein or lower.

15. A method of culturing eukaryotic cells, comprising:
growing said eukaryotic cells attached to the support for cell adherence and growth according to claim 1.

16. A medical product, comprising:
the support for cell adherence and growth according to claim 1.

17. The medical product according to claim 16, wherein said medical product is selected from the group consisting of implants, wound closure systems, band-aids, sutures, wound dressings and scaffolds for tissue engineering and guided cell regeneration.

18. The medical product according to claim 17, wherein said medical product is an implant.

19. The medical product according to claim 17, wherein said medical product is selected from the group consisting of scaffolds for tissue engineering and guided cell regeneration.

20. The medical product according to claim 16, further comprising eukaryotic cells adhered to and growing on said support.

* * * * *